US012656342B2

(12) United States Patent
Labaer et al.

(10) Patent No.: US 12,656,342 B2
(45) Date of Patent: Jun. 16, 2026

(54) ADAPTATION OF NAPPA FOR SURFACE PLASMON RESONANCE IMAGING ANALYSES

(71) Applicant: ARIZONA BOARD OF REGENTS ON BEHALF OF ARIZONA STATE UNIVERSITY, Scottsdale, AZ (US)

(72) Inventors: Joshua Labaer, Chandler, AZ (US); Brianne Petritis, Peachtree Corners, GA (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 1077 days.

(21) Appl. No.: 17/251,418

(22) PCT Filed: Jun. 12, 2019

(86) PCT No.: PCT/US2019/036734
§ 371 (c)(1),
(2) Date: Dec. 11, 2020

(87) PCT Pub. No.: WO2019/241361
PCT Pub. Date: Dec. 19, 2019

(65) Prior Publication Data
US 2022/0042982 A1     Feb. 10, 2022

Related U.S. Application Data

(60) Provisional application No. 62/684,095, filed on Jun. 12, 2018.

(51) Int. Cl.
*G01N 33/543* (2006.01)
*B01J 19/00* (2006.01)
*G01N 33/68* (2006.01)

(52) U.S. Cl.
CPC .... *G01N 33/54373* (2013.01); *B01J 19/0046* (2013.01); *G01N 33/6842* (2013.01); *G01N 33/6845* (2013.01); *B01J 2219/00605* (2013.01); *B01J 2219/00725* (2013.01)

(58) Field of Classification Search
CPC .......... G01N 33/54373; G01N 33/6845; B01J 2219/00605; B01J 19/0046
USPC ....................................................... 436/525
See application file for complete search history.

(56) References Cited

U.S. PATENT DOCUMENTS

| | | | |
|---|---|---|---|
| 7,067,322 B2 | 6/2006 | Corn et al. | |
| 7,150,978 B2 | 12/2006 | Yanagawa et al. | |
| 2008/0090734 A1 | 4/2008 | Xu et al. | |
| 2008/0293591 A1* | 11/2008 | Taussig .................. | C07K 1/047 506/10 |
| 2009/0311338 A1* | 12/2009 | Pathak ..................... | C08H 1/00 514/723 |

| | | | |
|---|---|---|---|
| 2010/0121738 A1* | 5/2010 | Predki .................. | G06Q 10/103 705/26.1 |
| 2012/0178640 A1 | 7/2012 | Strano et al. | |
| 2016/0258944 A1* | 9/2016 | Wiktor ............. | G01N 33/54366 |
| 2017/0212101 A1* | 7/2017 | Zhu .................... | G01N 33/5308 |

FOREIGN PATENT DOCUMENTS

| | | | | |
|---|---|---|---|---|
| WO | WO-2009060065 A1 * | 5/2009 | .............. | C12Q 1/48 |
| WO | 2019241361 A1 | 12/2019 | | |

OTHER PUBLICATIONS

Ramachandran et al., On-Chip Protein Synthesis for Making Microarrays. In: New and Emerging Proteomic Techniques. Methods in Molecular Biology, vol. 328, pp. 1-14, Humana Press, (2006) (Year: 2006).*

U.S. Receiving Office, International Search Report and Written Opinion of the International Searching Authority, in PCT/US2019/036734, Sep. 3, 2019, 12 pages.

Aldridge, B. B., Burke, J. M., Lauffenburger, D. A., & Sorger, P. K. (2006). "Physicochemical modelling of cell signalling pathways." Nature Cell Biology, 8(11), 1195-1203. doi:10.1038/ncb1497.

Davids, M. S. (2017). "Targeting BCL-2 in B-cell lymphomas." Blood, 130(9), 1081-1088. doi:10.1182/blood-2017-04-737338.

Davis, M. J., Ha, B. H., Holman, E. C., Halaban, R., Schlessinger, J., & Boggon, T. J. (2013). "RAC1(P29S) is a spontaneously activating cancer-associated GTPase." Proceedings of the National Academy of Sciences of the United States of America, 110(3), 912-917. doi:10.1073/pnas.1220895110.

De Gorter, D. J. J., Vos, J. C. M., Pals, S. T., & Spaargaren, M. (2007). "The B cell antigen receptor controls AP-1 and NFAT activity through Ras-mediated activation of Ral." Journal of Immunology, 178(3), 1405-1414. doi:DOI 10.4049/jimmunol.178.3.1405.

Deng, J., Isik, E., Fernandes, S. M., Brown, J. R., Letai, A., & Davids, M. S. (2015). "Ibrutinib Therapy Increases BCL-2 Dependence and Enhances Sensitivity to Venetoclax in CLL." Blood, 126(23).

(Continued)

*Primary Examiner* — Gregory S Emch
*Assistant Examiner* — Omar Ramadan
(74) *Attorney, Agent, or Firm* — Fuller IP Law LLC; Rodney J. Fuller

(57) ABSTRACT

Disclosed is a method that combines high throughput and flexible nature of a cell-free protein microarray with the quantitative capability of surface plasmon resonance to detect>400 different protein interactions in<1 hour. A method of detecting interactions between a targeting agent and one or more proteins of interest is disclosed. The method includes producing a set of proteins of interest using a cell-free protein expression system; providing the set of proteins of interest on a protein microarray wherein each spot in the array comprises a protein of interest; contacting the protein microarray with a targeting agent that binds to one or more of the set of proteins of interest; and detecting the binding of the targeting agent to the set of proteins of interest using surface plasmon resonance imaging (SPRi), thereby detecting the targeting agent and one or more proteins of interest in the micro array.

14 Claims, 23 Drawing Sheets

(56) References Cited

OTHER PUBLICATIONS

England, C. G., Luo, H. M., & Cai, W. B. (2015). "HaloTag Technology: A Versatile Platform for Biomedical Applications." Bioconjugate Chemistry, 26(6), 975-986. doi:10.1021/acs.bioconjchem.5b00191.

Festa, F., Steel, J., Bian, X. F., & Labaer, J. (2013). "High-throughput cloning and expression library creation for functional proteomics." Proteomics, 13(9), 1381-1399. doi:10.1002/pmic.201200456.

Fumia, H. F., & Martins, M. L. (2013). "Boolean Network Model for Cancer Pathways: Predicting Carcinogenesis and Targeted Therapy Outcomes." Plos One, 8(7). doi:ARTN e69008.

Gonzalez, M. W., & Kann, M. G. (2012). "Chapter 4: Protein Interactions and Disease." Plos Computational Biology, 8(12). doi:ARTN e1002819.

Hall, M. P., Unch, J., Binkowski, B. F., Valley, M. P., Butler, B. L., Wood, M. G., . . . Wood, K. V. (2012). "Engineered Luciferase Reporter from a Deep Sea Shrimp Utilizing a Novel Imidazopyrazinone Substrate." Acs Chemical Biology, 7(11), 1848-1857. doi:10.1021/cb3002478.

Herrero-Gonzalez, S., & Di Cristofano, A. (2011). "New Routes to Old Places: PIK3R1 and PIK3R2 Join PIK3CA and PTEN as Endometrial Cancer Genes." Cancer Discovery, 1(2), 106-107. doi:10.1158/2159-8290.Cd-11-0116.

Heydari, T., Heidari, M., Mashinchian, O., Wojcik, M., Xu, K., Dalby, M. J., . . . Ejtehadi, M. R. (2017). "Development of a Virtual Cell Model to Predict Cell Response to Substrate Topography." Acs Nano, 11(9), 9084-9092. doi:10.1021/acsnano.7b03732.

Hiratsuka, T., Takei, Y., Ohmori, R., Imai, Y., Ozeki, M., Tamaki, K., . . . Tsuruyama, T. (2016). "ZFP521 contributes to pre-B-cell lymphomagenesis through modulation of the pre-B-cell receptor signaling pathway." Oncogene, 35(25), 3227-3238. doi:10.1038/onc.2015.385.

Ito, T., Chiba, T., Ozawa, R., Yoshida, M., Hattori, M., & Sakaki, Y. (2001). "A comprehensive two-hybrid analysis to explore the yeast protein interactome." Proceedings of the National Academy of Sciences of the United States of America, 98(8), 4569-4574. doi:DOI 10.1073/pnas.061034498.

Janes, K. A., & Yaffe, M. B. (2006). "Data-driven modelling of signal-transduction networks." Nature Reviews Molecular Cell Biology, 7(11), 820-828. doi:10.1038/nrm2041.

Karlsson, M., Ekeroth, J., Elwing, H., & Carlsson, U. (2005). "Reduction of irreversible protein adsorption on solid surfaces by protein engineering for increased stability." Journal of Biological Chemistry, 280(27), 25558-25564. doi:DOI 10.1074/jbc.M503665200.

Karthikeyan, K., Barker, K., Tang, Y. Y., Kahn, P., Wiktor, P., Brunner, A., . . . Qiu, J. (2016). "A Contra Capture Protein Array Platform for Studying Post-translationally Modified (PTM) Auto-antigenomes." Molecular & Cellular Proteomics, 15(7), 2324-2337. doi:10.1074/mcp.M115.057661.

Kirouac, D. C., Saez-Rodriguez, J., Swantek, J., Burke, J. M., Lauffenburger, D. A., & Sorger, P. K. (2012). "Creating and analyzing pathway and protein interaction compendia for modelling signal transduction networks." Bmc Systems Biology, 6. doi:Artn 29.

Kitchen, J., Saunders, R. E., & Warwicker, J. (2008). "Charge environments around phosphorylation sites in proteins." Bmc Structural Biology, 8. doi:Artn 19.

Kumawat, A., Chakrabarty, S., & Kulkarni, K. (2017). "Nucleotide Dependent Switching in Rho GTPase: Conformational Heterogeneity and Competing Molecular Interactions." Scientific Reports, 7. doi:ARTN 45829.

Logue, J. S., & Morrison, D. K. (2012). "Complexity in the signaling network: insights from the use of targeted inhibitors in cancer therapy." Genes & Development, 26(7), 641-650. doi:10.1101/gad.186965.112.

Machleidt, T., Woodroofe, C. C., Schwinn, M. K., Mendez, J., Robers, M. B., Zimmerman, K., . . . Wood, K. V. (2015). "NanoBRET—A Novel BRET Platform for the Analysis of Protein-Protein Interactions." Acs Chemical Biology, 10(8), 1797-1804. doi:10.1021/acschembio.5b00143.

Mathas, S., Hinz, M., Anagnostopoulos, I., Krappmann, D., Lietz, A., Jundt, F., . . . Scheidereit, C. (2002). "Aberrantly expressed c-Jun and JunB are a hallmark of Hodgkin lymphoma calls, stimulate proliferation and synergize with NF-kappa B." Blood, 100(11), 742a-742a.

Mayeux, J., Skaug, B., Luo, W., Russell, L. M., John, S., Saelee, P., . . . Satterthwaite, A. B. (2015). "Genetic Interaction between Lyn, Ets1, and Btk in the Control of Antibody Levels." Journal of Immunology, 195(5), 1955-1963. doi:10.4049/jimmunol.1500165.

Middendorp, S., Dingjan, G. M., Maas, A., Dahlenborg, K., & Hendriks, R. W. (2003). "Function of Bruton's tyrosine kinase during B cell development is partially independent of its catalytic activity." Journal of Immunology, 171(11), 5988-5996.

Murray, D., Matsumoto, L. H., Buser, C. A., Tsang, J., Sigal, C. T., Ben-Tal, N., . . . McLaughlin, S. (1998). "Electrostatics and the membrane association of Src: Theory and experiment." Biochemistry, 37(8), 2145-2159. doi:DOI 10.1021/bi972012b.

Nishi, H., Hashimoto, K., & Panchenko, A. R. (2011). "Phosphorylation in Protein-Protein Binding: Effect on Stability and Function." Structure, 19(12), 1807-1815. doi:10.1016/j.str.2011.09.021.

Nishi, H., Shaytan, A., & Panchenko, A. R. (2014). "Physicochemical mechanisms of protein regulation by phosphorylation." Frontiers in Genetics, 5. doi:ARTN 270.

Okada, T., Maeda, A., Iwamatsu, A., Gotoh, K., & Kurosaki, T. (2000). "BCAP: The tyrosine kinase substrate that connects B cell receptor to phosphoinositide 3-kinase activation." Immunity, 13(6), 817-827. doi:Doi 10.1016/S1074-7613(00)00079-0.

Oshannessy, D. J., Brighamburke, M., Soneson, K. K., Hensley, P., & Brooks, I. (1993). "Determination of Rate and Equilibrium Binding Constants for Macromolecular Interactions Using Surface-Plasmon Resonance—Use of Nonlinear Least-Squares Analysis-Methods." Analytical Biochemistry, 212(2), 457-468. doi:DOI 10.1006/abio.1993.1355.

Pollard, T. D. (2010). "A guide to simple and informative binding assays." Molecular Biology of the Cell, 21(23), 4061-4067. doi:10.1091/mbc.E10-08-0683.

Porter, A. P., Papaioannou, A., & Malliri, A. (2016). "Deregulation of Rho GTPases in cancer." Small GTPases, 7(3), 123-138. doi:10.1080/21541248.2016.1173767.

Prasad, T. S. K., Goel, R., Kandasamy, K., Keerthikumar, S., Kumar, S., Mathivanan, S., . . . Pandey, A. (2009). "Human Protein Reference Database-2009 update." Nucleic Acids Research, 37, D767-D772. doi:10.1093/nar/gkn892.

Ramachandran, N., Hainsworth, E., Bhullar, B., Eisenstein, S., Rosen, B., Lau, A. Y., . . . LaBaer, J. (2004). "Self-assembling protein microarrays." Science, 305(5680), 86-90. doi:DOI 10.1126/science.1097639.

Ramachandran, N., Raphael, J. V., Hainsworth, E., Demirkan, G., Fuentes, M. G., Rolfs, A., . . . LaBaer, J. (2008). Next-generation high-density self-assembling functional protein arrays. Nature Methods, 5(6), 535-538. doi:10.1038/Nmeth.1210.

Rauf, F., Festa, F., Park, J. G., Magee, M., Eaton, S., Rinaldi, C., . . . LaBaer, J. (2018). "Ibrutinib inhibition of ERBB4 reduces cell growth in a WNT5A-dependent manner." Oncogene. doi:10.1038/s41388-017-0079-x.

Russell, L., John, S., Cullen, J., Luo, W., Shlomchik, M. J., & Garrett-Sinha, L. A. (2015). "Requirement for Transcription Factor Ets1 in B Cell Tolerance to Self-Antigens." Journal of Immunology, 195(8), 3574-3583. doi:10.4049/jimmunol.1500776.

Sachs, K., Perez, O., Pe'er, D., Lauffenburger, D. A., & Nolan, G. P. (2005). "Causal protein-signaling networks derived from multiparameter single-cell data." Science, 308(5721), 523-529. doi:10.1126/science.1105809.

Saito, K., Tolias, K. F., Saci, A., Koon, H. B., Humphries, L. A., Scharenberg, A., . . . Carpenter, C. L. (2003). "BTK regulates Ptdlns-4,5-P-2 synthesis: Importance for calcium signaling and PI3K activity." Immunity, 19(5), 669-678. doi:Doi 10.1016/S1074-7613(03)00297-8.

(56)          References Cited

OTHER PUBLICATIONS

Saul, J., Petritis, B., Sau, S., Rauf, F., Gaskin, M., Ober-Reynolds, B., . . . LaBaer, J. (2014). "Development of a full-length human protein production pipeline." Protein Science, 23(8), 1123-1135. doi:10.1002/pro.2484.

Schinzel, A., Kaufmann, T., & Borner, C. (2004). "Bcl-2 family members: intracellular targeting, membrane-insertion, and changes in subcellular localization." Biochimica Et Biophysica Acta-Molecular Cell Research, 1644(2-3), 95-105. doi:10.1016/j.bbamcr.2003.09.006.

Schreiber, G., Haran, G., & Zhou, H. X. (2009). "Fundamental Aspects of Protein-Protein Association Kinetics." Chemical Reviews, 109(3), 839-860. doi:10.1021/cr800373w.

Seefeld, T. H., Halpern, A. R., & Corn, R. M. (2012). "On-Chip Synthesis of Protein Microarrays from DNA Microarrays via Coupled In Vitro Transcription and Translation for Surface Plasmon Resonance Imaging Biosensor Applications" J Am Chem Soc, 134(30), 12358-12361.

Serber, Z., & Ferrell, J. E. (2007). "Tuning bulk electrostatics to regulate protein function." Cell, 128(3), 441-444. doi:10.1016/j.cell.2007.01.018.

Stark, C., Breitkreutz, B. J., Reguly, T., Boucher, L., Breitkreutz, A., & Tyers, M. (2006). "BioGRID: a general repository for interaction datasets." Nucleic Acids Research, 34, D535-D539. doi:10.1093/nar/gkj109.

Stumpf, M. P. H., Thorne, T., de Silva, E., Stewart, R., An, H. J., Lappe, M., & Wiuf, C. (2008). "Estimating the size of the human interactome." Proceedings of the National Academy of Sciences of the United States of America, 105(19), 6959-6964. doi:10.1073/pnas.0708078105.

Tarrant, M. K., & Cole, P. A. (2009). "The Chemical Biology of Protein Phosphorylation." Annual Review of Biochemistry, 78, 797-825. doi:10.1146/annurev.biochem.78.070907.103047.

Testoni, M., Chung, E. Y. L., Priebe, V., & Bertoni, F. (2015). "The transcription factor ETS1 in lymphomas: friend or foe?" Leukemia & Lymphoma, 56(7), 1975-1980. doi:10.3109/10428194.2014.981670.

Troen, G., Nygaard, V., Jenssen, T. K., Ikonomou, I. M., Tierens, A., Matutes, E., . . . Delabie, J. (2004). "Constitutive expression of the AP-1 transcription factors c-jun, junD, junB, and c-fos and the marginal zone B-cell transcription factor notch2 in splenic marginal zone lymphoma." Journal of Molecular Diagnostics, 6(4), 297-307. doi:Doi 10.1016/S1525-1578(10)60525-9.

Tsuchiya, A., Kanno, T., & Nishizaki, T. (2014). "PI3 kinase directly phosphorylates Akt1/2 at Ser473/474 in the insulin signal transduction pathway." Journal of Endocrinology, 220(1), 49-59. doi:10.1530/Joe-13-0172.

Vetter, I. R., & Wittinghofer, A. (2001). "Signal transduction—The guanine nucleotide-binding switch in three dimensions." Science, 294(5545), 1299-1304. doi:DOI 10.1126/science.1062023.

Wang, J., Barker, K., Steel, J., Park, J., Saul, J., Festa, F., . . . Qiu, J. (2013). "A versatile protein microarray platform enabling antibody profiling against denatured proteins." Proteomics Clinical Applications, 7(5-6), 378-383. doi:10.1002/prca.201200062.

Woolery, A. R., Yu, X. B., LaBaer, J., & Orth, K. (2014). "AMPylation of Rho GTPases Subverts Multiple Host Signaling Processes." Journal of Biological Chemistry, 289(47). doi:10.1074/jbc.M114.601310.

Yarbrough, M. L., Li, Y., Kinch, L. N., Grishin, N. V., Ball, H. L., & Orth, K. (2009). "AMPylation of Rho GTPases by Vibrio VopS Disrupts Effector Binding and Downstream Signaling." Science, 323(5911), 269-272. doi:10.1126/science.1166382.

Yu, X. B., & LaBaer, J. (2015). "High-throughput identification of proteins with AMPylation using self-assembled human protein (NAPPA) microarrays." Nature Protocols, 10(5), 756-767. doi:10.1038/nprot.2015.044.

Yu, X., Petritis, B., Duan, H., Xu, D., & LaBaer, J. (2018). "Advances in cell-free protein array methods." Expert Rev Proteomics, 15(1), 1-11. doi:10.1080/14789450.2018.1415146.

Zhao, J. J., Cheng, H. L., Jia, S. D., Wang, L., Gjoerup, O. V., Mikami, A., & Roberts, T. M. (2006). "The p110 alpha isoform of PI3K is essential for proper growth factor signaling and oncogenic transformation." Proceedings of the National Academy of Sciences of the United States of America, 103(44), 16296-16300. doi:10.1073/pnas.0607899103.

* cited by examiner

RAC1: All targets    RAC1: NP-targets    RAC1: LT-targets

Inactive  69  Active    Inactive  59  Active    Inactive  65  Active 0  95    0  95    2  78

FIG. 7

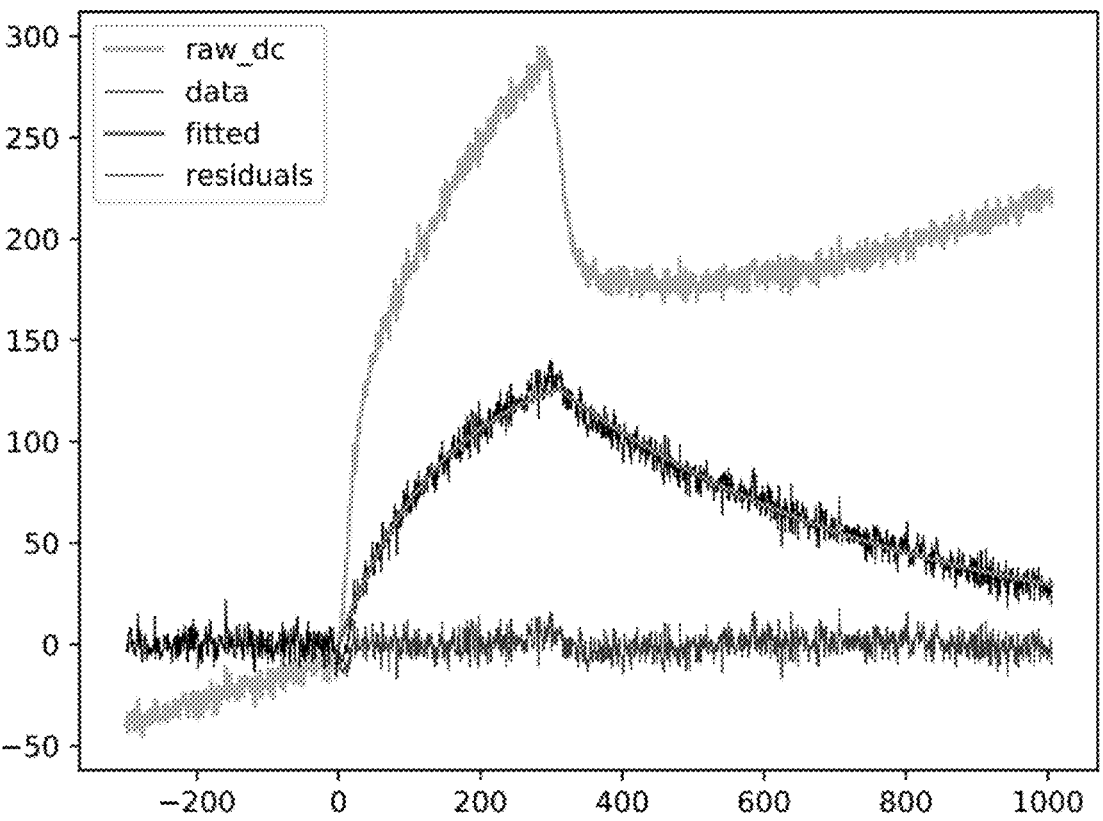

| Options | Scrubber2 | SPRite |
|---|---|---|
| Automated | | Yes |
| Zeroes Data | Yes | Yes |
| Calibrates | | Yes |
| Alphabetizes | | Yes |
| References | Yes | Yes |
| Corrects drift | | Yes |
| Spike Correction | Yes | |
| Models | 1:1 Langmuir | 1:1 Langmuir |
| | 1:1 Langmuir with mass transport | |
| Sensorgrams exported | | Yes |
| Saves data | | Yes |
| Throughput | 1x | 39x - 107x* |
| Analysis-to-analysis correlation | $R^2 = 1$ | $R^2 = 1$ |
| Open source software | | Yes |

* SPRite throughput depends on type of fitting performed

FIG. 8

ADAPTATION OF NAPPA FOR SURFACE PLASMON RESONANCE IMAGING ANALYSES

CROSS REFERENCE TO RELATED APPLICATION APPLICATIONS

This application is a 371 U.S. national stage application of PCT/US2019/036734, filed on Jun. 12, 2019, which claims the benefit of U.S. Provisional Application No. 62/684,095, filed Jun. 12, 2018. Each of these applications is hereby incorporated by reference in its entirety.

FIELD

This disclosure relates to systems and methods for analyzing protein interactions and in particular, to adaptation of nucleic acid programmable protein arrays (NAPPA) for surface plasmon resonance imaging analyses and uses thereof.

BACKGROUND

Cellular responses are mediated through complex and dynamic protein interaction networks (Karp & Patton, 2013). Perturbations to finely-tuned homeostatic signaling pathways have been implicated in numerous diseases, including Huntington's disease, Von Hippel-Lindau syndrome, cystic fibrosis, Alzheimer's disease, and cancer (Gonzalez & Kann, 2012). Innate and acquired signaling crosstalk can also result in drug resistance (Logue & Morrison, 2012). Thus, accurate maps of signaling pathways are needed in order to provide an in-depth understanding of disease initiation and progression, predict drug toxicity and resistance, result in better drug design and targeted therapies, create more effective combinational therapies, and personalize medicine based on the unique genetic profile of the tumor or patient.

SUMMARY

Dynamic protein-protein interactions drive cellular responses in homeostasis, disease, therapeutic response, and drug resistance. However, no high throughput method exists that can characterize the on-rates, off-rates, and binding affinities of protein interactions. Disclosed is a method which combines high throughput and flexible nature of a cell-free protein microarray with the quantitative capability of surface plasmon resonance to detect>400 different protein interactions in <1 hour. The disclosed method allows any protein to be produced as long as the plasmid cDNA can be constructed using appropriately-matched expression milieu. Moreover, the role of post-translational modifications on protein interactions can be studied by the method since the arrayed proteins can be modified in various ways (e.g., phosphorylated in a cell-specific manner).

In one aspect, the present disclosure provides a method of detecting interactions between a targeting agent and one or more proteins of interest, comprising: producing a set of proteins of interest using a cell-free protein expression system; providing the set of proteins of interest on a protein microarray wherein each spot in the array comprises a protein of interest; contacting the protein microarray with a targeting agent that binds to one or more of the set of proteins of interest; and detecting the binding of the targeting agent to the set of proteins of interest using surface plasmon resonance imaging (SPRi), thereby detecting the targeting agent and one or more proteins of interest in the micro array.

In some examples, the method further comprising modifying the set of proteins by post-translational modification (PTM), such as phosphorylation, AMPylation, citrullination or glycosylation, such as by using specific glycosyltransferases during or after protein expression. In some examples of the disclosed methods, providing the set of proteins of interest in a protein microarray comprises attaching the proteins in the array of proteins of interest to a solid or semisolid surface. In some examples, the solid or semisolid surface comprises a nucleic acid programmable protein array (NAPPA) slide. In some examples, attaching the proteins in the array of proteins of interest to the solid or semisolid surface comprises using a capture moiety that specifically binds a targeting moiety on the proteins of interest. In some examples, the capture moiety comprises an antibody, streptavidin, biotin, or avidin. In some examples, attaching the proteins in the array of proteins of interest to a solid or semisolid surface comprises covalently linking the proteins to the solid or semisolid surface. For examples, the solid or semisolid surface comprises an amine-terminated polyethylene glycol [HS—$C_{11}$ $(C_2H_4O)_6$—$NH_2$], alkanes and glycols of varying lengths, or a mixture of amine-terminated and non-amine-terminated spacers. Further, in some examples, the amine-terminated polyethylene glycol monolayer covalently links a poly-L-lysine polymer and capture moiety to the surface using a reactive sulfo-NHS ester amine-to-amine crosslinker (BS3), which is activated at time of printing. In some examples, the capture moiety comprises a chloroalkane ligand and the proteins comprise a Halo-Tag. In additional examples, producing a set of proteins of interest using a cell-free protein expression system, comprises immobilizing plasmid cDNA on the solid substrate which is a slide and whereby the set of proteins are produced from the plasmid cDNA. In some examples, producing a set of proteins of interest includes using a cell-free protein expression system, comprises "cover capture" in which plasmid cDNA is printed within microwells on the solid substrate which is one slide, and wherein at the time of protein expression, the plasmid cDNA slide is sandwiched to a second slide pre-coated with capturing ligand, resulting in a separation of plasmid cDNA and expressed protein. In some examples, the plasmid DNA and expressed protein are within the same spot. For example, poly-L-lysine, or any other positively-charged polymer, is used to the attach plasmid cDNA to the slide surface. In some examples, the method further includes determining the affinity and/or binding kinetics of the targeting agent to one or more of the set of proteins of interest. For example, the targeting agent can comprise a protein, a nucleic acid, or a combination thereof.

The foregoing and other features and advantages of the disclosure will become more apparent from the following detailed description, which proceeds with reference to the accompanying figures.

BRIEF DESCRIPTION OF DRAWINGS

FIG. 1A) NanoBRET methodology. FIG. 1B) Venn diagram depicting the number of known and novel interactions detected by NanoBRET. FIG. 1C) BTK-ETS1 and FIG. 1D) PI3K-MYC interactions detected by NanoBRET, where the negative control, in triplicate, lacked a HaloTagged target protein. NanoBRET response=(Test sample Signal/Noise)-(DMSO control Signal/Noise). *Amount for one downstream reaction.

FIG. 2A) NAPPA-SPRi methodology. FIG. 2B) NAPPA-SPRi reproducibility. Binding sensorgrams showing anti-TP53 antibody and activated RAC1 queries binding specifically to displayed TP53 and NP-JUN target proteins, respectively, across three slides. Data referenced to a non-binder, LIME1 target. FIG. 2C) Tyrosine-phosphorylated target proteins after expression, de-phosphorylation, and treatment with B cell lysate, as determined via fluorescent analyses using an anti-phosphotyrosine antibody. Fluorescent images were analyzed at the same settings.

FIG. 4A) Bar plots depicting the binding kinetics and affinities of NP- and LT-targets obtained with NAPPA-SPRi for the BTK, inactive RAC1 query, active RAC1 query, and active RHOA. For complete bar plots for all queries. FIG. 4B) Radial plot showing the relative change in on-rates, off-rates, and binding affinities in log 10 of PI3K interactions following lysate treatment.

FIG. 6A) BTK phosphorylates JUN. FIG. 6B) BTK phosphorylates ETS1. FIG. 6C) BTK phosphorylates BCL2. FIG. 6D) PI3K phosphorylates MYC at serine 62.

Figure 7:
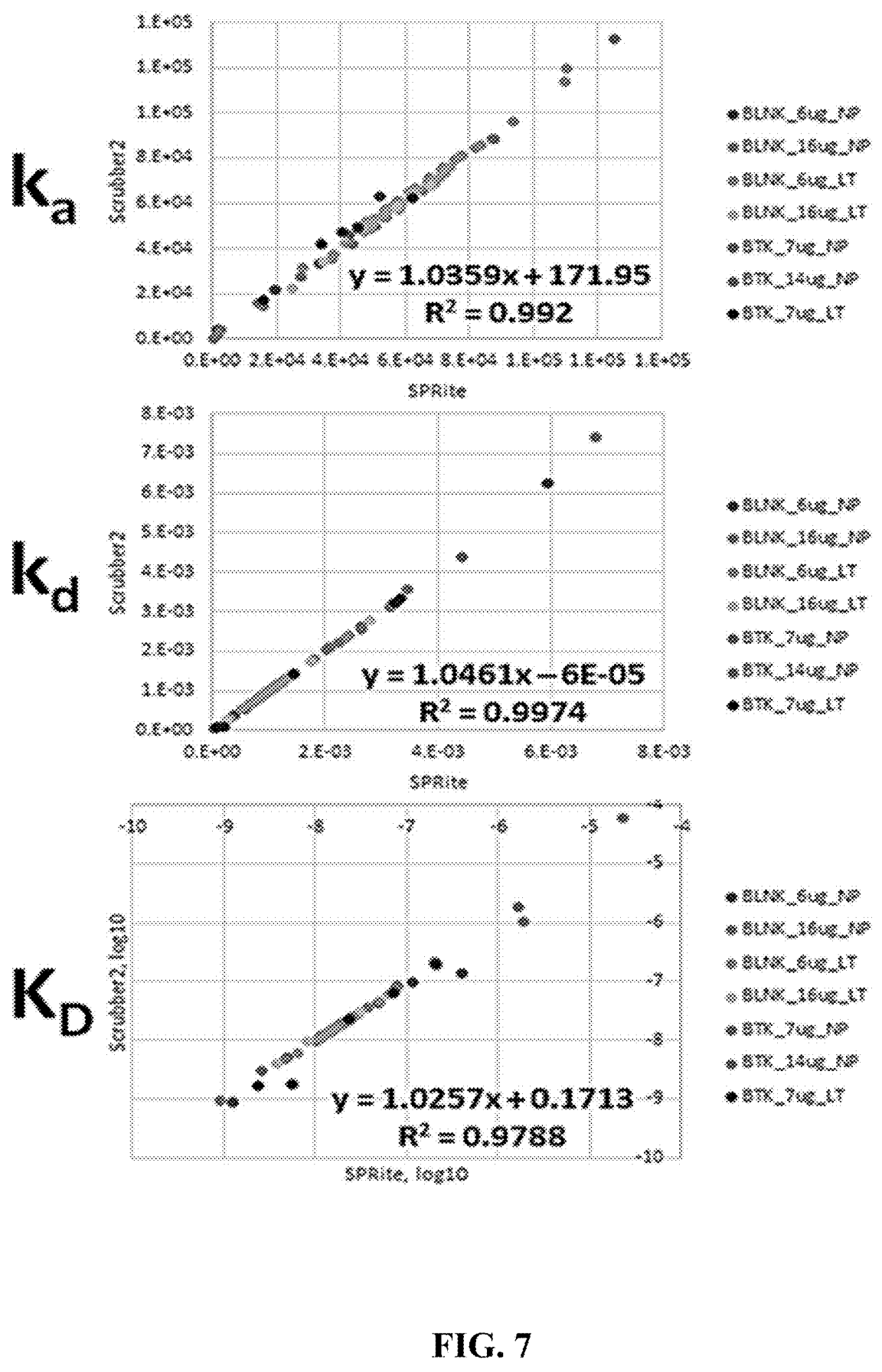

FIG. 7. Correlation of ka, kd, and KD values obtained with SPRite and Scrubber2 for seven datasets. All of the binding curves from one dataset and several binding curves representing a range of binding rates and affinities from six other datasets were analyzed with SPRite and Scrubber2. These 7 datasets were chosen because they came from multiple different experiments, they had a wide range of binding kinetics and affinities (i.e., ka=1.2×102 to 1.33×105 M−1s−1, kd=3.74×10−5 to 7.41×10−3 s−1, KD=8.97×10−10 to 6.0×10−5 M), were within the linear range of the instrument, did not have mass transport, the association response had some curvature, and the binding responses followed a single exponential.

FIG. 8. An example of a PDF output file of SPRite depicting the raw binding curve (light green), the referenced binding curve (black), the fitted curve (red), and the residuals between the fitted curve and referenced binding curve (blue). X-axis=time (sec). Y-axis=response units (RU). GTP-bound RHOA binding to NP-VAV1.

Figure 1A:
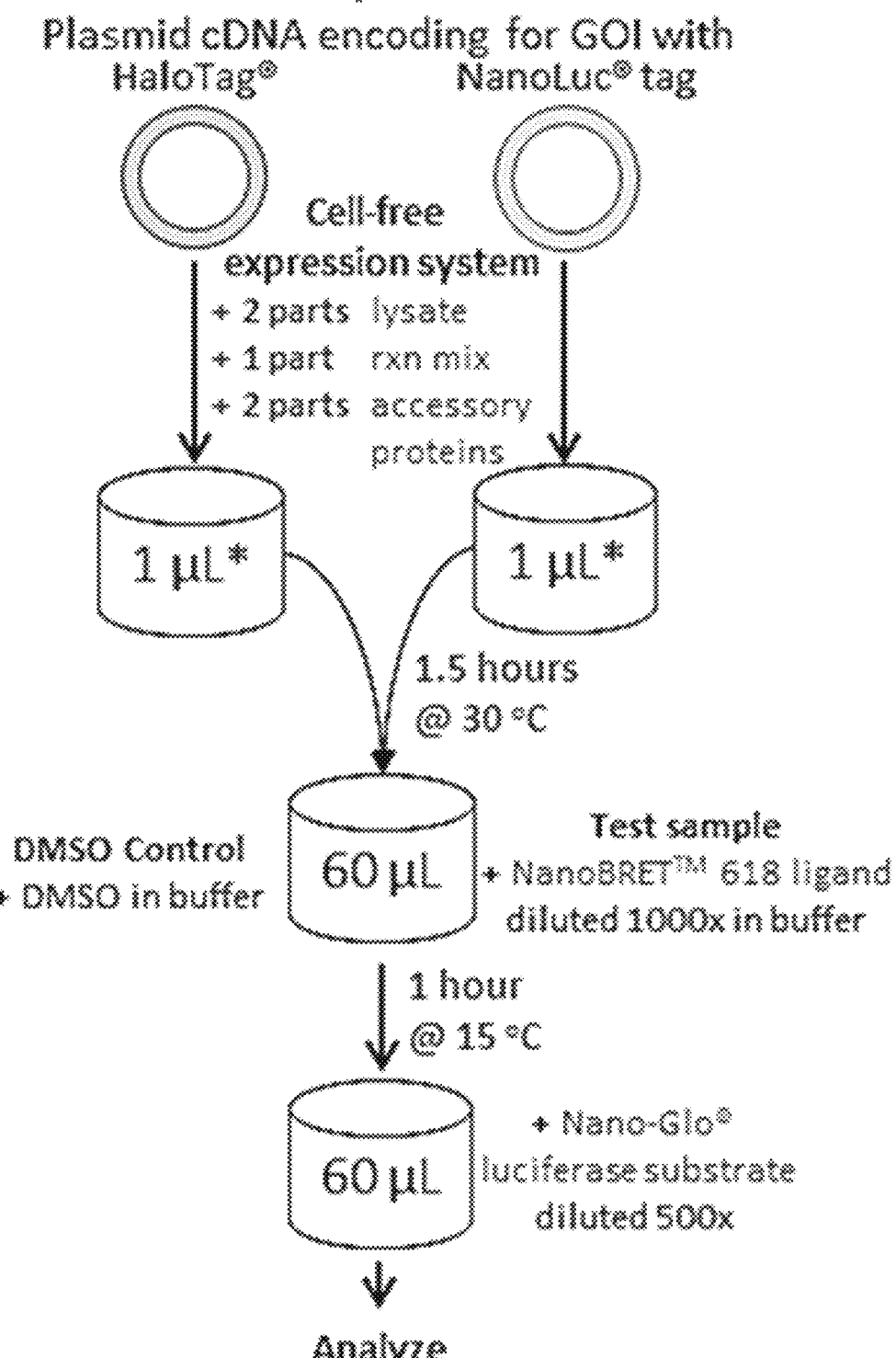
FIGS. 1A-1D. In vitro NanoBRET analysis of protein interactions using plasmid cDNA and cell-free expression system.

The foregoing and other features and advantages of the disclosure will become more apparent from the following detailed description, which proceeds with reference to the accompanying figures.

DETAILED DESCRIPTION OF SEVERAL EMBODIMENTS

This technology disclosed herein is described in one or more exemplary embodiments in the following description with reference to the Figures. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular forms "a," "an," and "the" are intended to include the plural forms as well, unless the context clearly indicates otherwise.

As used herein, the term "and/or" refers to and encompasses any and all possible combinations of one or more of the associated listed items, as well as the lack of combinations when interpreted in the alternative ("or").

As used herein, "one or more" or at least one can mean one, two, three, four, five, six, seven, eight, nine, ten or more, up to any number.

As used herein, the term "comprises" means "includes." Hence "comprising A or B" means including A, B, or A and B. It is further to be understood that all base sizes and all molecular weight or molecular mass values given for peptides and nucleic acids are approximate and are provided for description.

The term "contacting," as used herein, refers to placement in direct physical association. Contacting can occur in vitro with, e.g., samples, such as biological samples containing a target biomolecule, such as an antibody.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Although methods and materials similar or equivalent to those described herein can be used in the practice or testing of the present disclosure, suitable methods and materials are described below. All publications, patent applications, patents, and other references mentioned herein are incorporated by reference in their entirety. All GenBank accession numbers are hereby incorporated by reference as available on the world wide web as of Jun. 12, 2018. Unless otherwise defined, all technical terms used herein have the same meaning as commonly understood. Other methods and materials similar or equivalent to those described herein can be used. For example, conventional methods well known in the art to which this disclosure pertains are described in various general and more specific references, including, for example, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999. In addition, the materials, methods, and examples are illustrative only and not intended to be limiting.

A map of the human interactome is still incomplete. Approximately ~ 50% of the estimated 650,000 protein-protein interactions are currently annotated in the Biological General Repository for Interaction Datasets (BioGRID) database (Stark et al., 2006; Stumpf et al., 2008). It is probable that the coverage is much less since this estimate does not take into account multiple splice variants and is based on experiments that are biased and uninformative. For example, equilibrium-based assays that are commonly employed to study protein interactions generally detect interactions with high binding affinities, thereby missing transient interactions that underlie important cellular processes. Interactions with moderate-to high-abundance proteins in vivo are favored by detection methods over low-abundance proteins. Post-translational modifications (PTMs) and protein activation states can drastically affect interactions, yet very few studies document these characteristics. Finally, proteins involved in disease are studied more than proteins with unknown or poorly understood functions, in a process that can be tautological.

High throughput methods to study protein interactions, including affinity purification and yeast-two-hybrid, determine which proteins bind to each other. One such technology is the protein microarray, which displays hundreds to thousands of different proteins of known address on a solid planar or bead substrate. Traditional microarrays have relied on using purified proteins that were expressed in vivo using *Escherichia coli* (*E. coli*), yeast and baculovirus insect cells. The use of nonhomologous systems to express mammalian proteins can be problematic since they may not have the appropriate chaperones for proper folding or ability to attach PTMs. Even if a protein were to get post translationally modified, it is unlikely that the type and location of the PTM would reflect those occurring in native systems. The purification procedure is often low throughput regardless of the host system and requires additional protein manipulation that may negatively affect protein conformation and activity.

Nucleic acid programmable protein arrays (NAPPA) are a type of protein microarray where the proteins are produced in vitro using plasmid cDNA and a cell-free expression system. As such, the proteins are produced at the time of the experiment (<2 hours) in an appropriately-matched expression system with native ribosomes and chaperone proteins to ensure proper protein folding and activity. Standard protein purification methods are unnecessary since fusion tagged proteins are captured in situ to the slide surface using an anti-tag ligand. Moreover, any protein can be synthesized as long as the plasmid can be constructed. NAPPA has been used to identify antibody biomarkers of disease, screen drugs, and study protein interactions.

High throughput methods for studying protein-protein interactions provide valuable information on which proteins interact, yet they have two major drawbacks. First, they often rely on detecting stable complexes that can withstand multiple wash steps, thereby missing more prevalent transient interactions. Second, they cannot characterize interactions quantitatively in regards to how quickly they associate and dissociate from each other (i.e., kinetics) and their binding strength (i.e., affinity). The binding affinity, or dissociation constant $K_D$, is generally described as the fraction of unbound proteins to bound proteins (i.e., [A][B]/[AB]) at equilibrium. $K_D$ can also be represented by the dissociation rate, ka, divided by the association rate, $k_a$. The binding kinetics and affinities determine the temporal regulation of signal; in other words, which proteins can outcompete for the same binding partner and the length of signal(s).

Several methods can determine binding kinetics and/or affinities, including isothermal titration calorimetry, microscale thermophoresis, and surface plasmon resonance (SPR). However, these low throughput methods have resulted in a paucity of quantified protein interactions. The B cell receptor signaling pathway, for example, is comprised of >100 proteins and possibly>$2^{100}$ interactions, yet only 12 interactions have been characterized quantitatively.

In SPR, a single protein interaction between a displayed protein (i.e., ligand or target) and an injected protein under flow (i.e., analyte or query) is detected in real-time using a flow chamber, light source, and light detector in a 1:1:1 ratio. SPR can therefore be multiplexed by increasing the number of flow chambers, light sources and detectors in tandem. The most common platform is the Biacore T100 instrument, which allows up to four different protein interactions to be analyzed simultaneously.

SPR imaging (SPRi) is an array format of SPR where only one light source and one detector are needed. SPRi has the capacity of analyzing any type of protein interaction in a high throughput manner, yet most SPRi studies rely on antibody- or peptide-based interactions. Even proof-of-concept demonstrations of SPRi throughput have been based on numerous replicates of stable antibody-antigen interactions rather than more biologically-relevant, non-antibody interactions. In actuality, only one study has examined the kinetics of nonantibody, full-length proteins in high throughput. Prior to the present disclosure, there is no technique that can analyze the binding kinetics and affinities of protein interactions in a high throughput manner.

The systems and methods disclosed herein combine the high throughput and flexible nature of NAPPA with the quantitative platform SPRi to analyze the binding kinetics and affinities of more than 400 different protein interactions simultaneously in less than 1 hour. Moreover, modifications to the displayed proteins can be made, thus enabling high throughput studies of PTMs and their effects on protein interactions. These modifications, which have been performed using standard NAPPA or NAPPA-SPRi, include phosphorylation, AMPylation, and citrullination. Other types of modifications could also be implemented; for example, protein glycosylation using specific glycosyltransferases during or after protein expression.

Dynamic protein interactions drive biological responses, yet no high throughput platform quantitatively characterizes their binding kinetics and affinities. A large-scale kinetic analysis of >12,000 potential protein interactions in the B cell receptor (BCR) signaling pathway using NAPPA-SPRi under altered protein phosphorylation and GTPase activation states was disclosed. Approximately 500 interactions were detected with 84% previously undocumented, including the phosphorylation of proteins essential in homeostasis and disease. These data reveal that phosphorylation modulates the binding kinetics for >80% of interactions, and that GTPase activation imparts competitive advantage in signal transduction by increasing binding kinetics and/or partners. Finally, the utility of studying protein interactions with various modifications (i.e., unphosphorylated versus phosphorylated) was demonstrated. Novel phosphorylation-mediated interactions involving proteins essential in homeostasis and disease identified with NAPPA-SPRi were validated using SDS-PAGE and Western blot analyses.

The technology and methodology described here can be used to study any interaction or signaling pathway as long as the plasmid cDNA can be constructed. NAPPA-SPRi has broad applications in basic, translational, and clinical research. Interactomes of different signaling pathways, cell types, and species can be qualitatively and quantitatively mapped. The hybrid platform could also study host-pathogen protein-protein interactions and the effect of protein mutations on protein interactions. NAPPA-SPRi could also screen antibody analytes in high throughput for nonspecific binding. Notably, the calculated binding kinetics and affinities of antibody analytes (rather than ligands) would not be accurate due to the effect of avidity.

The disclosed NAPPA-SPRi is the first SPRi platform to use a cell-free expression system to produce greater than 400 different proteins on one array for real-time kinetic analyses of greater than 400 different protein interactions. It is also believed to be the first time PTMs of the displayed proteins has been performed on SPRi. More specifically, the surface chemistry and modifications to the displayed proteins are advantageous for at least the following reasons:

SPR self-assembled monolayer: amine-terminated polyethylene glycol [HS—C11 (C2H4O)6—NH2]. This encompasses alkanes and glycols of varying lengths, or a mixture of amine-terminated and non-amine-terminated spacers. The amine-terminated polyethylene glycol monolayer covalently links the poly-L-lysine polymer and HaloTag ligand to the surface using a reactive sulfo-NHS ester amine-to-amine crosslinker (BS3), which is activated at the time of printing. Prior to protein expression, any remaining active crosslinker ester group is inactivated with Tris. The standard monolayer with SPR terminates with a carboxyl group, which must be activated with EDC and NHS to covalently capture amines. While NAPPA-SPRi is possible with this chemistry, it is not ideal since the half-life of activated carboxyl groups is approximately 10 min whereas the printing that is used with NAPPA-SPRi can last for hours. Carboxyl activation followed by coating the slide with HaloTag ligand circumvents the issue with slow printing times; however, this results in a significant amount of diffused protein being captured outside of its designated printed spot and decreased signal.

Plasmid cDNA, from which the produced are produced. The plasmid DNA and expressed protein can be within the same spot on one slide. Another option is known as "cover capture" in which the plasmid cDNA is printed within microwells on one slide. At the time of expression, the DNA slide is sandwiched to another slide pre-coated with capturing ligand, resulting in a separation of plasmid cDNA and expressed protein. Standard protein microarrays generally use linear DNA because it can be covalently captured to a substrate in various ways. As disclosed herein, however, the inventors observed that linear DNA has lower expression efficiency than plasmid cDNA. Plasmid DNA is successfully immobilized on standard NAPPA slides when BSA was added to the printing mixture. Without being bound by a particular theory, it is believed that the BS3 crosslinks the BSA lysines to each other, forming a meshwork that theoretically holds the plasmid cDNA in place. The use of plasmid cDNA is thus a unique attribute of NAPPA and, as an extension, NAPPA-SPRi.

Poly-L-lysine, or any other positively-charged polymer, to capture the DNA to the slide surface. SPR and SPRi do not detect protein interactions per say. Instead, these technologies detect local refractive index changes that occur above the gold surface during a protein interaction. Thus, a desired surface chemistry is low in mass while the injected query is high in mass, resulting in a high signal-to-noise ratio. For this reason, standard NAPPA chemistry, which has a lot of mass (i.e., 183 μg of reagents per 30 μL of printing mixture), is not compatible with SPR or SPRi since the signal-to-noise ratio is less than 1. To make NAPPA compatible with SPRi, the mass of the printing mixture had to be decreased significantly. This was accomplished in two primary ways. The first was to replace the GST fusion tag with HaloTag, which enabled the capturing ligand to be switched from a bulky 150 kDa anti-GST antibody to a 400 Da chloroalkane ligand. The second was to use a poly-L lysine polymer instead of BSA. BSA is 66 kDa with greater than 90% of its mass theoretically useless whereas 100% of the poly-L-lysine residues can be used. In short, the printing master mix was changed in the following ways: 1) different fusion tags and capturing reagents, 2) ratio of the reagents, and 3) the mass decreased 92%.

Non-EDC-NHS capture of displayed proteins. The disclosed chemistry uses HaloTagged fusion proteins, which are captured to the surface using the chloroalkane HaloTag ligand. HaloTag is a modified dehalogenase. More specifically, nucleophilic attack by Asp106 of wild-type *Rhodococcus rhodochrous* on the chloroalkane ligand removes the chloride and forms an ester bond. His272 then hydrolyzes the reaction, thus releasing the ligand from the enzyme. The histidine was replaced with phenylalanine, resulting in a stable covalent bond between the HaloTag protein and a chloroalkane substrate (England, Luo, & Cai, 2015). Other types of covalent protein capture could also be used, such as SNAP-, CLIP-, TMP-, ACP-, or MCP-tag chemistry. SNAP-tag is based on the interaction between 06-alkylguanine-DNA alkyltransferase and its benzylguanine substrates. CLIP-tag is based on the interaction between 06-alkylguanine-DNA alkyltransferase and its 02-benzylcytosine substrates. TMP-tag is based on the interaction between dihydrofolate reductase and its trimethoprim substrate. ACP-tag is based on the interaction between the acyl carrier protein and Coenzyme A (in the presence of a synthase). It is contemplated that other covalent tags could be implemented based on the biology (or mutation) of other types of enzymes. It is also contemplated that 3D surface chemistry, like a carboxymethylated dextran matrix, can be implemented successfully with NAPPA-SPRi using a combination of EDC-NHS capture of tag ligands and the contra capture approach (Karthikeyan et al., 2016). For example, the contra capture approach, described in more detail in the Example section has been successfully applied with standard NAPPA.

De-phosphorylation of produced proteins (since the expression system has phosphorylation capability) using calf intestinal alkaline phosphatase and lambda protein phosphatase. The human cell-free expression system is based on the HeLa cervical cancer cell line. It has phosphorylation capability. However, some users may not want a HeLa-specific phosphorylation profile or may want to control the phosphorylation status of the target proteins. For example, the user may wish to determine the phosphorylation substrates of a kinase. Therefore, the array proteins were de-phosphorylated using phosphatases. The number of phosphatases were kept to a minimum while maximizing protein de-phosphorylation across all substrates. A design of experiments (DOE) approach was used to determine the optimal amount of lambda protein phosphatase and calf intestinal alkaline phosphatase, incubation length, and number of incubations for de-phosphorylating the array proteins. It was observed that 1) the phosphatases cannot be incubated together and that 2) the number of incubations with lambda protein phosphatase rather than the amount of phosphatase was more important. In some embodiments, the standard buffer (i.e., 50 mM potassium acetate, 20 mM tris-acetate, 10 mM magnesium acetate, 100 µg/mL BSA, pH 7.9) that comes with the calf intestinal alkaline phosphatase from New England BioLabs is not used. Instead, this phosphatase is incubated with 50 mM Tris pH 7.9, 100 mM NaCl, 10 mM MgCl2, 1 mM DTT. The array proteins are incubated once for 30 min at 30° C. with calf intestinal phosphatase and then incubated three times at 30° C. for 30 min with lambda protein phosphatase in 50 mM HEPES pH 7.5, 100 mM NaCl, 2 mM DTT, 0.01% Brij 35, 1 mM MnCl2. It is believed that prior to the present disclosure, there are no SPR disclosures in which target proteins are de-phosphorylated or the use of both phosphatases with protein microarrays.

Phosphorylation of proteins in cell-specific manner using lysate (from the cell-of-interest) with protease and phosphatase inhibitors. Users may not want HeLa-specific phosphorylation. In a study using NAPPA-SPRi, protein interactions in the B cell receptor signaling pathway was characterized with altered phosphorylation states since kinase cascades are an important mechanism to propagate signal. One-half of the studies examined interactions with de-phosphorylated proteins, while the other half was interested in characterizing interactions with B cell-specific phosphorylation. Lysate from actively proliferating B cells was supplemented with protease and phosphatase inhibitors and incubated with de-phosphorylated array proteins for 3 hours at 30° C. Using an anti-phospho tyrosine antibody, distinct differences in phosphorylation by the HeLa expression system and the B cell lysate were observed. Notably, anti-phospho serine and threonine antibodies cannot be used to screen for global phosphorylation as these antibodies are usually specific to the phosphosite and the surrounding residues. No other SPR or microarray platform has done this before. The disclosed re-phosphorylation approach could be used with lysates from any cell-of-interest as long as enough cells could be prepared. With the tested B cells, good phosphorylation (for one array) with lysate from approximately 1 million cells was obtained. While many different protease and phosphatase inhibitors were added to the lysate, the addition of commercially-available protease and phosphatase inhibitor tablets could be used instead. As such, the disclosed methods and systems are advantageous for at least the aforementioned reasons.

The following examples are provided to illustrate certain particular features and/or embodiments. These examples should not be construed to limit the disclosure to the particular features or embodiments described.

EXAMPLE

Analyses of Protein Interactions in the B Cell Receptor Signaling Pathway

This example provides analyses of protein interactions in the B cell receptor signaling pathway.

To understand the extent of the annotated human interactome, we first examined greater than 2500 binary protein interactions within the B cell receptor (BCR) signaling pathway using a current, cutting-edge bioluminescence-based platform called "NanoBRET™" that is capable of analyzing transient and stable interactions in high throughput (Machleidt et al., 2015). Eighty-three percent (83%) of the detected interactions have not been previously reported, indicating that much of the BCR pathway is still unexplored. Unfortunately, NanoBRET, as with all other high throughput methods, cannot determine binding kinetics or affinities. To address this shortcoming, we developed a hybrid platform that characterizes>greater than 400 protein interactions quantitatively and simultaneously in less than 1 hour by combining the high throughput and flexible nature of nucleic programmable protein arrays (NAPPA) with the quantitative abilities of surface plasmon resonance imaging (SPRi). NAPPA-SPRi was used to study the kinetics and affinities of greater than 12,000 protein interactions in the BCR signaling pathway under altered phosphorylation and activation states, revealing unique kinetic mechanisms that are employed by proteins to regulate proteins. The methods and technology disclosed herein can be applied toward characterizing other signaling pathways or networks, which will facilitate an understanding of the biological regulation of protein interactions and streamline drug development.

Selection of BCR Signaling Pathway Proteins for Analyses

Proteins in the BCR signaling pathway selected for interaction analyses were identified by the Kyoto Encyclopedia of Genes and Genomes (KEGG) and Human Protein Reference Database (HPRD), resulting in 109 proteins in the dataset. These included adaptor proteins, serine/threonine kinases, tyrosine kinases, phosphatase, GTPases, cell surface receptors, guanine nucleotide exchange factors (GEFs), a phospholipase, transcription factors, and regulatory proteins. A subset of this BCR pathway protein set was also employed as query proteins in our analyses because they occur at key nodes in the BCR pathway, are important regulators of B cell response, and immunodeficiencies and cancers are associated with their altered activity from mutations or overexpression. These purified queries, which were proven to be functional through kinase or interaction assays, included the adaptor protein BLNK, tyrosine kinase BTK, lipid and serine/threonine kinase PI3K, Rho GTPase RAC1, and Rho GTPase RHOA. Notably, the PI3K query was a heterodimer, containing the alpha isoforms of both the regulatory subunit PIK3R1 and the catalytic subunit PIK3CA. These isoforms were chosen because, unlike the other isoforms, they are ubiquitously expressed. Moreover, PIK3CA is the only catalytic isoform that is frequently mutated in cancer, while PIK3R1 is the most frequently mutated regulatory subunit in cancer (Herrero-Gonzalez & Di Cristofano, 2011; Zhao et al., 2006). The ability to test different protein types also provided insight into their unique methods of regulation. Inclusion of RAC1 and RHOA presented an opportunity to compare the binding partners and kinetic profiles of active and inactive GTPases. Obtaining functional and purified recombinant proteins was not a consideration with NanoBRET as it was with NAPPA-SPRi since the NanoBRET proteins are produced in vitro using a mammalian expression system without the need for purification. Thus, an additional five queries important in B cell regulation were studied with NanoBRET: serine/threonine kinase AKT1, adaptor DAPP1, tyrosine kinase LYN, serine/threonine kinase MAPK14 (i.e., p38), and tyrosine kinase SYK. Further detail about these query proteins are in Supplemental Information which is provided herein.

83% of Interactions Detected by NanoBRET have not been Previously Reported

The human interactome has been studied primarily through methods that rely on stable and transient protein interactions, focusing on proteins with known function. Therefore, we wondered: how much of the interactome has been missed? To help answer this question, we adapted a current, high throughput method capable of detecting transient and stable interactions in vivo, Promega Corporation's NanoBRET™, to analyze more than 2500 protein interactions in the BCR signaling pathway using proteins produced in vitro using a human cell-free expression system (FIG. 1A). NanoBRET has numerous advantages compared to standard bioluminescence resonance energy transfer (BRET). These advantages include maintaining its luciferase activity at physiological pH and over a wider temperature range; using a smaller luciferase to minimize its interference with the native protein function; producing high intensity, "glow-type" luminescence that has a signal half-life of more than 2 hours; and having a higher sensitivity and dynamic range (Hall et al., 2012; Machleidt et al., 2015).

Figure 1B:
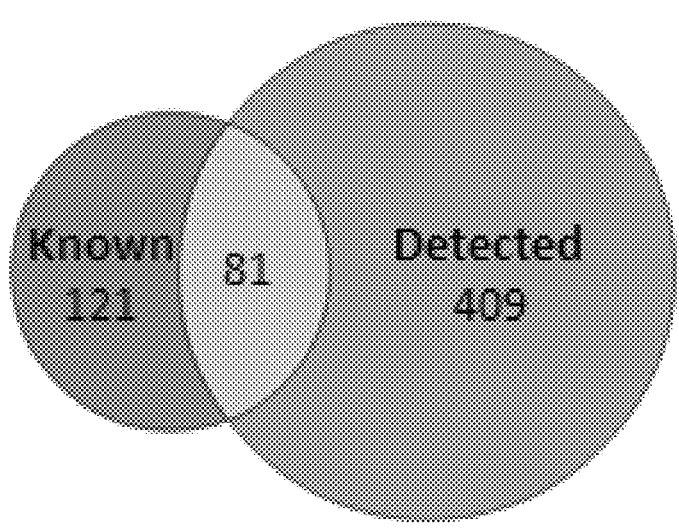
Figure 1C:
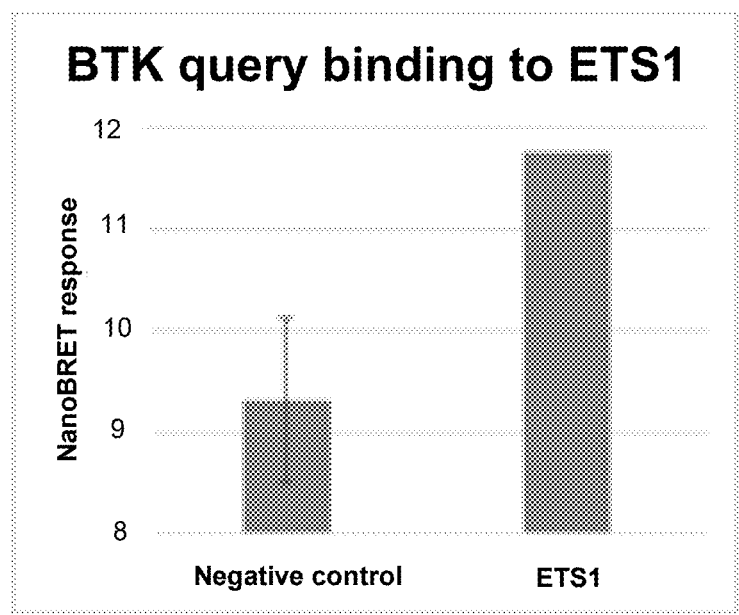
Figure 1D:
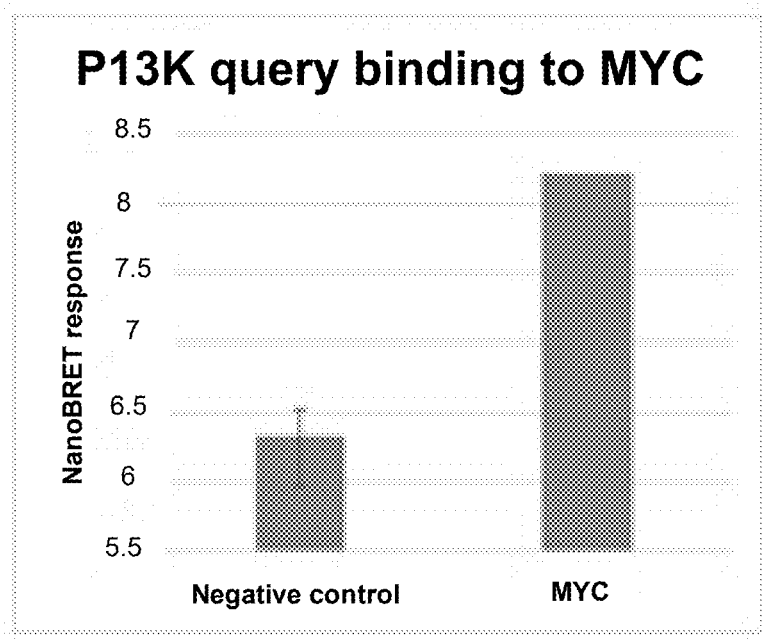

In our study, the binary interactions of 12 N-terminal luciferase-tagged query proteins against the N- and C-terminal fluorophore-tagged BCR pathway protein set were tested. To determine the number of known and novel interactions detected with NanoBRET, the data were compared to the online protein interaction databases, BioGRID and the Human Protein Reference Database (HPRD) (Prasad et al., 2009; Stark et al., 2006). NanoBRET detected ~ 40% (81/202) of known interactions across all twelve queries (FIG. 1B). Approximately 60% of previously-reported interactions not identified by NanoBRET may be due to false positives, different experimental conditions, or the blocking of binding epitopes by the fusion tags. Eight-three percent (83%; 409/490) of the interactions detected by NanoBRET have not been reported previously (FIGS. 1C-1D), indicating that much of the BCR pathway is still unexplored.

Unfortunately, NanoBRET, just like any other high throughput method, cannot characterize protein interactions in regards to their binding kinetics and affinities. This type of quantitative information provides a more time-resolved picture of signal transduction, particularly for predictive algorithms or steady state models. In addition, a human Hela cell-based in vitro transcription translation (IVTT) system capable of phosphorylating proteins was used to express the proteins used for NanoBRET analysis. Thus, the detected interactions may only reflect those that occur (or not occur) in HeLa cells.

Development of a High Throughput Kinetic Analysis Platform, NAPPA-SPRi

Protein binding kinetics and affinities have thus far been determined in low throughput due to limitations of current technologies. SPR and isothermal calorimetry, for example, can only analyze one protein interaction at a time within a single analysis chamber. SPR in an array format called SPR imaging (SPRi) has the potential to characterize protein interactions in high throughput, yet has traditionally investigated only a handful of different protein interactions at a time due to the tedious process of expressing and purifying the proteins displayed on the array (i.e., targets) and the queries that probe them.

Figure 2A:
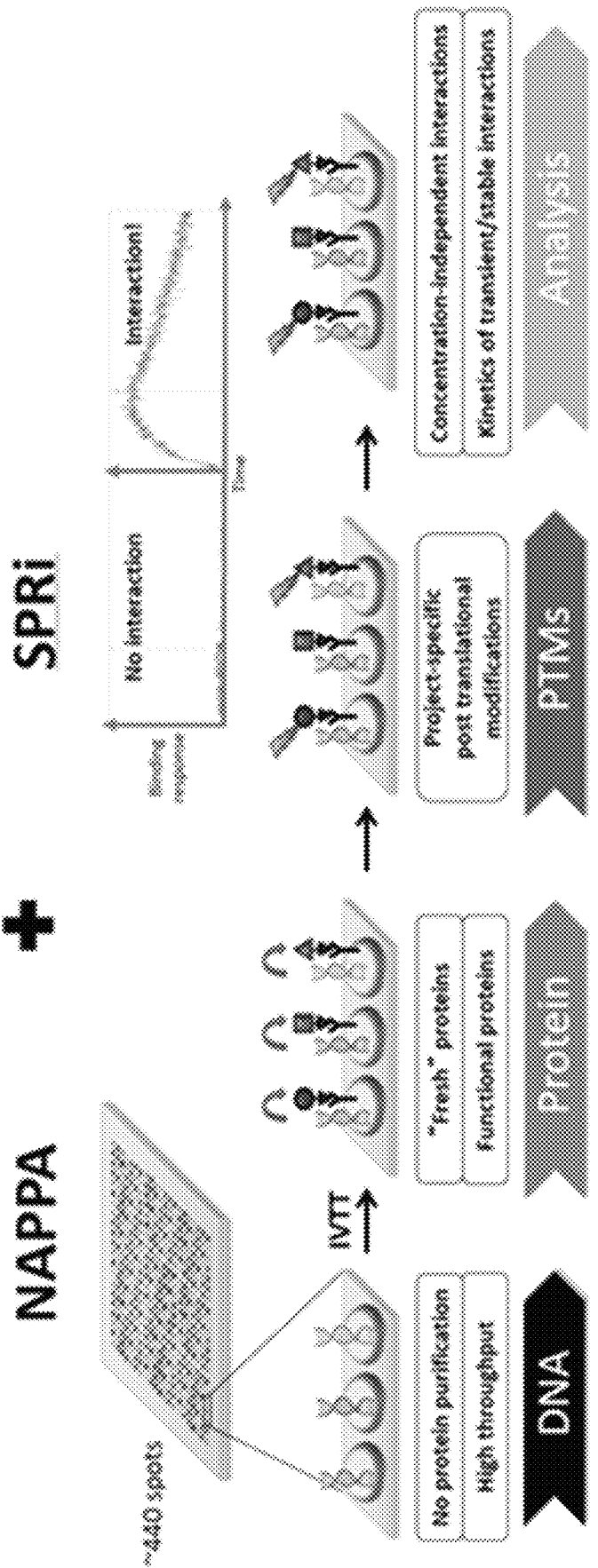
FIGS. 2A-2C. NAPPA-SPRi is compatible with SPRi.

Our laboratory developed the nucleic acid programmable protein array (NAPPA), in which plasmid cDNA encoding for any protein-of-interest is spotted onto a glass surface and then transcribed and translated by an in vitro expression system (i.e., *Escherichia coli*, rabbit, insect, human, wheat germ) at the time of the experiment (Ramachandran et al., 2004; Ramachandran et al., 2008; X. Yu, Petritis, Duan, Xu, & LaBaer, 2018). No purification is needed since the tagged proteins-of-interest are captured to the slide in situ via an anti-tag reagent (e.g., GST tag, anti-GST antibody) (FIG. 2A). Moreover, proteins are produced with homologous ribosomes and chaperones, increasing the likelihood that the proteins are folded properly and are functional. Several experiments have demonstrated that NAPPA proteins are functional with inter- and intra-slide reproducibility $R^2>0.95$ (Ramachandran et al., 2004; Ramachandran et al., 2008; Rauf et al., 2018; X. B. Yu & LaBaer, 2015). Moreover, cell-free expression enables the production of proteins that would be otherwise toxic to cells; the incorporation of non-natural amino acids; and the addition of additives, detergents, cofactors, and binding partners. Finally, the fusion tag minimizes substrate-induced denaturation by distancing the protein-of-interest from the substrate surface (Karlsson, Ekeroth, Elwing, & Carlsson, 2005). As many as 2,300 different proteins can be expressed on a standard glass microscope slide using a pin spotter.

Figure 2B:
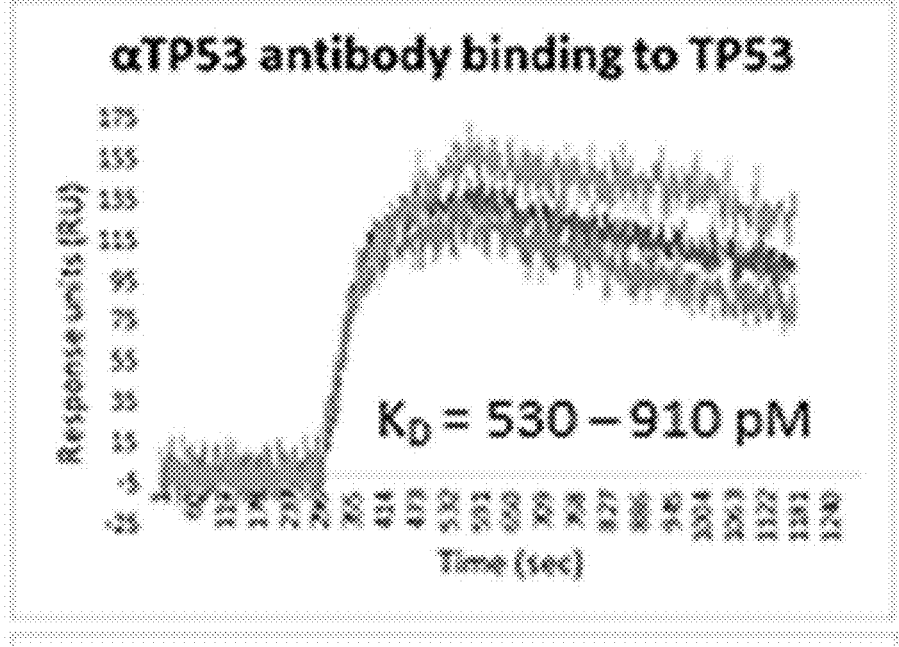
Figure 2B:
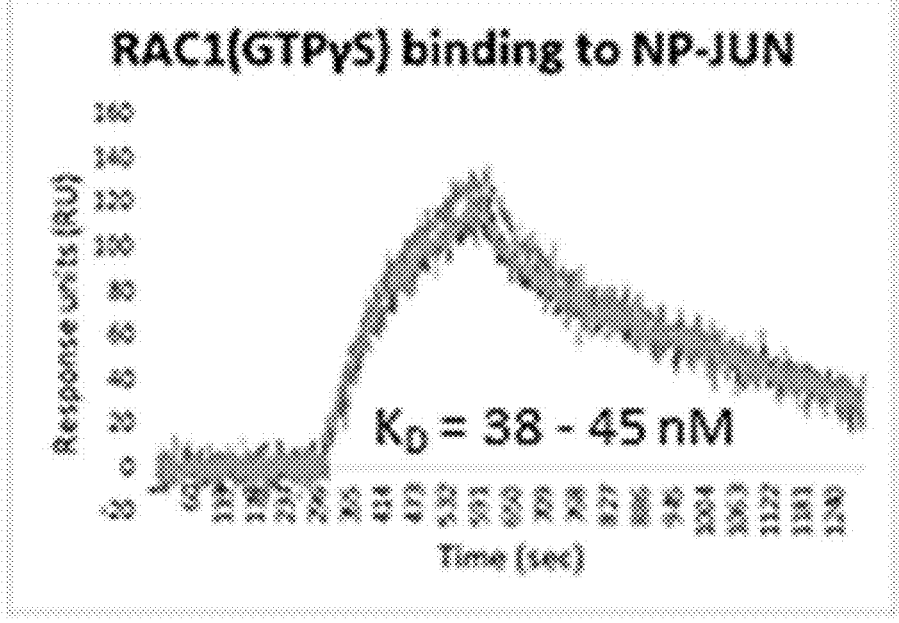

We therefore wanted to determine whether the NAPPA chemistry could be successfully applied toward SPRi to create a high throughput, hybrid technology capable of analyzing binding kinetics and affinities in real-time. Using a pin spotter, 441 spots with a 450 μm diameter spaced 640 μm apart (center-to-center) were applied within the 14 mm×14 mm detection window of the SPRi instrument. Unfortunately, the high mass of the standard NAPPA printing mixture masked the binding signal involving a query protein with considerably lower mass. The mixture contained plasmid cDNA, an amine-to-amine crosslinker, an anti-GST antibody, and bovine serum albumin (BSA). We therefore decreased the mass of the NAPPA printing mixture by 92%, which was achieved largely by changing protein and DNA capturing reagents (i.e., antibody and BSA, respectively). First, the 150 kDa anti-GST antibody used to capture the GST-fusion protein was exchanged for a 400 Da chloroalkane ligand that binds to HaloTag®. The use of HaloTag had additional advantages over GST. The HaloTag-chloroalkane interaction is covalent whereas the non-covalent GST-anti-GST antibody interaction will result in target loss under sample flow (England, Luo, & Cai, 2015). In addition, NAPPA is only compatible with GST tags at the C-terminus. Since some epitopes on the displayed proteins may be blocked by a fusion tag, it would be advantageous to have the displayed proteins represented separately on the array with the tag at the N- and C-terminus. Proteins with HaloTag at the N- and C-terminus can be successfully captured to the NAPPA surface (Wang et al., 2013). Second, the DNA capturing reagent, BSA, was exchanged for poly (L-lysine), a positively-charged amino acid polymer of lysines. Without BSA, the plasmid cDNA is not retained on the slide. BSA is believed to essentially form a meshwork— in which the DNA is captured-through its lysine residues and the aminosilane-coated surface via the amine-to-amine crosslinker. Since<10% of BSA's mass is lysines, >90% of its mass is unnecessary whereas 100% of the poly(L-lysine) residues would theoretically be useful. The 92% decrease in NAPPA printing mass enabled the detection of protein binding with SPRi (FIG. 2B).

Figure 2C:
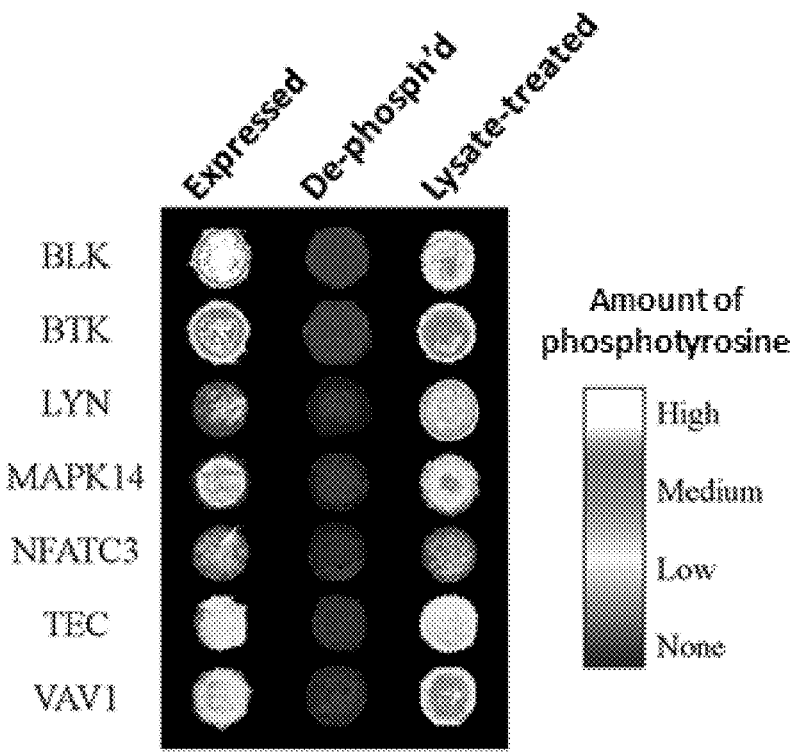

De-Phosphorylation and B Cell-Specific Phosphorylation of Target Proteins Displayed on NAPPA-SPRi Phosphorylation is used as a major mechanism of signal transduction for the BCR signaling pathway and is generally considered to be a post translational modification of positive regulation. Therefore, the study of protein interactions within the BCR signaling pathway should consider interactions with and without phosphorylation. Because the in vitro transcription and translation system can phosphorylate the expressed proteins, the target proteins were de-phosphorylated using calf intestinal alkaline phosphatase and lambda protein phosphatase (hereafter referred as "not phosphorylated" or "NP"") (FIG. 2C).

The human expression system used in this study is based on HeLa cervical cancer cells, and likely phosphorylates the target proteins in a HeLa-specific manner. We therefore wondered whether the phosphorylation pattern generated by the expression system would differ from that obtained with lysate from activated B cells. After de-phosphorylating the targets as described above, they were incubated with lysate from actively proliferating Ramos RA-1 B cells containing kinase cofactors and phosphatase inhibitors. Target phosphorylation following expression and B cell lysate incubation was then compared fluorescently using an anti-phosphotyrosine antibody and fluorescently-labeled secondary antibody. The data reveal that the B cell lysate contains active kinases and that the phosphorylation pattern caused by these two conditions are indeed different (FIG. 2C). Note that LYN, a tyrosine kinase known to be tyrosine phosphorylated in B cells, was phosphorylated on the lysate-treated array. Moreover, VAV1, which is tyrosine-phosphorylated in activated B cells by SYK, was also phosphorylated by the B cell lysate.

Interactions with targets of mixed phosphorylation levels will complicate analyses and will not allow the direct comparison of the NAPPA-SPRi datasets. Protein interactions in the BCR signaling pathway were therefore analyzed with NAPPA-SPRi using de-phosphorylated and B cell lysate-treated target proteins (hereafter referred as "phosphorylated," "lysate-treated," or "LT"). It should be noted that certain target proteins may not be phosphorylated by the lysate and that the sites of the phosphorylation, if they do occur, are unknown.

Relative Binding Kinetics and Affinities were Obtained with NAPPA-SPRi

Standard SPR experiments generally use five to seven different concentrations of the query spanning as much as seven orders of magnitude to obtain absolute binding kinetics. These types of experiments are made possible through a cost-effective approach of regenerating the slide surface (i.e., removing residual query proteins) with acidic, basic, or high salt buffers after each query concentration. Regeneration is ideal for immobilized molecules (e.g., peptides, antibodies) that are stable when exposed to regeneration conditions. As such, regeneration was not performed in our NAPPA-SPRi experiments out of concern that regeneration may negatively affect protein structure, interactions and binding kinetics of some or all of the proteins in the BCR pathway proteins. "One-cycle kinetics" in which the query is added to the surface in increasing concentrations without regeneration is not compatible with NAPPA-SPRi due to the low amount of target protein displayed. To keep the experimental costs within budget, the interactions between seven queries (BLNK, BTK, PI3K, GDP-bound RAC1, GTPγS-bound RAC1, GDP-bound RHOA, GTPYS-bound RHOA) at two different concentrations with NP and LT targets composing the BCR pathway protein set were tested for a total of >12,000 protein interactions. Of note, the kinetic values obtained in this experiment are relative to each other since only two query concentrations were used.

Since SPR has remained a low throughput technology, current SPR software was built to calculate the binding kinetics and affinities from only a handful of binding curves at a time (e.g., Scrubber2, BIAevaluation). Accordingly, no software could handle the amount of data produced by NAPPA-SPRi. To address this issue, we created "SPRite," a Python script that can analyze high throughput SPR data in an automated fashion. A comparison of data across seven datasets with Scrubber2 reveals $R^2$ correlations of 0.992, 0.9974, and 0.9788 for ka, ka, and $K_D$, respectively.

Figure 3A:
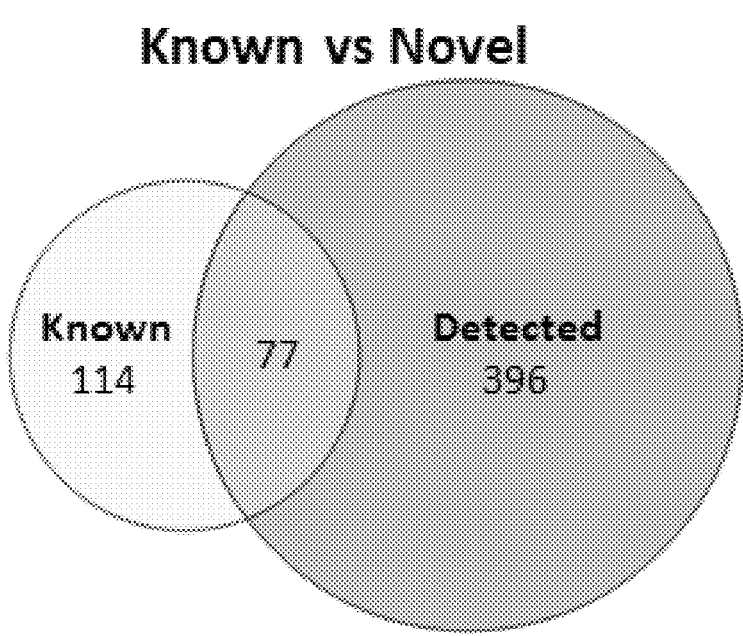
FIGS. 3A-3D. Venn diagrams of NAPPA-SPRi interactions. Protein interactions detected by NAPPA-SPRi FIG. 3A) that were also previously reported, FIG. 3B) that were also detected in this study by NanoBRET, with FIGS. 3C-3D) inactive and active RACI and RHOA with all targets, NP-targets, and LT-targets.

To evaluate how many known interactions were detected with NAPPA-SPRi, the data were compared to human, mouse, and rat protein interactions curated by BioGRID and HPRD (Prasad et al., 2009; Stark et al., 2006). Fifteen percent (16%; 77) of the detected interactions were known, representing 68% of the complexes listed in these sources for all seven queries (FIG. 3A). The majority of the interactions detected by NAPPA-SPRi (i.e., 84%; 396) were previously unreported.

Figure 3B:
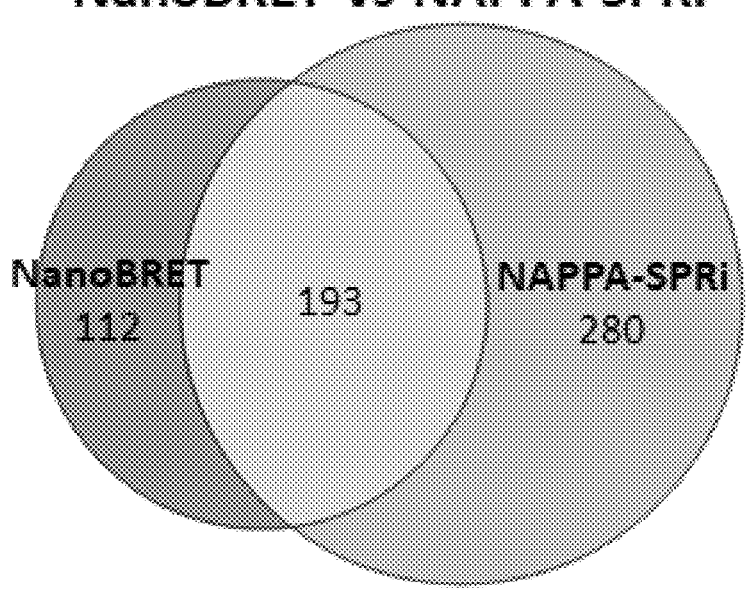

Protein interactions identified with NAPPA-SPRi were compared with those obtained with NanoBRET using the same seven queries. Forty-one percent (41%; 193/473) of all interactions and 42% (167/396) of the novel interactions detected with NAPPA-SPRi were also detected with Nano-BRET (FIG. 3B). Moreover, NAPPA-SPRi detected 55% more interactions than NanoBRET (i.e., 473 versus 305, respectively).

Phosphorylation Modulated Binding Kinetics and Affinities for 84% of the Interactions Phosphorylation is a posttranslational modification (PTM) in which a phosphate is covalently bound to a serine, threonine, or tyrosine residue by kinases and removed by phosphatases. It is estimated that one-third of all proteins within a cell are phosphorylated at any given time, playing important roles in intracellular signaling and metabolic control (Kitchen, Saunders, & Warwicker, 2008). Phosphorylation can affect protein interactions by altering protein structure, blocking binding sites, creating new binding epitopes, or causing bulk electrostatic changes that are sensitive to the subcellular location (Nishi, Shaytan, & Panchenko, 2014; Serber & Ferrell, 2007). As such, phosphorylation has been traditionally viewed as a PTM that modulates protein activity, binding kinetics, and binding specificity.

Eighty-four percent (84%) of the interactions detected by NAPPA-SPRi occurred with both NP- and LT-targets (Tables below).

Percentage of known and novel interactions detected by NAPPA-SPRi.

| Detected PPIs | BLNK | | BTK | | PI3K | | RAC1(GDP) | | RAC1(GTP) | | RHOA(GDP) | | RHOA(GTP) | |
|---|---|---|---|---|---|---|---|---|---|---|---|---|---|---|
| | NP | LT | NP | LT | NP | LT | NP | LT | NP | LT | NP | LT | NP | LT |
| All | 54 | 53 | 78 | 81 | 34 | 16 | 59 | 67 | 95 | 78 | 35 | 5 | 91 | 72 |
| % Known* | 17 | 19 | 13 | 11 | 35 | 31 | 15 | 15 | 14 | 17 | 17 | 20 | 15 | 15 |
| % Novel | 83 | 81 | 87 | 89 | 65 | 69 | 85 | 85 | 86 | 83 | 83 | 80 | 85 | 85 |

*Known human, mouse, or rat PPIs in the online databases, BioGRID and HPRD

PPI = protein-protein interaction

NAPPA-SPRi detected 68% of known protein interactions.

| Type of PPI | BLNK | | | BTK | | | PI3K | | | RAC1(GDP) | | |
|---|---|---|---|---|---|---|---|---|---|---|---|---|
| | All | NP | LT | All | NP | LT | All | NP | LT | All | NP | LT |
| Known PPI* | 15 | 15 | 15 | 14 | 14 | 14 | 27 | 27 | 27 | 15 | 15 | 15 |
| Known PPI/detected | 11 | 9 | 10 | 10 | 10 | 9 | 12 | 12 | 5 | 11 | 9 | 10 |
| Novel | 49 | 45 | 43 | 74 | 68 | 72 | 23 | 22 | 11 | 58 | 50 | 57 |
| % Known PPI detected | 73 | 60 | 67 | 71 | 71 | 64 | 44 | 44 | 19 | 73 | 60 | 67 |

| Type of PPI | RAC1(GTP) | | | RHOA(GDP) | | | RHOA(GTP) | | |
|---|---|---|---|---|---|---|---|---|---|
| | All | NP | LT | All | NP | LT | All | NP | LT |
| Known PPI* | 15 | 15 | 15 | 14 | 14 | 14 | 14 | 14 | 14 |
| Known PPI/detected | 13 | 13 | 13 | 6 | 6 | 1 | 14 | 14 | 11 |
| Novel | 82 | 82 | 65 | 29 | 29 | 4 | 81 | 77 | 61 |
| % Known PPI detected | 87 | 87 | 87 | 43 | 43 | 7 | 100 | 100 | 79 |

PPI = protein-protein interaction

Protein interactions detected by NAPPA-SPRi

| Protein | Isoform | BLNK | | BTK | | PI3K | | RAC1(GDP) | | RAC1(GTP) | | RHOA(GDP) | | RHOA(GTP) | |
|---|---|---|---|---|---|---|---|---|---|---|---|---|---|---|---|
| | | NP | LT | NP | LT | NP | LT | NP | LT | NP | LT | NP | LT | NP | LT |
| AKT1 | | C/N | C | N | N | [C] | [C/N] | | | [C] | [C] | C | C | C | C |
| AKT2 | BC063421 | C | C | C/N | C/N | N | | | C | C | C | C | | C | C |
| AKT2 | BC120994 | C | C | C/N | C/N | C | C | | | C | | C | | C | C |
| AKT3 | | | | C/N | N | | | C/N | C/N | C/N | C/N | | | C | C |
| ARHGEF7 | | | | N | C/N | | | | | | | | | N | N |
| BCL10 | | N | N | C/N | C/N | | | N | N | C/N | N | | | C/N | |
| BCL2 | | | | C/N | C/N | | | | | C | | | | N | |
| BCL2A1 | | C/N | C/N | C | C | C | C | | C | C/N | C | C | C | C | C |
| BCL2L1 | | N | C | C | C | | N | C | C | C | C | C | | C | C |
| BLK | | | | C | C | | N | | | C/N | | | | C | C |
| BLNK | | | | [C] | [C] | | | C | C | C | C | | | C | C |
| BTK | | | | [C] | [C] | | | | | | | | | C | C |
| CARD11 | | C | C | C | C | | | C | C | C/N | C | C | | C | C |
| CD19 | | | | C | C | | | C | C | C | C | | | C | C |
| CD22 | | C | C | C | C | C | | C | C | C/N | C/N | | | C | C |
| CD72 | | [C] | [C] | | | | | | | C/N | | C | | C | C |
| CD79A | | C/N | [C] | N | N | C | | | | C | | | | | |
| CD79B | | | C | N | N | | | | | C | C | | | C | |
| CD81 | | N | N | | | | | N | N | C/N | C/N | | | C/N | |
| CDC42 | | | | | N | | | | | N | | | | N | |
| CDKN2A | | N | C/N | | | | | N | N | C/N | C/N | | | N | |
| DAPP1 | | C | N | | | | | | | C/N | N | | | N | |
| EGR1 | | C | | | | | | | N | C/N | C/N | | | N | |
| ETS1 | | N | N | | C | N | N | N | N | C/N | C/N | C | | C/N | C |
| EZR | | | | C/N | C/N | | | N | N | N | N | | | [C/N] | [C] |
| FCGR2B | | | | C/N | C/N | | | | | C | | | | C | C |
| Fos | | | | N | N | | | | | C | C/N | C | | C | C |
| GRAP2 | | | | C/N | C/N | | | | | C | | | | | C |
| GRB2 | | [C/N] | [C/N] | [N] | [C/N] | | | [N] | [C/N] | [C/N] | [C/N] | C | | C/N | C/N |
| GSK3B | | | C | N | N | | | C | C | C | C | | | C/N | |

Protein interactions detected by NAPPA-SPRi

| Protein | Isoform | BLNK | | BTK | | PI3K | | RAC1(GDP) | | RAC1(GTP) | | RHOA(GDP) | | RHOA(GTP) | |
|---|---|---|---|---|---|---|---|---|---|---|---|---|---|---|---|
| | | NP | LT | NP | LT | NP | LT | NP | LT | NP | LT | NP | LT | NP | LT |
| HRAS | | C/N | C/N | C/N | N | [C/N] | | C/N | C/N | C/N | C/N | | | C/N | |
| IFITM1 | | | | C | C | | | | | | | | | C | C |
| IKBKA | | | N | C/N | C/N | N | | N | N | N | N | | | C/N | C/N |
| IKBKB | BC006231 | | | C | C | | | | | C/N | C | [C] | | [C/N] | [C] |
| IKBKB | BC108694 | C | C | C | C | C | | C | C | C | C | [C] | | [C] | [C] |
| IKBKG | | C | C | C | C | C | | C | C | C/N | C/N | [C] | | [C] | [C] |
| INPP5D | | | | C | C | | | | | C | | C | | C | C |
| INPPL1 | | C | C | C | N | [C] | | C | C | C | C | | | C | C |
| Jun | | C/N | C/N | C | C | | | C/N | C/N | C/N | C/N | | | C/N | C |
| KRAS | | N | N | | | N | | N | N | N | N | | | C/N | |
| LAT2 | | C/N | C/N | | | [N] | N | N | C/N | N | C/N | C | | C/N | C |
| LILRB3 | | | | | N | | | | | C | C | C | | C | C |
| LIME1 | | | | N | N | | | | | | | | | | |
| LYN | | [N] | | | | | | N | N | C/N | C/N | | | N | |
| MALT1 | | C | C | N | N | | | | | C | | | | | |
| MAP2K1 | | C | C | | | | | | | C | C | | | | |
| MAP2K2 | | | | | C | | | C/N | C/N | C/N | C/N | C | | C/N | C |
| MAP2K3 | | | | C | C | | | C/N | C/N | C/N | C/N | C | | C/N | C |
| MAP3K3 | | N | N | | | N | | N | N | C/N | C/N | C | | C/N | C |
| MAPK1 | | C | C | [C/N] | [N] | C | [C] | [C] | [C] | [C] | C | C | | C | C |
| MAPK12 | | C | C | C/N | N | C | | C | C | C | C | | | C | |
| MAPK13 | | C | C | C/N | C/N | C | | C | C | C | C | C | C | C/N | C |
| MAPK14 | | C | | C/N | C/N | | | C | C | C | C | C | C | C/N | C/N |
| MAPK3 | | N | | C/N | N | | | C | C | C | C | | | C | C |
| MAPK8 | | | | C/N | C/N | | | | | C/N | | | | [C] | [C] |
| MAPK9 | | | | N | N | | | | | C | C | | | C | C |
| MDM2 | | | | C/N | C/N | C | | N | N | C/N | C/N | [C] | | [C/N] | [C] |
| MYC | | C/N | C/N | [C] | [C] | C | C | C/N | C/N | C/N | C/N | C | | C | C |
| NCK1 | | | | C | C | | | C/N | C/N | C/N | C/N | | | C | C |
| NCKAP1L | | C | C | C | C | C | | C | C | C | C | C | | C | C |
| NFAT5 | | N | N | C | C | | | C/N | C/N | C/N | | | | | C |
| NFATC1 | | C | C | C | | | | C | C | C | C | | | C | C |
| NFATC3 | | | | | | | | | | C | | C | | | |
| NFATC4 | | | C | | | | | | | C | C | C | | C | |
| NFKB1 | | N | | | | | | | N | C/N | C/N | C | | | |
| NFKBIA | | C/N | N | | | | | N | N | C/N | C/N | | | [C/N] | |
| NFKBIB | | | | | | | | N | N | N | N | | | | |
| NFKBIE | | C | C | N | N | | | C | | C | C | | | C | C |
| NRAS | | N | N | | | | | [N] | [N] | [C/N] | [N] | | | C/N | |
| PIK3AP1 | | N | N | | | [N] | [N] | N | N | N | N | | | C | |
| PIK3CA | | C/N | C/N | | | [N] | [N] | C/N | C/N | C/N | C/N | C/N | | C/N | C/N |
| PIK3CB | | | | C | C | | | | | N | | C | | C | C |
| PIK3CD | | | | | | | | | | | | | | | |
| PIK3CG | | N | | N | N | | | N | N | C/N | N | | | C/N | C |
| PIK3R1 | BC030815 | [N] | [N] | C/N | C/N | | | [C/N] | [C/N] | [C/N] | [C/N] | N | | N | C/N |
| PIK3R1 | BC094795 | | | N | N | [N] | [N] | | | | | | | | |
| PIK3R2 | | | | N | N | | | | | N | | | | | |
| PIK3R3 | | | | [C/N] | [C/N] | | | C | C | C | C | | | | C/N |
| PIK3R5 | | | | C/N | C/N | | | C | C | C | | | | C/N | C |
| PLCG2 | | | | [C/N] | [C/N] | [C] | | | | | | | | C/N | C |
| PPP3CA | | | | C/N | C/N | | | | | | | | | C/N | C/N |
| PPP3CB | | | | C | C | N | | | C | C | C | C | | C | C |
| PPP3R1 | | | | C | C | | | C | C | C | C | C | | C | C |
| PPP3R2 | | | | C | C | | | | | | | | | C | C |
| PRKCA | | | | [C] | | | | | | | | | | C | C |
| PRKCB | | | | [C] | [C] | | | C | C | C | C | | | [C] | [C] |
| PTEN | | C | C | | | C | C | | | C/N | C | | | C | |
| PTPN6 | | [C] | [C] | | | [C] | [C] | C | C | C/N | C | C | | [C] | |
| RAC1 | | N | | | | [N] | | | [N] | [C/N] | [C/N] | | | | C |
| RAC2 | | | | N | N | | | | | | | | | | |
| RAC3 | | | | | N | | | [C] | [C] | [C] | [C] | | | | |
| Raf1 | | | | N | N | | | | | | | | | C | |
| RAP1A | | | | | | | | | | | | | | | |
| RAP1B | | C | C | C | C/N | | | C | C | C | C | | | C | C |
| RAP2A | | C | C | C | C | | | C | C | C | C | | | C/N | C |
| RAP2C | | N | N | C | C | C/N | N | C/N | C/N | C/N | C/N | [C] | [C] | [C] | [C] |
| RasGRP3 | | | | N | N | | | N | N | C/N | N | | | N | |
| RASSF5 | | | | C | C | | | | | C/N | | | | C | C |
| RELA | | | | C | | C | C | | | C/N | C/N | | | C/N | C |
| RHOA | | C | C | C/N | N | C | C | C | C | C | C | [C] | | [C] | [C] |
| SOS1 | | [C/N] | [N] | N | N | | | | [N] | [C/N] | [N] | | | N | |
| SOS2 | | | | | C | | | | N | C/N | C/N | | | C | C |
| SYK | | | [C] | [C] | [C] | | | C | C | C/N | C/N | | | C | C |

-continued

| | | BLNK | | BTK | | PI3K | | RAC1(GDP) | | RAC1(GTP) | | RHOA(GDP) | | RHOA(GTP) | |
|---|---|---|---|---|---|---|---|---|---|---|---|---|---|---|---|
| Protein | Isoform | NP | LT | NP | LT | NP | LT | NP | LT | NP | LT | NP | LT | NP | LT |
| TEC | | | | C/N | C/N | | | N | | C/N | N | | | N | N |
| TP53 | | | | | | | | | | C/N | C/N | | | C | C |
| VAV1 | | | N | C | C | | | N | N | C/N | N | | | C | C |
| VAV2 | | N | N | C | C | C | | N | N | C/N | N | | | C/N | C/N |
| VAV3 | | C | C | C | | | C | | | C/N | C | | | C | |

"N" and "C" indicate whether the HaloTag is at the N- or C-terminus, respectively.
Only the target proteins that interacted with a query protein are shown.
Known PPIs in human and and mouse are highlighted in blue.
Obtained from the online PPI databases, HPRD and BioGRID.

However, in many cases, lysate treatment had a profound effect on either binding affinity, interaction rates or both. These results are similar to those obtained in previous studies, either through simulation or low-throughput experiments, which demonstrated phosphorylation primarily modulates binding kinetics (Murray et al., 1998; Nishi, Hashimoto, & Panchenko, 2011; Serber & Ferrell, 2007). Our results are depicted as bar plots in FIGS. 4A and 4B. On-rates, off-rates, and binding affinities for each protein interaction in the unphosphorylated dataset were set to "0" and represented as blue circles. The relative changes in log 10 in binding kinetics and affinity for each protein pair following lysate treatment were represented as connected orange circles.

The binding kinetics and affinities were unique across the query proteins. Approximately half of the targets showed higher binding affinity to the adaptor protein BLNK after they were lysate-treated, which was associated with small increases in on-rates or decreases in off-rates. The other half of the BLNK interactions had lower binding affinities with LT-targets, a result largely associated with faster off-rates, with little or no change in the on-rate. Lysate treatment generally resulted in stronger binding affinities with PI3K, which were associated with slower off-rates. For the non-receptor tyrosine kinase, BTK, stronger affinities with LT-targets compared to NP-targets were associated with slower dissociation rates, whereas weaker affinities were associated with slower association rates (FIG. 4A).

Among the most surprising findings of this study relates to RAC1 binding to targets. GTP-bound RAC1, showed significantly faster on- and off-rates to lysate-treated targets compared to their dephosphorylated counterparts (FIG. 4A); however, despite binding rate changes that sometimes exceeded several orders of magnitude, the overall affinity ($K_D$) was largely unchanged. Thus, it appears that phosphorylation of some targets results in a dramatic form of regulation of binding rates without a significant effect on the fraction of molecules bound. Such an effect has never been previously reported. The LT→NP transition increased the average on-rates and off-rates of active RAC1 by 220- and 257-fold, respectively, with only a 1.48 change in affinity. In contrast, both the binding kinetics and affinities of GDP-bound ("inactive") RAC1 were minimally affected with lysate treatment (FIG. 4A).

Figure 4A:
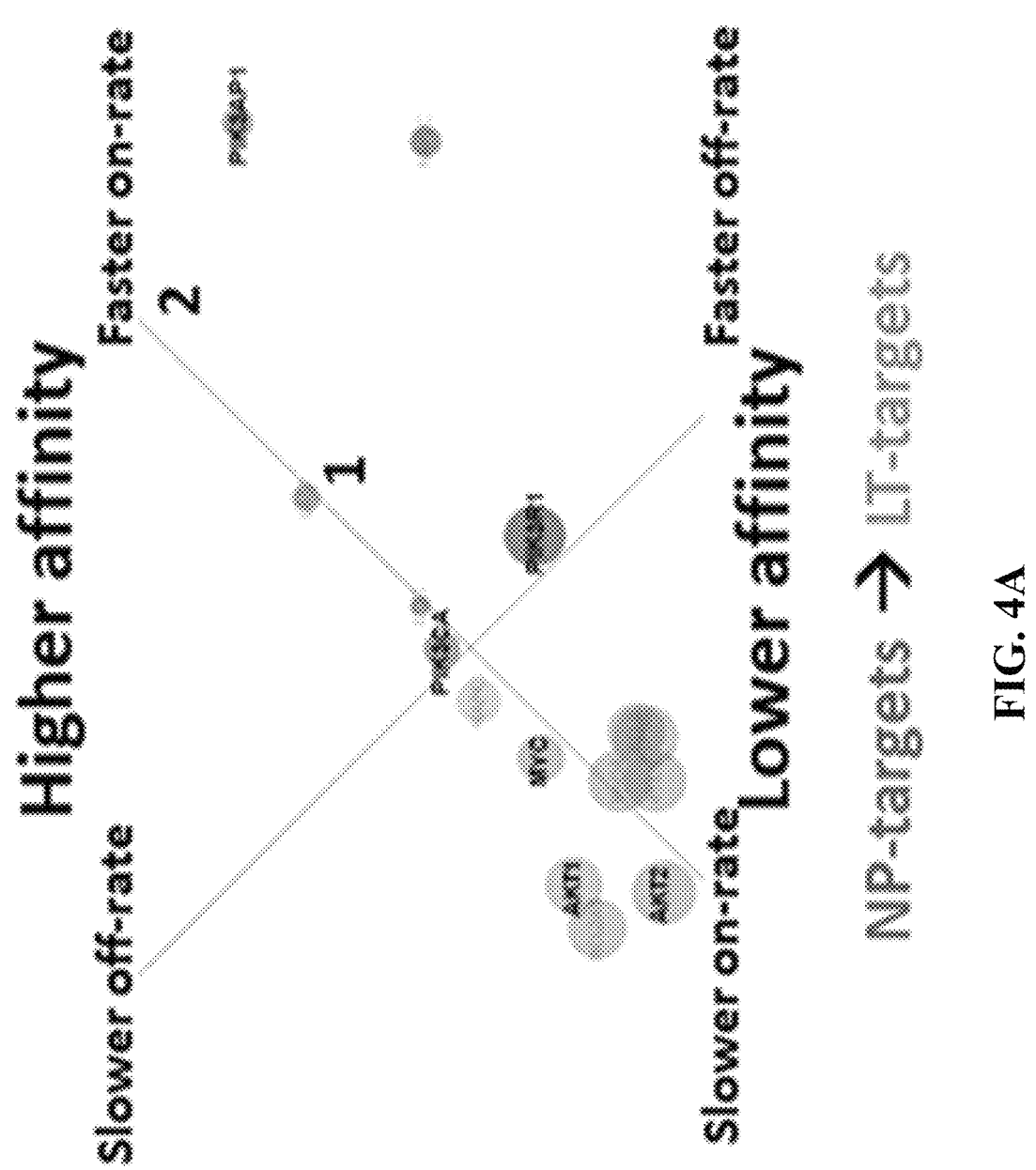
FIGS. 4A-4B. Binding kinetics and affinities modulated by B cell lysate "phosphorylation" treatment.

The majority of LT-targets bound to active RHOA with lower binding affinities than their NP counterparts, which was associated, in large part, to slower on-rates (FIG. 4A). However, roughly a quarter of the interactions resulted in stronger affinities, which were associated with slower off-rates. Inactive RHOA interacted with only five targets that were unphosphorylated and lysate-treated, with no overall differences in binding kinetics and affinities between NP- and LT-targets. Taken together, the different kinetic profiles illustrate that proteins employ different methods of regulation in their interactions with other proteins. They also indicate that the interactions are not an artefact from the NAPPA-SPRi platform.

Figure 4B:
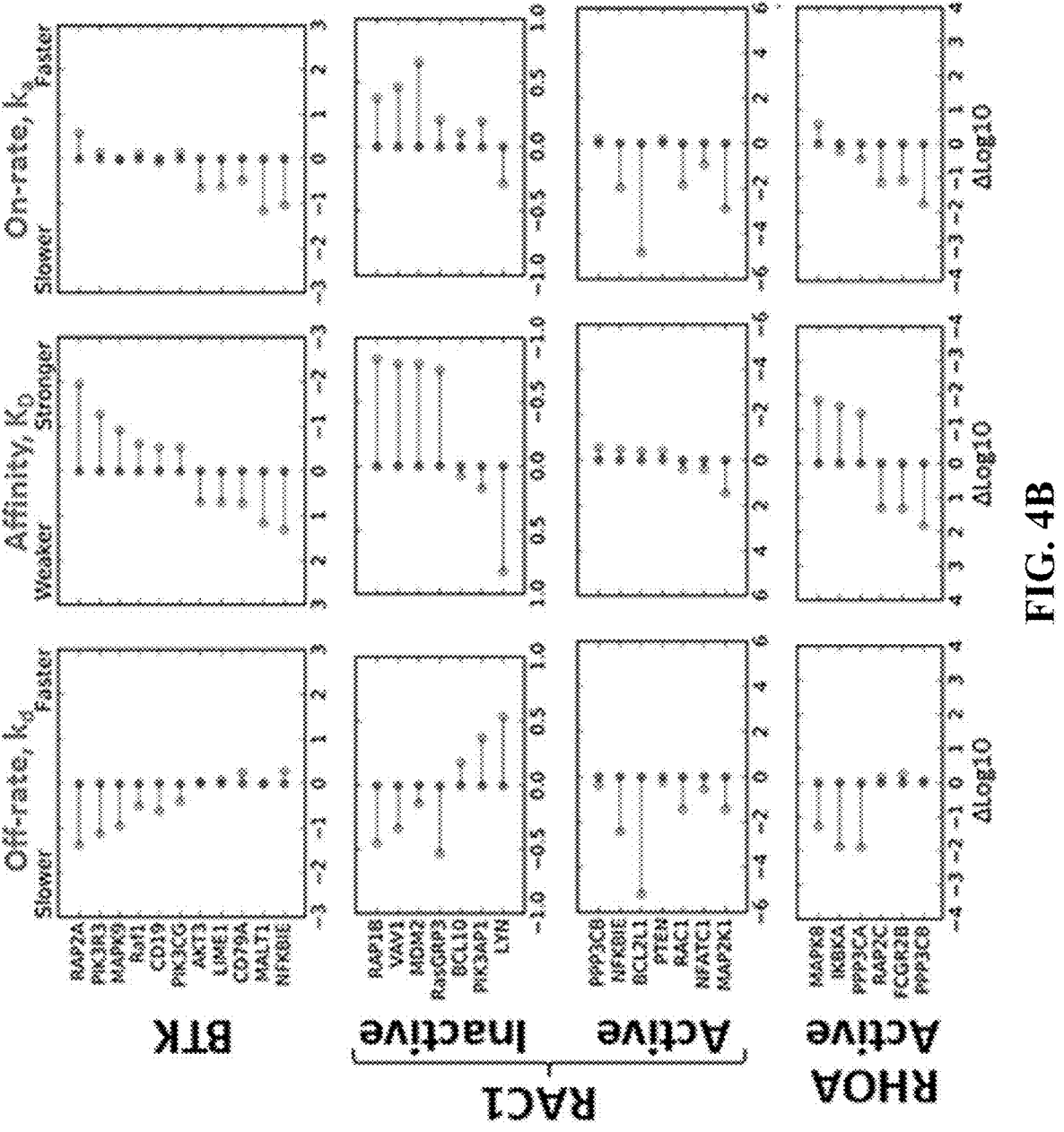

No domain or biological function was statistically-enriched found in interactions with similar binding kinetics or affinities per query. However, it is possible that these groups represent a different way to classify proteins. A compelling example is given in the radial plot representing PI3K query interactions (FIG. 4B). Here, all NP-data were zeroed. Then, the protein partners were mapped based on their relative changes in on-rates, off-rates, and binding affinities following lysate treatment. The on- and off-rates with substrates that are phosphorylated by PI3K (i.e., AKT1, AKT2, MYC) become slower following lysate treatment (Tsuchiya, Kanno, & Nishizaki, 2014). No change in on-rates were observed when PI3K interacted with its monomer subunits, PIK3CA or PIK3R1. Finally, PI3K has previously been shown to bind to PIK3AP1, which is a signaling adaptor that links the BCR with PI3K (Okada, Maeda, Iwamatsu, Gotoh, & Kurosaki, 2000). We show that the interaction between PIK3AP1 and PI3K has faster on- and off-rates following lysate treatment.

Active GTPases Interacted with More Proteins than Inactive GTPases

GTPases regulate a variety of biological processes, including cell proliferation, survival, migration, and growth. In vivo, they exist in two conformational states, an inactive GDP-bound form and an active GTP-bound form (Kumawat, Chakrabarty, & Kulkarni, 2017; Vetter & Wittinghofer, 2001). We therefore sought to better understand the effect of the two conformational states on protein partners, binding kinetics, and binding affinities for two Rho GTPases sharing 60% sequence homology, RAC1 and RHOA. The GTPases, which have intrinsic GTP hydrolysis, were activated with non-hydrolyzable GTP (i.e., GTPγS) to ensure that 100% of the binding signal reflected active GTPases.

RAC1 and RHOA interacted with 95 and 97 targets, identifying 93% known interactions and 86% (166) novel interactions. RAC1 and RHOA interacted with 38% and 171% more targets, respectively, when active (FIGS. 3C-3D), which is consistent with the idea that active GTPases mediate most downstream effectors. Ninety-two percent (92%) of the targets that interacted with inactive GTPases with NAPPA-SPRi also interacted with their active forms.

21                                                                                       22

Effect of GTPase Activation on Binding Kinetics Differed for RAC1 and RHOA

Figure 5A:
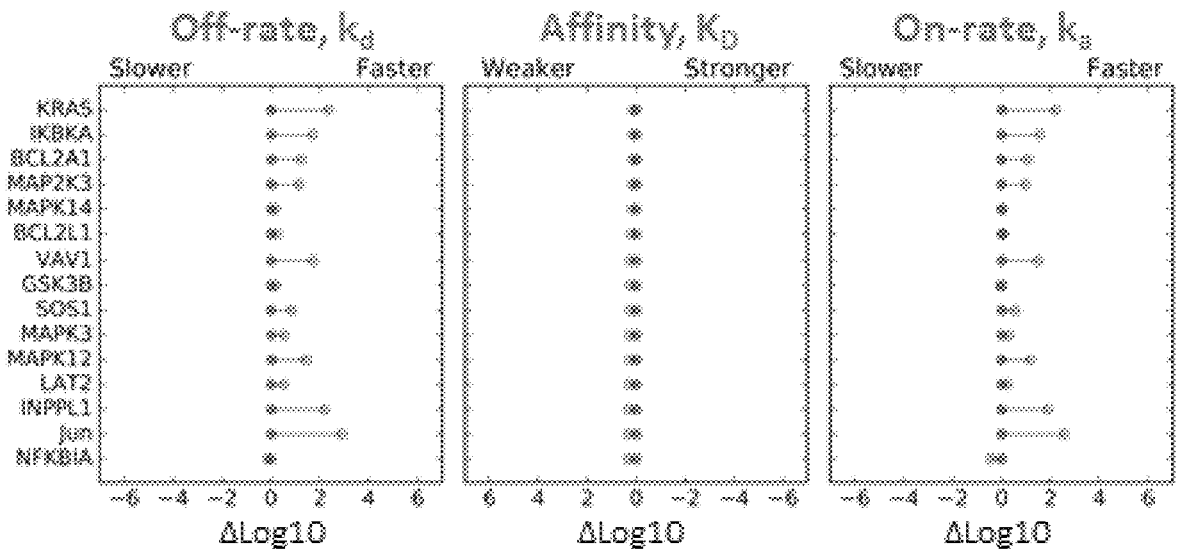
FIGS. 5A-5D. GTPase activation increases binding kinetics and/or protein partners. Bar plots and binding sensorgrams depicting the binding kinetics and affinities obtained with NAPPA-SPRi for the RAC1 query with (5A, 5C) LT-targets and (5B, 5D) NP-targets, respectively.
Figure 5B:
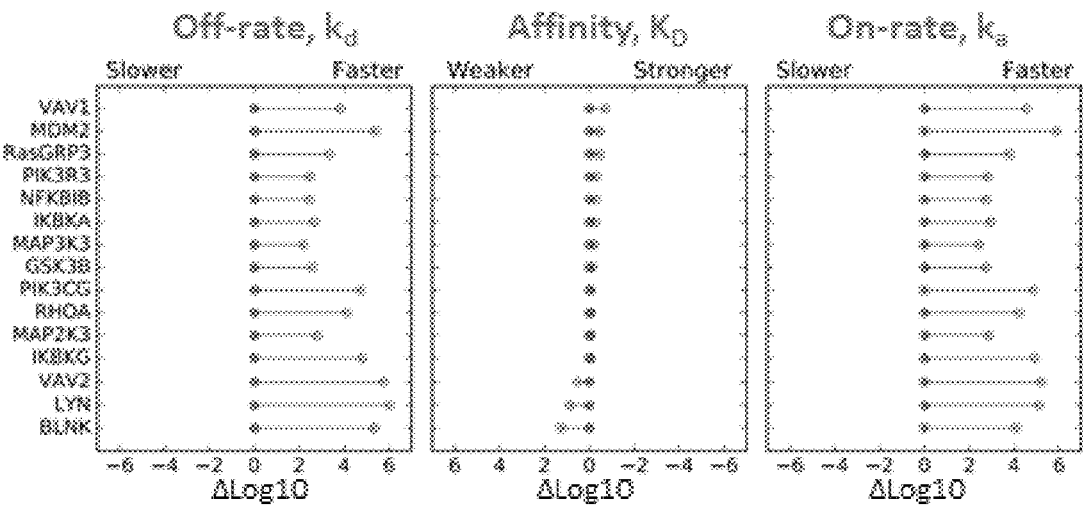
Figure 5C:
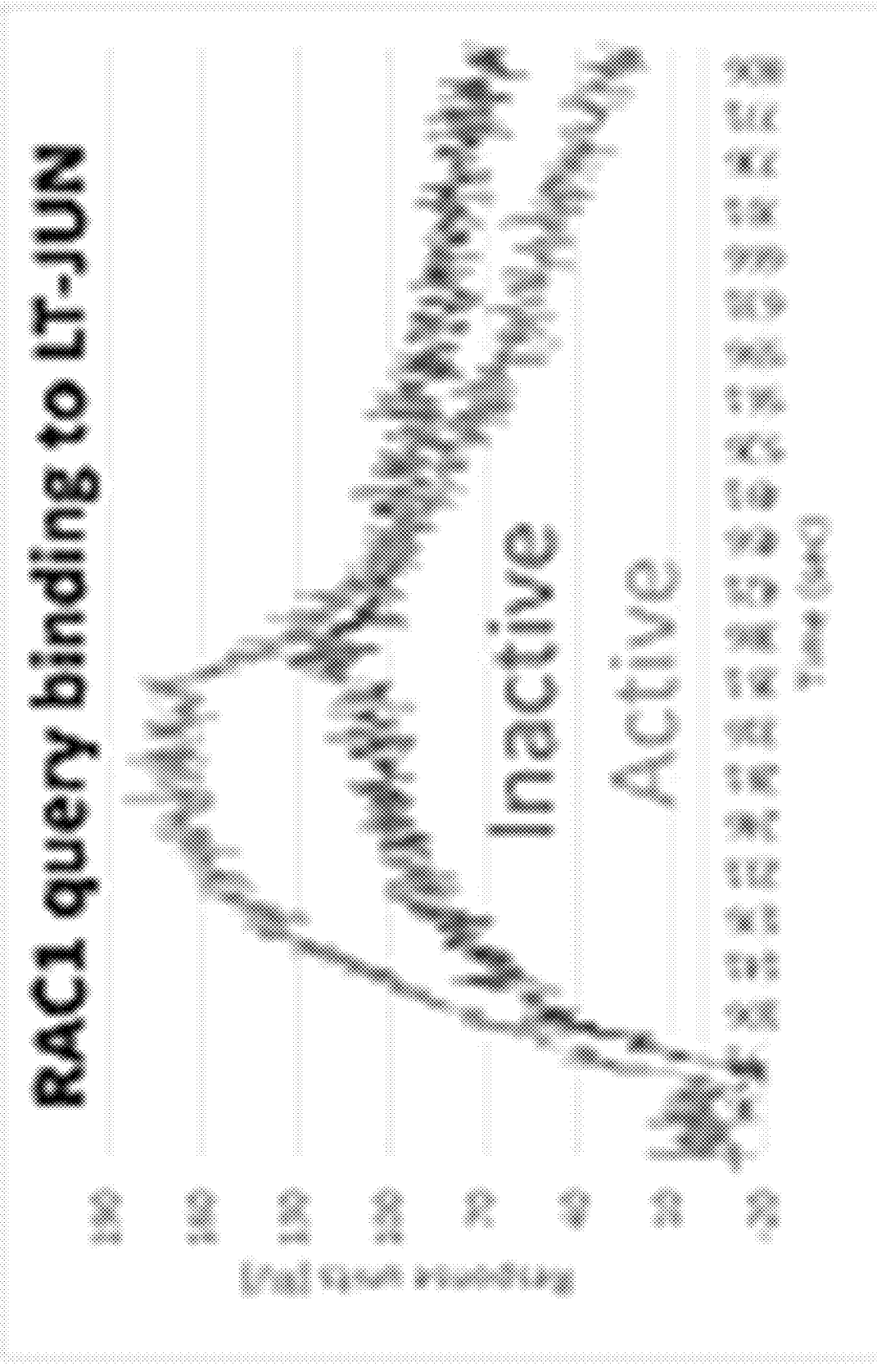
Figure 5D:
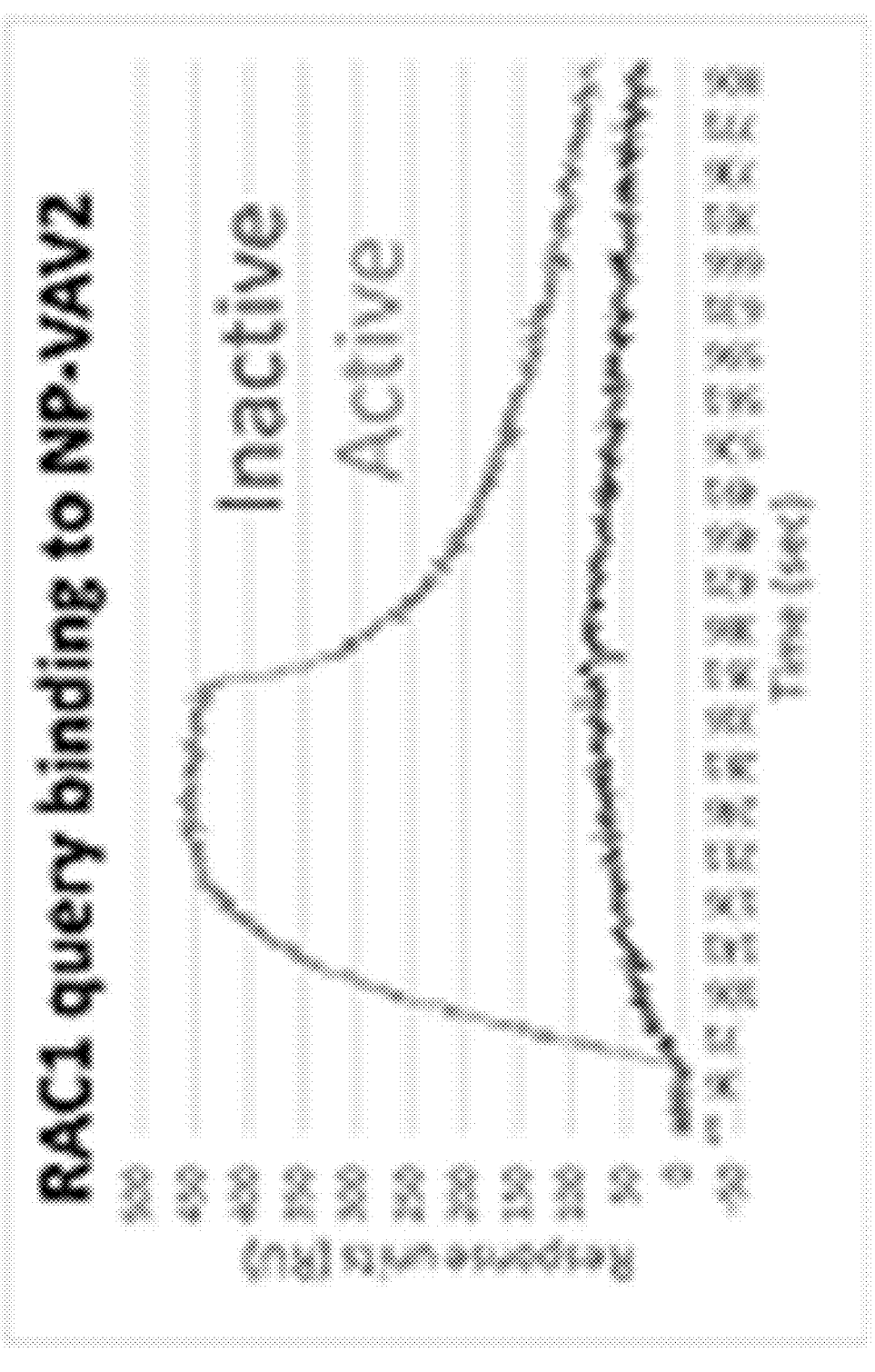

GTP-bound RAC1 interactions had faster on- and off-rates than their GDP-bound counterparts with moderate alterations to the binding affinity (FIGS. 5A-5D). In these bar plots, binding kinetics and affinities for each protein interaction in the inactive GTPase dataset were set to "0," while the relative changes in log 10 for each protein pair following GTPase activation were represented as connected orange circles. Moreover, the GDP->GTP transition with 31% (17/55) of RAC1's interactions with LT-targets increased the average on-rates and off-rates by 4.5 and 5.1 orders of magnitude, respectively, with only a decrease in binding affinity by 1.3-fold (FIGS. 5A, 5C). This effect was enhanced with NP-targets where the average on- and off-rates increased by 3.9 and 4.2 orders of magnitude, respectively, with an average increase in binding affinity by 1.9-fold for 98% of the interactions (FIGS. 5B, 5D). This novel kinetic regulation cannot be detected using classic equilibrium-based assays.

Figure 3C:
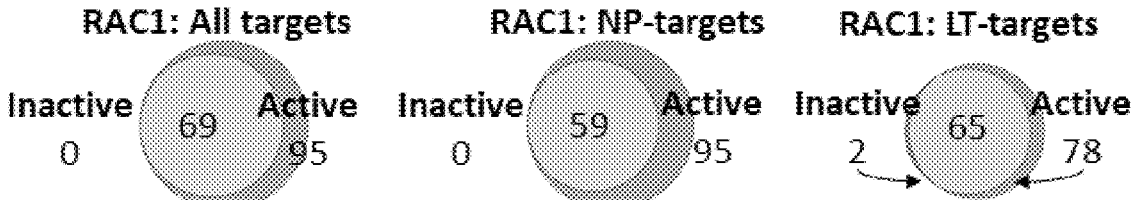

RAC1 activation significantly increased its interactions with NP-targets as well. That is, RAC1's interactions with LT-targets increased only 16% after activation while increasing 61% for NP-targets (FIG. 3C). In regards to its biological consequences, faster association rates allow RAC1 to interact competitively with targets with much higher efficiency than inactive RAC1. It also allows RAC1 to sample more interactions in a shorter amount of time. Faster dissociation rates allow proteins like GAPs access to RAC1 to negatively regulate its signaling. RAC1 activation also allows it to interact with many more unphosphorylated targets.

Figure 3D:
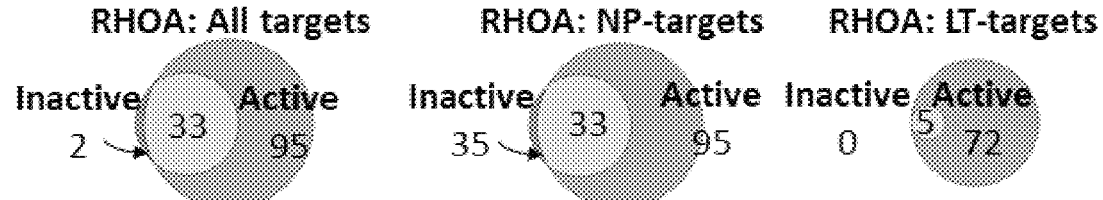

Surprisingly, RHOA activation did not significantly affect the binding kinetics or affinities with NP-targets. On average, the on-rate increased 1.8-fold, the off-rate decreased by 1.25-fold, and the binding affinity decreased 1.9-fold. However, RHOA activation significantly increased its interactions by 160% with NP-targets (i.e., 91 vs 35) and 1340% with LT-targets (i.e., 67 vs 5), suggesting that activation expands RHOA's target range (FIG. 3D).

NAPPA-SPRi Detected Novel Phosphorylated-Mediated Interactions

Figure 6A:
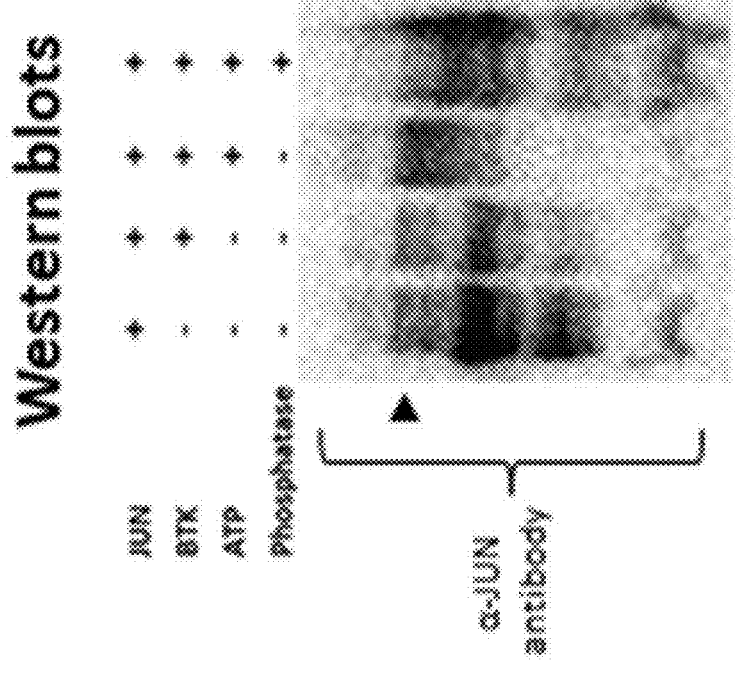
FIGS. 6A-6D. Novel phosphorylated-mediated interactions identified by NAPPA-SPRi and validated with Western blot analyses.
Figure 6A:
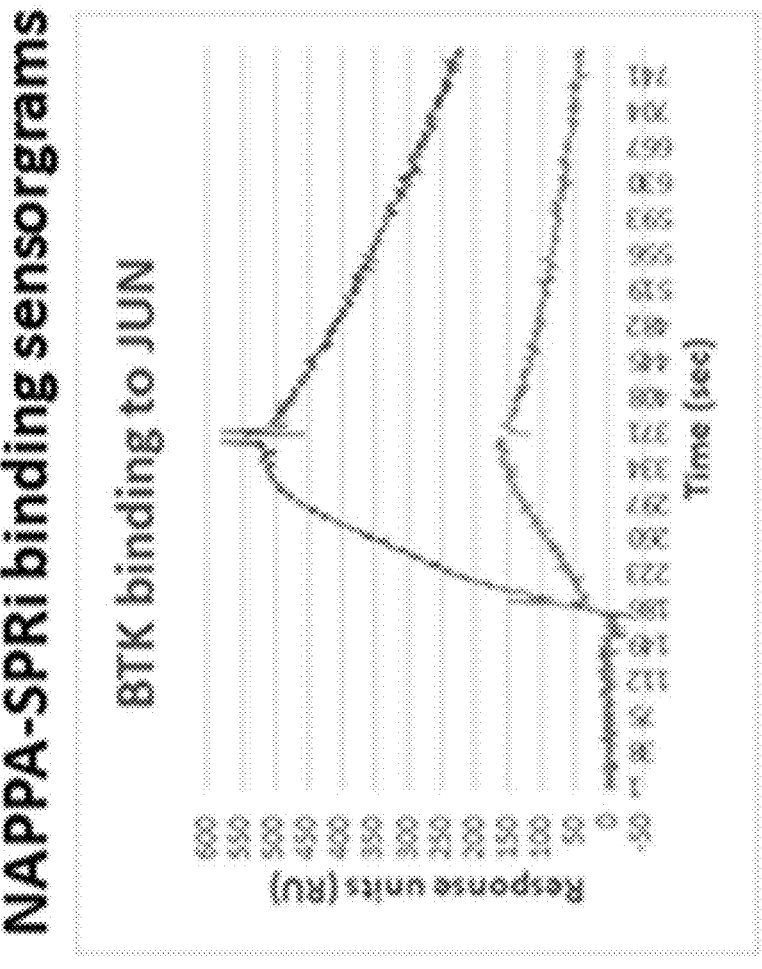

Distinct kinetic profiles between unphosphorylated and lysate-treated "phosphorylated" targets on NAPPA-SPRi may reflect phosphorylated-mediated interactions. To determine this, we explored four such novel interactions (BTK-JUN, BTK-ETS1, BTK-BCL2, PI3K-MYC) using SDS-PAGE and Western blot analyses. The first interaction includes the tyrosine kinase BTK and the transcription factor JUN, which controls the expression of genes involved in cell proliferation, apoptosis, transformation, differentiation, and development (de Gorter, Vos, Pals, & Spaargaren, 2007). The NAPPA-SPRi binding sensorgram indicates that significantly more BTK molecules bind to NP-JUN than LT-JUN (FIG. 6A). BTK also binds to and dissociates from NP-JUN faster than LT-JUN. These faster binding kinetics reflect phosphosignaling in vivo, in which exposure to particular stimuli will result in the specific phosphorylation of downstream proteins within minutes (Tarrant & Cole, 2009). As the Western blot image in FIG. 6A shows, a migration shift of JUN only occurs in the presence of BTK and ATP. The BTK-JUN-ATP sample was treated with lambda protein phosphatase to verify that the shift was due to phosphorylation. BTK knockdown inhibits JUN expression in pre-B-lymphoblastic lymphoma cells, and both BTK and JUN are often overexpressed in splenic marginal zone lymphoma and Hodgkin disease (Hiratsuka et al., 2016;

Mathas et al., 2002; Troen et al., 2004). Therefore, BTK-mediated phosphorylation may make JUN more resistant to proteases.

Figure 6B:
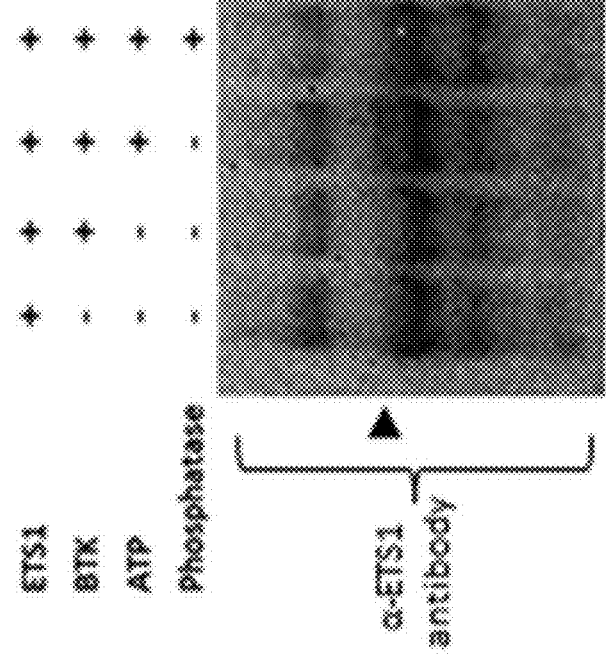
Figure 6B:
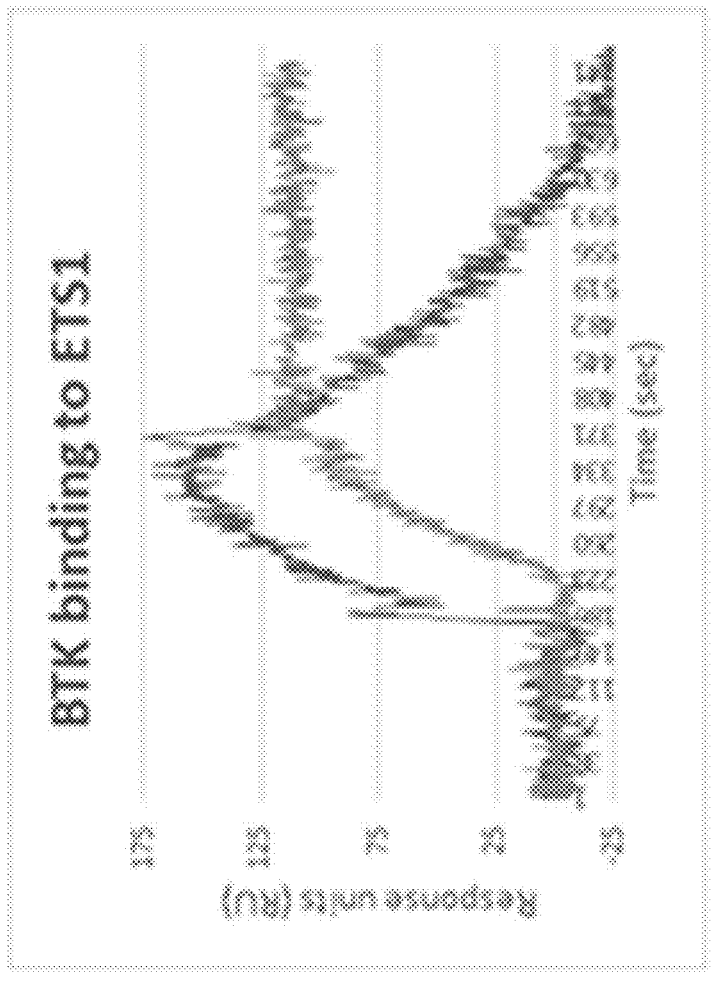
Figure 6C:
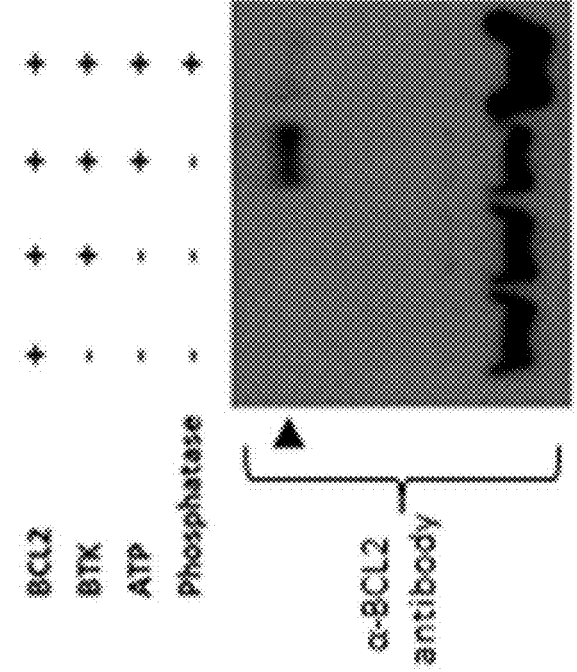
Figure 6C:
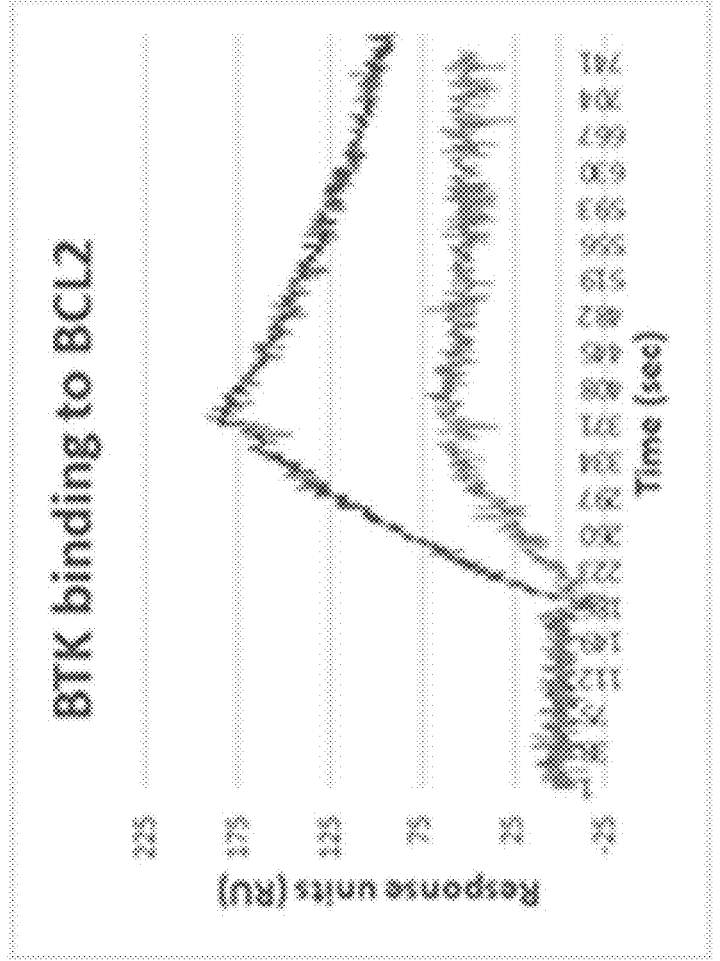

NAPPA-SPRi also detected distinct binding kinetics between BTK and NP- and LT-ETS1, a transcription factor that is essential in B cell differentiation and tolerance (FIG. 6B) (Middendorp, Dingjan, Maas, Dahlenborg, & Hendriks, 2003; Russell et al., 2015; Saito et al., 2003). The on- and off-rates were much faster with NP-ETS1 than LT-ETS1, although their binding signals were similar. It is possible that the interaction between BTK and ETS1 may also be independent of phosphorylation. NanoBRET and Western blot analyses verify that BTK phosphorylates ETS1 (FIG. 6B). BTK downregulates ETS1 expression in activated B cells as well as B cells in diffuse large B cell lymphoma, Burkitt's lymphoma, and Hodgkin disease (Mayeux et al., 2015; Testoni, Chung, Priebe, & Bertoni, 2015). It is thus possible that BTK-mediated phosphorylation makes ETSI more prone to degradation. BTK also interacted with BCL2, an important anti-apoptotic protein, on the NAPPA-SPRi platform with different binding profiles when BCL2 was dephosphorylated and lysate-treated (FIG. 6C). BCL2 phosphorylation of BCL2 was validated with Western blot analyses (FIG. 6C). A functional relationship between BTK and BCL2 has previously been demonstrated using BTK small molecule inhibitors, in which BTK inhibition increases a cell's sensitivity to the anti-apoptotic effects of BCL2 (Deng et al., 2015). Moreover, the use of BTK and BCL2 inhibitors in combination successfully killed chronic lymphocytic leukemia (CLL) cells ex vivo (Davids, 2017). Several clinical trials using BTK and BCL2 inhibitors in conjunction to treat chronic lymphocytic leukemia (CLL) are underway even though the biochemical relationship between BTK and BCL2 is not understood. The novel BTK-mediated phosphorylation of BCL2 identified in this study may inhibit BCL2's subcellular location or activity. Phosphorylation of other proteins in the BCL2 family have been demonstrated to affect their translocation to the outer mitochondrial membrane, interactions, and activity (Schinzel, Kaufmann, & Borner, 2004).

Figure 6D:
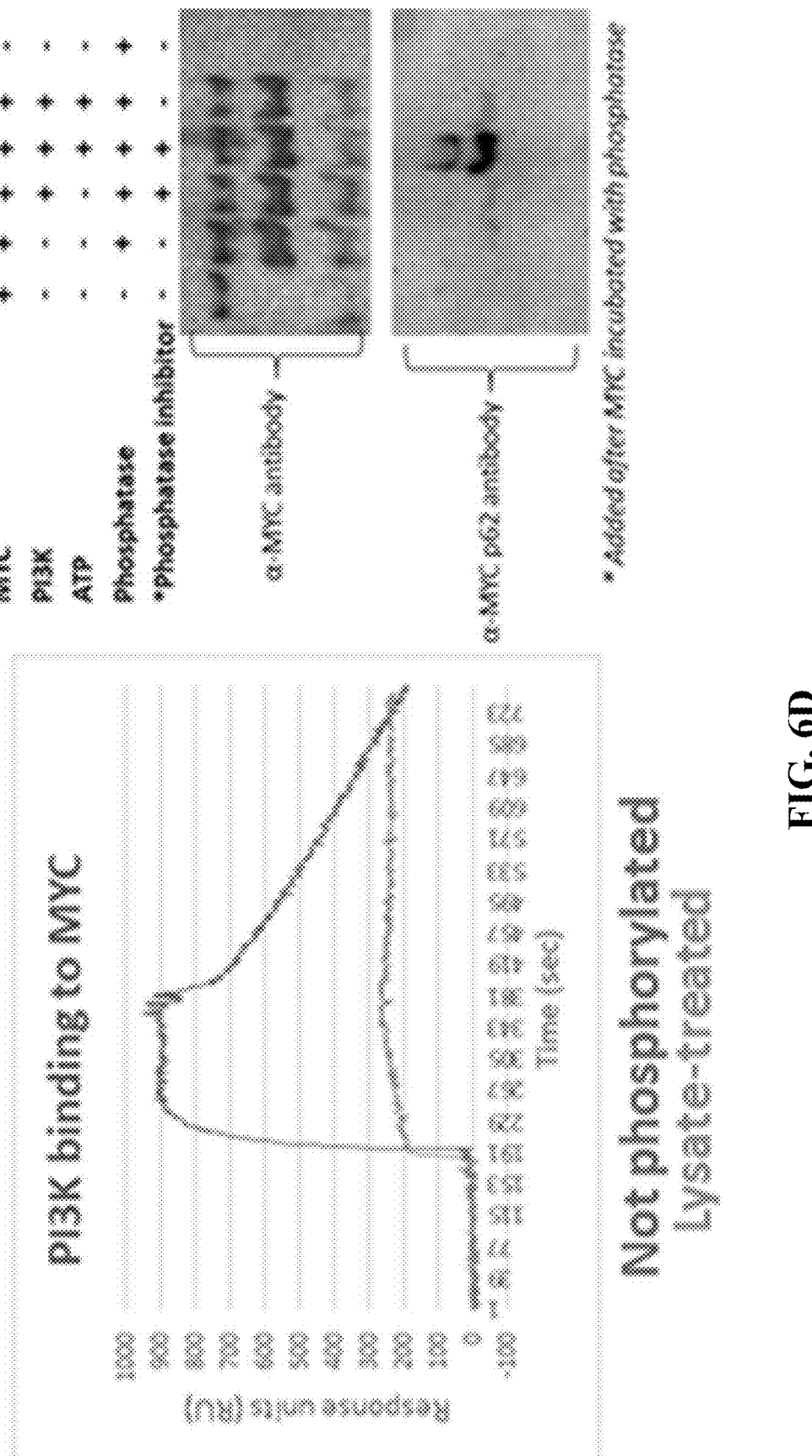

In a manner similar to those examples described above, PI3K favored binding with unphosphorylated MYC over the lysate-treated form on the NAPPA-SPRi platform (FIG. 6D). MYC is a transcription factor that is dysregulated in 70% of all cancers with two well-studied phosphorylation sites that affect its stability: serine 62 and threonine 58. Phosphorylation of serine 62 by Erk and Src family kinases increases MYC's half-life, while phosphorylation of threonine 58 by GSK3B promotes its degradation. Previous studies have shown that PI3K indirectly inhibits MYC's degradation by activating AKT1, a serine/threonine kinase that inhibits GSK3B. This may account for the observation that sustained PI3K activity and MYC overexpression result in cancer. However, no known direct physical or biochemical relationship between the two proteins have been previously reported. Here, PI3K-mediated phosphorylation of MYC was validated with NanoBRET and Western blot analyses, demonstrating that PI3K also inhibits MYC's degradation by directly phosphorylating MYC at serine 62 (FIG. 6D).

In some embodiments, the disclosed NAPPA-SPRi utilizes one or more of the following: cDNA (not linear double-stranded DNA), an SPRi chip which is a flat gold-coated slide with no microfluidic chambers, an SPR self-assembled monolayer of amine-terminated polyethylene glycol [HS—C$_{11}$ (C$_2$H$_4$O)$_6$—NH$_2$] (not amino-undecanethiol [HS—CH$_2$(CH$_2$)$_9$CH$_2$NH$_2$]), poly-L-lysine (not poly-L-glutamic acid) and electrostatic interactions (not covalently by using EDC and/or NHSS chemistry) for DNA capture, protein displayed by spot DNA and capture protein within the same spot. In other embodiments, NAPPA-SPRi may utilize a three-dimensional surface chemistry in which the tag ligand is captured covalently using EDC and/or NHSS chemistry. We use HaloTagged fusion proteins that bind covalently and specifically to a small chloroalkane ligand. Seefeld et al. uses His-tagged proteins that bind to copper-NTA spots. This interaction is not covalent ($K_D$=14 nM) and the NTA can bind non-specifically to other protein species. In some embodiments, the disclosed NAPPA-SPRi can analyze the interactions of >400 protein ligands at one time. The disclosed NAPPA-SPRi can also be used to study the effect of protein modifications or protein mutations on protein interactions.

DISCUSSION

The term "interactome" to describe the interconnecting protein network was first coined by French researchers in 1999 (Ji, 2012). Since then, large-scale interaction maps have been constructed, illuminating the complexity of the human interactome and the potential to cause a paradigm shift in personalized and precision medicine by pinpointing attractive drug targets and determining the molecular events underlying disease initiation and progression. The abundance of complex information has also stimulated the development of mathematical models to understand the system behavior of signaling pathways, which has translational potential in personalized and precision medicine, synthetic biology, biological engineering, and virology. Unfortunately, computational models of cells and signaling pathways have thus far been built using qualitative experiments that are either inherently biased or provide little mechanistic insight. Prior to this study, no method could characterize the binding kinetics and affinities in a high throughput manner. With a paucity of kinetic and affinity data, modelers have been forced to build algorithms from qualitative-based data, resulting in "best guess" approximations that could miss individual, yet critical binding kinetics that regulate signaling. Calculated kinetics guided by cellular responses may be misassigned to particular signaling components or diluted across multiple proteins. Finally, experiments in which proteins-of-interest are perturbed and the cellular responses observed are essentially "black boxes" in which many of the molecular processes remain obscure (Aldridge, Burke, Lauffenburger, & Sorger, 2006; Fumia & Martins, 2013; Heydari et al., 2017; Janes & Yaffe, 2006; Kirouac et al., 2012; Sachs, Perez, Pe'er, Lauffenburger, & Nolan, 2005).

Herein, we studied protein interactions in the BCR signaling pathway using a qualitative BRET-based method and a quantitative NAPPA-SPRi platform. NanoBRET and NAPPA-SPRi detected>80% interactions that have not been previously reported in this "well understood" pathway, which suggests that the human interactome is still largely unmapped. This large-scale kinetic also study illustrates how proteins have different ways to regulate their interactions. While our data support previous studies showing that phosphorylation modulates the binding kinetics of most protein interactions, they also contradict the commonly-held assumption that dissociation rates primarily determine binding affinity (Pollard, 2010).

Wild-type Rho GTPases were used in the present studies so that the effect of GTPase activation on GTPases protein interactions could be compared directly. Alternatively, constitutively active or dominant negative mutant GTPases could have been used. However, they are structurally different than their wild-type counterparts, thereby making their kinetic analyses outside the scope of this study (Davis et al., 2013; Kumawat et al., 2017).

The methods and software developed and described herein can be adapted toward other studies. NanoBRET, which has been used to study protein interactions in vivo, has now been optimized to analyze interactions in vitro using proteins produced with a cell-free expression system. The SPRite software could analyze other high throughput SPR data. NAPPA-SPRi could be used to study any protein interaction as long as the plasmid cDNA can be constructed, including other signaling pathways, host-pathogen protein-protein interactions, and the effect of protein mutations on protein interactions. Although the aqueous environment of NAPPA-SPRi is not well-suited for membrane proteins (e.g., receptors), the hydrophilic intracellular or extracellular domains of membrane proteins could be displayed instead. It can be imagined that NAPPA-SPRi could be expanded to screen drugs, antibodies, kinase substrates, and protein functionality. Targets could be phosphorylated with lysate from different cell lines and types, which would likely result in unique binding kinetics and interactions from those obtained in this study. PTMs other than phosphorylation could be studied with NAPPA-SPRi as well. Proteins displayed by traditional fluorescence-based NAPPA have been citrullinated and AMPylated for autoantibody and protein interaction studies, respectively, by adding peptidyl arginine deiminase 2 and AMPylators to the array (Karthikeyan et al., 2016; X. B. Yu & LaBaer, 2015).

Finally, NAPPA-SPRi throughput could be increased even further. Like standard NAPPA, NAPPA-SPRi throughput is limited by the diffusion of expressed proteins during in vitro transcription translation since spots that are less than 640 µm apart (i.e., center-to-center) may become contaminated with proteins from neighboring features. Takulapalli et al. addressed the diffusion and issue through the use of silicon nanowells that were approximately 250 microns in diameter and 75 microns deep (Takulapalli et al., 2012). The nanowells physically blocked the diffusion of expressed proteins to other nanowells and, as such, the throughput of NAPPA increased from 2,300 to 14,000 features per slide. More recently, Karthikeyan et al. used a "contra capture" approach to capture the expressed proteins separately from the printing mixture (Karthikeyan et al., 2016). The printing mixture containing plasmid cDNA, amine-to-amine crosslinker, and BSA was deposited into microwells of a polydimethylsiloxane (PDMS) wafer. During protein expression, the wafer was sandwiched to a slide coated with capturing reagent. The expressed protein was then immobilized by the capturing slide and the PDMS wafer was discarded. A variation of these themes could be applied toward NAPPA-SPRi.

Advantages Over Current Technology and Impact

The advantages of the disclosed NAPPA-SPRi include at least the following:

Any protein can be produced as long as the plasmid cDNA can be made. This includes proteins that would be toxic to a cell host and large proteins that may not be fully translated in non-homologous systems (e.g., human proteins in *E. coli* cells).

Proteins are produced using homologous cell-free expression system, which would have the appropriate ribosomes and chaperone proteins for proper protein folding. No troubleshooting is necessary for protein production and arrays are ready to be used within hours of expression.

Numerous types of cell-free expression systems are available, including those derived from human, rabbit, wheat germ, *E. coli*, and insect.

Minimal protein manipulation required. Proteins are captured in situ, thereby negating the need to purify proteins using standard column-based methods.

High throughput. 441 proteins can be analyzed simultaneously<1 hour. This throughput could be increased using a different array printer or slide set-up.

Qualitative. Determines which proteins interact.

Quantitative. Characterizes the binding kinetics and affinities.

Proteins can be modified to enable the analyses of the role of post translational modifications in protein interactions.

In short, NAPPA-SPRi is the first high throughput, quantitative method for studying protein interactions. For example, the disclosed NAPPA-SPRi arrays can be customized, may be used to select antibody clones with the highest specificity and binding affinity, to streamline the drug discovery process (e.g., determine the off-target binding of drugs), test interactions of targeted proteins before and after the addition of an "inhibitor", and/or characterize signaling pathways to identify therapeutic targets-of-interest, either by inhibiting a specific interaction, activity, or modification.

Material and Methods

RESOURCES TABLE

| REAGENT or RESOURCE | SOURCE | IDENTIFIER |
|---|---|---|
| Antibodies | | |
| Rabbit anti-human JUN monoclonal antibody, clone 60A8 | Cell Signaling Technology | Cat #9165S |
| Rabbit anti-human ETS1 monoclonal antibody, clone D808A | Cell Signaling Technology | Cat #14069S |
| Rabbit anti-human c-MYC monoclonal antibody | Abcam | Cat #ab32 |
| Rabbit anti-human c-MYC phospho S62 monoclonal antibody | Cell Signaling Technology | Cat #13748 |
| Rabbit anti-human c-MYC phospho T58 polyclonal antibody | Abcam | Cat #ab28842 |
| Mouse anti-human BCL2 polyclonal antibody | Cell Signaling Technology | Cat #15071S |
| HRP-conjugated anti-rabbit IgG | Cell Signaling Technology | Cat #7074S |
| HRP-conjugated anti-mouse IgG | Jackson ImmunoResearch | Cat #515-035-062 |
| Mouse anti-human TP53 monoclonal antibody, clone D01 | Sigma Aldrich | Cat #P6874 |
| Chemicals, Peptides, and Recombinant Proteins | | |
| 1-Step Human Coupled IVT Kit | Thermo Fisher Scientific | Cat #88882 |
| Bond-BreakerTM TCEP Solution, Neutral pH | Thermo Fisher Scientific | Cat #77720 |
| SuperSignal West Femto Maximum Sensitivity Substrate | Thermo Fisher Scientific | Cat #34096 |
| 7 kDa molecular weight cut-off (MWCO) Zeba spin desalting columns | Thermo Fisher Scientific | Cat #89882 |
| 10 mM ATP | Cell Signaling Technology | Cat #9804 |
| GTPγS | BIOLOG Life Science Institute | Cat #G019-05 |
| GDP | Sigma-Aldrich | Cat #G7127-25MG |
| HEPES | Sigma-Aldrich | Cat #54457-250G-F |
| NaCl | VWR | Cat #97061-268 |
| MgCl2 | Sigma-Aldrich | Cat #M9272-1KG |
| MnCl2 | Sigma-Aldrich | Cat #529680 |
| EDTA | Sigma-Aldrich | Cat #E6758-100G |
| NaF | Sigma-Aldrich | Cat #S6776-100G |
| Na2MoO4 | Sigma-Aldrich | Cat #M1003-100G |
| Na3VO4 | Sigma-Aldrich | Cat #450243-10G |
| PMSF, phenylmethanesulfonyl fluoride | Sigma-Aldrich | Cat #P7626-250MG |
| Pepstatin | Sigma-Aldrich | Cat #77170-5MG |
| Leupeptin | Sigma-Aldrich | Cat #L5793-5MG |
| Soybean trypsin inhibitor | Sigma-Aldrich | Cat #T6522-25MG |
| Microcystin-LR | Enzo Life Sciences | Cat #ALX-350-012-C100 |
| Glycerol | Fisher Scientific | Cat #G334 |
| Tris | MP Biomedicals | Cat #11TRIS05KG |
| Human RAC1 recombinant protein (N-terminal His tag) | Orth Lab; UT Southwestern | |
| Human RHOA recombinant protein (N-terminal His tag) | Orth Lab; UT Southwestern | |
| Human AKT1 recombinant protein (N-terminal His tag) | Thermo Scientific | Cat #P2999 |
| Human BLNK recombinant protein (N-terminal His tag) | Sino Biological | Cat #12706-H07H-50 |

-continued

| RESOURCES TABLE | | |
| --- | --- | --- |
| REAGENT or RESOURCE | SOURCE | IDENTIFIER |
| Human BTK recombinant protein (N-terminal His tag) | Sino Biological | Cat #10578-H08B-50 |
| Human PIK3CA/PIK3R1 (p110α/p85α) (N-terminal His tag of p110α) | Thermo Fisher Scientific | Cat #PV4788 |
| Human ETS1 recombinant protein (N-terminal His tag) | RayBiotech Inc. | Cat #230-00235-50 |
| Human JUN recombinant protein (N-terminal His tag) | RayBiotech Inc. | Cat #230-00701-50 |
| Human BCL2 recombinant protein (N-terminal His tag) | RayBiotech Inc. | Cat #230-00557-50 |
| Human GRB2 recombinant protein | Abcam | Cat #ab169901 |
| Human MYC recombinant protein (C-terminal arginine tag) | Abcam | Cat #ab169901 |
| Human TP53 recombinant protein | Abcam | Cat #ab189748 |
| Calf intestinal alkaline phosphatase | New England BioLabs | Cat #M0290L |
| NEBuffer 3 | New England BioLabs | Cat #B7003S |
| NEBuffer for PMP | New England BioLabs | Cat #P0753L |
| 10 mM MnCl2 (for lambda protein phosphatase buffer) | New England BioLabs | Cat #P0753L |
| lambda protein phosphatase | New England BioLabs | Cat #P0753L |
| RPMI-1640 | Thermo Scientific | Cat #11875-093 |
| 10% HyCloneTM fetal bovine serum | Fisher Scientific | Cat #SH3007003 HI |
| 4× Laemmli sample buffer | Bio-Rad | Cat #1610747 |
| PVDF membrane | Bio-Rad | Cat #1620239 |
| Sodium bisulfite | Sigma Aldrich | Cat #243973-100G |
| SDS | EMD Biosciences | Cat #7910-500GM |
| 10× Tris/Tricine/SDS running buffer | Bio-Rad | Cat #1610744 |
| 20× NuPAGE transfer buffer | Thermo Scientific | Cat #NP00061 |
| Series S Sensor Chip CM5 | GE Healthcare | Cat #29149603 |
| Amine coupling kit | GE Healthcare | Cat #BR100050 |
| HBS-P + Buffer 10× | GE Healthcare | Cat #BR100671 |
| Acetate 5.0 | GE Healthcare | Cat #BR100351 |
| Acetate 5.5 | GE Healthcare | Cat #BR100352 |
| NaOH 50 | GE Healthcare | Cat #BR100358 |
| Commercial Assays | | |
| NanoBRET Nano-Glo Detection System | Promega Corporation | Cat #N1662 |
| Experimental Models: Cell Lines | | |
| Human: Ramos RA-1 | ATCC | CRL-1596 |
| Recombinant DNA | | |
| Plasmid cDNA with gene inserts displayed in Supplemental Information, | DNASU plasmid repository | |
| Software and Algorithms | | |
| Scrubber2 | BioLogic Software | |
| SPRite | This paper | |
| Plexera Data Analysis Module | Plexera | |
| Other | | |
| White, high binding half-area 96-well plates | Greiner Bio-One | 82050-040 |
| SuperSep Phos-TagTM 12.5% SDS-PAGE | Wako Pure Chemical Industries | 195-17991 |

Preparation of Plasmid cDNA

Genes-of-interest (GOIs) were obtained from the Virginia G. Piper's Center for Personalized Diagnostics' plasmid repository, DNASU (Tempe, AZ), and Open Biosystems (Lafayette, CO). The genes were shuttled into Invitrogen Gateway®-compatible vectors (Thermo Fisher Scientific; Waltham, MA) produced in-house with a HaloTag at the N-terminus (pJFT7_nHalo_DC), a HaloTag at the C-terminus (pJFT7_cHalo_DC), or a NanoLuc at the N-terminus (pJFT7_nNanoLuc_DC) as previously described (Festa, Steel, Bian, & Labaer, 2013; Saul et al., 2014). The pJFT7_nNanoLuc_DC plasmid was adapted from expression vectors, pJFT7_nHalo_DC and N-terminal pFN31A Nluc CMV-Hygro Flexi® Vector (Promega Corporation; Madison, WI). Successful cloning of the genes-of-interest was confirmed via Sangar sequencing, which was performed by the DNASU Sequencing Core at Arizona State University (Tempe, AZ). 109 target genes were represented with HaloTag at the N- and C-terminus, with the exception of genes with HaloTag only at the N-terminus (BLNK, PPP3CC) or only at the C-terminus (IFITM1, MAP2K1, PPP3R2). The target genes, AKT2, IKBKB, and PIK3R1, were represented with two different isoforms that differed significantly in size. The query genes, AKT1, BLNK, BTK, DAPP1, LYN, MAPK14, PIK3CA/PIK3R1, GDP-bound RAC1, GTP-bound RAC1, GDP-bound RHOA, GTP-bound RHOA, and SYK, had an N-terminal NanoLuc.

Reagents

The 1-Step Human Coupled IVT Kit and Bond-Breaker™ TCEP Solution, Neutral pH, were from Thermo Fisher Scientific (Waltham, MA). The ATP was from Cell Signaling Technology (Danvers, MA). The HaloTag® NanoBRET 618 Ligand and Nano-Glo Substrate were from Promega Corporation (Madison, WI). Unless otherwise noted, all other materials and reagents were obtained from Sigma-Aldrich (St. Louis, MO).

NanoBRET Protein Expression

White, high binding half-area 96-well plates (Greiner Bio-One; Austria) were blocked overnight at 4° C. with 100 μL 1% BSA (w/v) in PBST, then washed with 100 μL PBST and 100 μL PBS. The HeLa lysate was spun at 10k×g for 2 min at 4° C., and the insoluble pellet was discarded. Target and query proteins were expressed for 1.5 hrs at 30° C. in the 1-Step Human Coupled IVT Kit, in which the HeLa lysate, reaction mixture, accessory proteins, and 200 ng/μL plasmid cDNA are mixed at a 5:2:1:2 ratio, respectively, such that 1 μL of target mixture or 1 μL of query mixture were added per well.

GTPase Inactivation or Activation

The GTPase queries were GTP- or GDP-bound with 1 mM GTPYS (BIOLOG Life Science Institute; Germany) or GDP, respectively, in 50 mM HEPES, 150 mM NaCl, 5 mM MgCl2, 5 mM EDTA, 1 mM TCEP, pH 7.4, for 1 hour at room temperature.

NanoBRET Buffer Conditions

Each query had five 96-well plates containing targets, with each set having a specific buffer. The BLNK, DAPP1, and JUN queries were analyzed in 50 mM HEPES, 150 mM NaCl, 1 mM TCEP, 0.01% Tween-20, pH 7.4. The GDP-bound RAC1, GTPYS-bound RAC1, GDP-bound RHOA, and GTPγS-bound RHOA queries were analyzed in 50 mM HEPES, 150 mM NaCl, 1 mM TCEP, 5 mM MgCl2, 0.01% Tween-20, pH 7.4. The AKT1 query was analyzed in 50 mM Tris-HCl, 150 mM NaCl, 0.01% Tween-20, 250 μM ATP, 1 mM TCEP, pH 7.4. The BTK query was analyzed in 50 mM Tris-HCl, 150 mM NaCl, 0.01% Tween-20, 250 μM ATP, 1 mM TCEP, 4 mM MgCl2, pH 7.4. The LYN query was analyzed in 50 mM HEPES, 150 mM NaCl, 1 mM TCEP, 0.01% Tween-20, 10 mM MgCl2, 250 μM ATP, pH 7.4. The MAPK14 (p38) query was analyzed in 20 mM Tris-HCl, 150 mM NaCl, 0.01% Tween-20, 250 μM ATP, 1 mM TCEP, pH 7.4. The PIK3CA/PIK3R1 (PI3K) query was analyzed in 50 mM Tris-HCl, 150 mM NaCl, 0.03% Tween-20, 250 μM ATP, 1 mM TCEP, 3 mM MgCl2, pH 7.4. The SYK query was analyzed in 60 mM HEPES, 5 mM MgCl2, 5 mM MnCl2, 1 mM TCEP, 250 μM ATP, 0.01% Tween-20, pH 7.5.

NanoBRET Analyses

Query and target proteins were diluted 30-fold each in buffer, such that 1 μL of query and 1 μL target protein were diluted to 60 μL total per well (FIG. 2A). One replicate received NanoBRET 618 ligand while the second (control) replicate received DMSO at a 1000-fold dilution. Samples were incubated at 15° C. for 1 hr. The Nano-Glo luciferase substrate was added at a 500-fold dilution and the plates immediately analyzed with a Perkin Elmer Envision plate reader equipped with an emission filter 460/50m, emission filter 590 nm long pass, and a luminescence −/− single mirror. The noise, or luciferase emission, was read at 410-510 nm for one second. The signal, or NanoBRET 618 ligand emission, was read at ≥590 nm for 1 second. A positive control, in triplicate, was placed on each plate, which was the Jun (query)—Fos (target) interactions with and without NanoBRET 618 ligand. The Jun-Fos interaction was used as a quality control of the sample processing as well as to determine the standard deviation within each plate. Duplicate or triplicate negative controls were included on each plate, which were the Jun (query) with no target, with and without the NanoBRET 618 ligand. All pipetting steps, with the exception of making the GTPases GDP- or GTP-bound, were performed with the Beckman Coulter Biomek FX liquid handler (Brea, CA).

NanoBRET Data Analyses

The corrected mBU value was determined as described in (reference). The mean (μ) and standard deviation (Δ) of the negative controls within each plate were also determined. Protein interactions were identified as those having corrected mBU values≥μ+2Δ, or two standard deviations higher than the mean of the replicate negative controls in their associated 96-well plate. To determine whether the detected interactions were known or novel, the data were compared with human, mouse, and rat interactions curated by the online protein interaction databases, Biological General Repository for Interaction Datasets (BioGRID) and Human Protein Reference Database (HPRD). Proteins isoforms with the same name but different sequences (i.e., AKT2, IKBKB, PIK3R1) were counted as different proteins, which included previously-reported interactions where the specific isoform (e.g., PIK3R1 BC030815 or BC094795) was not indicated.

| Counted known and novel interactions detected by NanoBRET | | | | | | | | | | | |
| --- | --- | --- | --- | --- | --- | --- | --- | --- | --- | --- | --- |
| Type of PPI | AKT1 | BLNK | BTK | DAPP1 | LYN | MARK14 | PI3K | RAC1(GDP) | RAC1(GTP) | RHOA(GDP) | RHOA(GTP) | SYK |
| Known PPIs that were not detected | 6 | 8 | 11 | 2 | 15 | 16 | 14 | 9 | 10 | 9 | 8 | 13 |
| Known PPIs that were detected | 20 | 8 | 4 | 1 | 7 | 2 | 13 | 5 | 4 | 4 | 5 | 8 |
| Novel PPIs | 40 | 50 | 22 | 22 | 38 | 12 | 28 | 39 | 59 | 32 | 32 | 35 |
| Total PPIs detected | 60 | 58 | 26 | 23 | 45 | 14 | 41 | 44 | 63 | 36 | 37 | 43 |
| % known PPIs that were detected | 77 | 50 | 27 | 33 | 32 | 11 | 48 | 36 | 29 | 31 | 38 | 38 |

Protein interactions detected by NanoBRET

| Target | Ref Seq ID | UniProt # | AKT1 | BLNK | BTK | DAPP1 | LYN | MAPK14 | PI3K | RAC1-GDP | RAC1-GTP | RHOA-GDP | RHOA-GTP | SYK |
|---|---|---|---|---|---|---|---|---|---|---|---|---|---|---|
| | | | | | | | | | | Query | | | | |
| AKT1 | BC000479.2 | P31749 | N/C | N/C | C | C | C | | N | C | N/C | C | | |
| AKT2 | BC063421 | P31751 | C | N | | | | | | C | N/C | | | |
| AKT2 | BC120994 | Q6P4H3 | | N | | | | | | C | N/C | C | | N |
| AKT3 | AJ245709 | Q9Y243 | C | | | | C | | | C | C | | | N |
| ARHGEF7 | EU832554.1 | Q14155 | | | | | | | N | C | | C | | |
| BCL10 | NM_003921 | O95999 | | | | | | | | C | | C | | |
| BCL2 | BC027258 | P10415 | | | | N | | C | | C | | C | | |
| BCL2A1 | U29680 | Q16548 | N/C | N | C | | | | C | C | N/C | | N | |
| BCL2L1 | BC019307 | Q07817 | N/C | | | | | | N | C | N | | | N |
| BLK | BC007371 | P51451 | | | | | C | | N | | N | | | N |
| BLNK | BC018906.2 | Q8WV28 | N | | | N | | | | | | | | N |
| BTK | NM_000061 | Q06187 | | | | | | | N | | N | | N | N |
| CARD11 | BC111719 | Q9BXL7 | | | | N | | | N | | N | C | | N |
| CD19 | BC006338 | P15391 | | | | | | | N | C | | C | | |
| CD22 | BC109306 | Q32M46 | | | | N/C | | | | C | | | | |
| CD72 | BC030227 | P21854 | C | | C | N | | C | C | C | C | | C | |
| CD79A | BC113733 | P11912 | N/C | N | | C | C | | N/C | C | N/C | C | N/C | N |
| CD79B | BC030210.1 | Q6PIS4 | N/C | N | N | C | C | N | N | C | N | | | N |
| CD81 | BC002978 | P60033 | N/C | N | | | | | C | | N | | N/C | N |
| CDC42 | NM_001791 | P60953 | | N | | C | | N | N | | | C | C | N |
| CDKN2A | U26727 | Q8N726 | | | | | | | | C | N | C | | |
| DAPP1 | BC012924 | Q9UN19 | | | | | | | | C | | C | | |
| EGR1 | BC073983.1 | P18145 | | | | | N/C | | N | C | N | C | | |
| ETS1 | X14798 | P14921 | C | | C | N/C | C | | | | C | C | | |
| EZR | BC013903 | P15311 | N/C | N | | | | N | N/C | | N | C | | N |
| FCGR2B | BC031992 | P31994 | N/C | | | | | | N/C | | | | | |
| FOS | BC004490 | P01100 | C | N | | | | | N/C | | | | | N |
| GRAP2 | BC025692 | O75791 | | N | | | | | N | | C | | | |
| GRB2 | BC000631 | P62993 | | | | | | | | C | | | | |
| GSK3B | BC000251 | P49841 | | | | | | | | C | | C | C | N |
| HRAS | NM_005343 | P01112 | | | | C | | | C | C | | C | N | |
| IFITM1 | BC000897 | P13164 | C | | C | | | | C | | | | C | |
| IKBKA | NM_001278 | O15111 | C | C | | C | C | | | C | C | C | | |
| IKBKB | BC006231 | O14920 | N/C | | | C | | | N/C | | C | | N | N |
| IKBKB | BC108694 | Q32ND9 | N | N | | N | | | N/C | C | N | | N | N |
| IKBKG | BC000299 | Q9Y6K9 | N | N | | | | | N | | N | C | N | |
| INPPSD | BC113580 | Q92835 | | N | | | | | N | | N | | | |
| INPPL1 | BC140853 | O15357 | | N | | | | | | | | | | |
| JUN | BC006175 | P05412 | | | | | | | | C | | | | |
| KRAS | BC013572 | P01116 | C | | | C | C | C | C | C | C | | C | |
| LAT2 | BC009204.2 | Q9GZY6 | C | | | C | C | | | | N | | C | |
| LILRB3 | BC112198 | O75022 | N/C | N | | C | | | C | | N | | N/C | N |
| LIME1 | BC017016 | Q9H400 | N | | C | | C | C | | | N | C | N | |
| LYN | NM_002350 | P07948 | N | C | | | C | | N | | C | C | | N |
| MALT1 | BC030143 | Q9UDY8 | N | C | | | N/C | | | C | C | | | |
| MAP2K1 | BC137459 | A4QPA9 | C | | | | | | | | | | C | |
| MAP2K2 | BC000471 | P36507 | N/C | | N | C | N | | C | C | C | C | N | |
| MAP2K3 | NM_002756 | P46734 | N/C | C | | | N | C | | C | C | C | | |
| MAP3K3 | AL834303 | Q99759 | C | C | N | | | N | | | C | C | | N |
| MAPK1 | BC017832.1 | P28482 | N/C | | | | | C | N | C | | | | N |
| MAPK12 | CR456515 | P53778 | | C | | | | | N/C | N | | | | |
| MAPK13 | BC085196.1 | O15264 | C | C | | | N/C | | | C | N/C | C | C | |
| MAPK14 | BT006933 | Q16539 | C | N | | N | N | | | C | C | | | |
| MAPK3 | BC013992 | P27361 | | | | | | | | | | | | N |
| MAPK8 | NM_002750 | P45983 | | N | | | | | | | | | | N |
| MDM2 | NM_002392.3 | Q00987 | | N | | | | | | N | C | C | | |
| MYC | BC000141 | P01106 | | N/C | | | | | N/C | N | N | | N | N |
| NCK1 | BC006403.2 | P16333 | N | | | | | | C | | | C | | |
| NCKAP1L | BC093769 | P55160 | | | | | | N | N/C | | | C | | N |
| NFAT5 | BC131509 | O94916 | | | | | | | | | | C | | |
| NFATC1 | BC112243 | Q2M1S3 | | | C | | | N | | | | C | | |
| NFATC3 | BC001050 | Q12968 | C | C | | | | N | | | C | | C | |
| NFATC4 | BC053855 | Q14934 | C | N/C | | C | | | | C | C | | C | |
| NFKB1 | BC051765 | P19838 | | N | | | | N | | C | C | C | | |
| NFKBIA | NM_020529 | P25963 | N | N | | | | N | N | | N | | | N |
| NFKBIB | BC015528 | Q15653 | | N | | | | N | | | N | | | N |
| NFKBIE | NM_004556.2 | O00221 | N | N/C | | | | N | | | N | C | | N |
| NRAS | BC005219 | P01111 | | N | | | | | | | | C | | |
| PIK3AP1 | NM_152309 | Q6UJ8 | | | C | | | N | | C | | C | | |
| PIK3CA | BC113603 | P42336 | C | C | | | | N | | | C | C | | |
| PIK3CB | BC114432 | P42338 | C | N | | | | N | | | N | N | | |
| PIK3CD | BC132919.1 | O00329 | | | | | | N | | N | N | C | | |
| PIK3CG | BC035683 | P48736 | | N/C | | | | N | | | N/C | | | N |
| PIK3R1 | BC030815 | P27986 | N | C | | | | | N/C | | | | | N |

-continued

Protein interactions detected by NanoBRET

| | | | Query | | | | | | | | | | | |
|---|---|---|---|---|---|---|---|---|---|---|---|---|---|---|
| Target | Ref Seq ID | UniProt # | AKT1 | BLNK | BTK | DAPP1 | LYN | MAPK14 | PI3K | RAC1-GDP | RAC1-GTP | RHOA-GDP | RHOA-GTP | SYK |
| PIK3R1 | BC094795 | P27986 | [N] | [N] | | | | | [N/C] | | | C | | |
| PIK3R2 | BC032647 | Q05BV6 | | N | | | | | | | | | | |
| PIK3R3 | BC021622 | Q8N381 | | | | | | | [N] | C | | | | N |
| PIK3R5 | BC028212 | Q8WYR1 | C | | | | N | N/C | C | | | | | N |
| PLCG2 | BC007565 | P16885 | C | [C] | | [C] | [N] | C | [C] | N/C | N/C | | | |
| PPP3CA | BC025714 | Q08209 | [N] | | | C | | | | | C | | C | |
| PPP3CB | BC028049.1 | P16298 | N | | | | | | N | | | | | N |
| PPP3CC | HQ448368 | P48454 | N | N | N | N | N | | | | N | | | N |
| PPP3R1 | BC027913 | P63098 | N | N | | | | | N | C | N | C | | |
| PPP3R2 | JF432717 | Q95LZ3 | | | | | | | | | | C | | |
| PRKCA | NM_002737 | P17252 | | N | | | | | N | | | | | |
| PTEN | BC005821 | P60484 | [C] | C | | | | C | | C | C | [C] | [C] | |
| PTPN6 | BC002523 | P29350 | | | | | | | | | C | | | |
| RAC1 | BC107748.1 | P63000 | [C] | N/C | | | C | | | [N/C] | [C] | | | C |
| RAC2 | BC001485 | P15153 | N/C | N | N/C | | | | N | | N | | N | N |
| RAC3 | BC009605 | P60763 | N/C | C | C | | C | | | | | | | |
| RAF1 | BC018119 | P04049 | [C] | C | | | C | | | | N/C | | C | |
| RAP1A | BC014086.2 | P62834 | | | | | N/C | | | | N/C | | C | |
| RAP1B | AL080212 | P61224 | | N | | | N/C | | | | C | | C | C |
| RAP2A | BC070031.1 | P10114 | N | C | N | | C | | | | N/C | | N | N |
| RAP2C | BC003403.1 | Q9Y315 | N | | N | | C | | | | | | | N |
| RasGRP3 | NM_170672 | Q8IV61 | | | N/C | | | | | | | | | N/C |
| RASSF5 | AL832784.1 | Q8WWW0 | C | N/C | C | | N/C | | | | C | | C | N |
| RELA | BC110830 | Q2TAM5 | C | C | C | | | | | | | | | C |
| SOS2 | HQ258542 | Q07890 | | | C | | N/C | | | | | | | |
| SYK | BC011399 | P43405 | | [N] | | | [N/C] | | | | C | | | |
| TEC | BC143487 | P42680 | N | N | [N] | | [C] | | | | [N/C] | N | N | N |
| TP53 | BC003596 | P04637 | N | N | [N] | | [N] | | | | N/C | N | | |
| VAV1 | BC013361 | Q96D37 | C | [N/C] | [C] | | N | | | | [C] | [C] | | |
| VAV2 | BC132967 | P52735 | | N | N | | C | | | | | | | |
| VAV3 | NM_006113 | Q9UKW4 | | | | | | | | | [C] | | | N |

"N" and "C" indicate whether the HaloTag is at the N- or C-terminus, respectively.

Only the target proteins that interacted with a query protein are shown.

Known PPIs in human and and mouse are highlighted in blue. Obtained from the online PPI databases, HPRD and BioGRID.

Nappa-SPRI Method Details

Reagents and Materials ATP was from Cell Signaling Technology (Danvers, MA). GTPγS was obtained from BIOLOG Life Science Institute (Germany). Brij-35; Bond-Breaker TCEP Solution, Neutral pH; NuPAGE Transfer Buffer; and SuperSignal West Femto were from Thermo Fisher Scientific (Waltham, MA). All other reagents, unless otherwise noted, were obtained from Sigma-Aldrich (St. Louis, MO).

Plasmid cDNA

Plasmid cDNA was obtained from the Virginia G. Piper Center for Personalized Diagnostics' (VGP CPD) plasmid repository, DNASU (Tempe, AZ), and Open Biosystems (Lafayette, CO), and prepared as previously described using the Invitrogen Gateway®-compatible vectors (Thermo Fisher Scientific; Waltham, MA), pJFT7_nHalo_DC and pJFT7_cHalo_DC, with the capturing fusion tag (i.e., HaloTag) at the N- or C-terminus (Saul et al., 2014). Successful cloning of the genes-of-interest was confirmed with Sangar sequencing at DNASU.

NAPPA-SPRi Slide Preparation

A 48 nm layer of gold was deposited via electron beam evaporation on low sodium optical D263 borosilicate slides with an index of refraction of 1.52 (Plexera LLC; Woodinville, WA). The slides were sonicated for 10 min in 0.1 N KOH, 100% methanol, washed three times in 100% ethanol, and then dried with compressed gas. 1 mM amine-terminated polyethylene glycol [HS—$C_{11}$ ($C_2H_4O)_6$—$NH_2$] (Prochimia Surfaces; Poland) was resuspended in ethanol and applied to the slide overnight at 4° C. to create a self-assembled monolayer. To prevent evaporation of the ethanol during the incubation, these slides were placed on upside-down Wheaton® stainless steel 30-slide rack (Capital Scientific, Inc.; Austin, TX) within a plastic Lock & Lock food storage container (Food Storage Mall; China) with ~ 0.5 cm of 100% ethanol on the bottom. The slides were washed three times in 100% ethanol and dried with compressed gas just prior to printing.

The printing master mix included 0.0003% poly-L-lysine (Thermo Fisher Scientific; Waltham, MA), 0.3% DMSO, 250 μM BS3 (Thermo Fisher Scientific; Waltham, MA), 375 μM HaloTag® amine (04) ligand (Promega; Madison, WI), and 0.4 mg/mL plasmid cDNA. The printing master mixture was incubated at 4° C. overnight, then deposited onto the prepared slides with the QArray2 spotter (Molecular Devices, LLC; Sunnyvale, CA) using solid pins.

Target Protein Expression

Slides were blocked with Tris-based SuperBlock (Thermo Fisher Scientific; Waltham, MA) to minimize non-specific binding overnight at 4° C. They were then washed in 1×PBS three times for 2 min each, rocking. The slides were rinsed in water and dried with compressed air. SPRi flow chambers (Plexera; Woodinville, WA) with 30 μL volume were applied onto the slides followed by 1-step human coupled in vitro protein expression mixture according to the manufacturer's instructions (Thermo Fisher Scientific; Waltham, MA). Expression was performed for 1.5 hours at 30° C. and then 30 min at 15° C. Slides were rinsed in 200 μL 1× PBS.

Query Protein Expression

BLNK and BTK had an N-terminal His tag (Sino Biological; Beijing, China) and tested for activity through a functional ELISA and kinase assay tests, respectively. BLNK was expressed in human cells while BTK was expressed in baculovirus insect cells. PIK3CA/PIK3R1 (p110a/p85a) (Thermo Fisher Scientific; Waltham, MA) was expressed in baculovirus insect cells, tested for activity using a kinase assay, and had an N-terminal His tag on PIK3CA. The GTPases, RAC1 and RHOA, were expressed in *Escherichia coli*. Moreover, the proteins were tested for functionality by Dr. Xiaobo Yu (personal communication; National Center for Protein Sciences; Bejing, China) by their ability to bind to known protein partners on NAPPA arrays.

De-Phosphorylation of Target Proteins

Calf intestinal alkaline phosphatase (CIAP) (New England BioLabs; Ipswich, MA) and lambda protein phosphatase (New England BioLabs; Ipswich, MA) were buffer exchanged into 50 mM Tris pH 7.9, 100 mM NaCl, 10 mM $MgCl_2$, 1 mM DTT or 50 mM HEPES pH 7.5, 100 mM NaCl, 2 mM DTT, 0.01% Brij 35, 1 mM MnCl2, respectively (New England BioLabs Ipswich, MA), respectively, using 7 kDa molecular weight cut-off (MWCO) Zeba spin desalting columns (Thermo Fisher Scientific; Waltham, MA). Slides were rinsed in 200 µL 1× NEBuffer 3 and then incubated in 300 units of CIAP at 30° C. for 30 min. Slides were rinsed in 200 µL 1× NEBuffer for PMP supplemented with 1 mM MnCl2. The slides were then incubated three times with 2,000 units of lambda protein phosphatase at 30° C. for 30 min. Slides were rinsed in the same HEPES- or Tris-based buffer that was used for SPRi analyses.

Phosphorylation of Target Proteins with Ramos B Cell Lysate

Ramos RA-1 B cells (ATCC; Manassas, VA) were grown in RPMI-1640 (Thermo Fisher; Waltham, MA) supplemented with 10% HyClone™ fetal bovine serum (GE Healthcare Life Sciences; Logan, UT). Cells were washed twice with ice-cold 1 mM $Na_3 VO_4$ in TBS, then solubilized in 50 mM Tris-HCl (pH 7.7), 0.5% nonidet P-40, 2.5 mM EDTA, 20 mM beta-glycerophosphate, 10 mM NaF, 1 mM $Na_2MoO_4$, 1 mM $Na_3 VO_4$, 0.25 µM PMSF, 1 µM pepstatin, 0.5 µg/mL leupeptin, 10 µg/mL soybean trypsin inhibitor, and 1 µg/mL microcystin-LR. Cells were spun at 4k×g for 5 min and the supernatant stored in single-use aliquots at −80° C. such that the lysate from 20 million cells were in 1 mL of solubilization buffer. Slides were rinsed in 200 µL 50 mM HEPES, 150 mM NaCl, pH 7.4. B cell lysate was buffer exchanged using a 7 kDa MWCO Zeba desalting spin column (Thermo Fisher Scientific; Waltham, MA) into kinase buffer containing 20 mM HEPES, 5 mM MnCl2, 5 mM MgCl2, 0.25 µM PMSF, 0.5 µg/mL leupeptin, 10 µg/mL soybean trypsin inhibitor, 20 mM beta-glycerophosphate, 10 mM NaF, 1 mM $Na_2MoO_4$, 1 mM $Na_3 VO_4$, 500 µM ATP, pH 7.5. Slides were incubated with B cell lysate in kinase buffer for 3 hours at 30° C. Slides were rinsed with the same HEPES- or Tris-based buffer that was used for SPRi analyses, and then analyzed.

Activation of the GTPase Queries, RAC1 and RHOA

Purified GTPases were incubated in 10 mM HEPES, 150 mM NaCl, 5 mM MgCl2, 5 mM EDTA, 1 mM TCEP, pH 7.4, and 1 mM GTPγS or GDP for 1 hour at room temperature to activate or inactivate the GTPases, respectively. Samples were then buffer exchanged into 50 mM HEPES, 150 mM NaCl, 5 mM $MgCl_2$, 1 mM TCEP, pH 7.4, which was the buffer used for SPRi analyses.

NAPPA-SPRi Analyses

The Plexera HT PlexArray instrument was primed three times with filtered and degassed "running buffer" specific to the query (see below).

| | | | | | Buffer conditions used for NAPPA-SPRi | |
|---|---|---|---|---|---|---|
| Query | Flow (µL/sec) | Association (sec) | Dissodation (sec) | Temp° C. | SPR running buffer (bulk) | Additives in sample |
| BLNK | 3 | 300 | 700 | 25 | 50 mM HEPES, 150 mM NaCl, 0.05% Tween-20, pH 7.4 | 1 mM TCEP |
| BTK | 5 | 180 | 400 | 30 | 50 mM Tris-HCl, 150 mM NaCl, 4 mM MgCl2, 0.01% Tween, pH 7.5 | 500 uM ATP, 1 mM TCEP |
| PIK3CA/PIK3R1 | 5 | 180 | 400 | 30 | 50 mM HEPES, 100 mM NaCl, 0.03% Tween, pH 7.5 | 1 mM TCEP, 250 uM ATP |
| RAC1(GDP) | 3 | 300 | 700 | 25 | 50 mM HEPES, 150 mM NaCl, 5 mM MgCl2, 0.05% Tween-20, pH 7.4 | 1 mM TCEP, 1 mM GDP |
| RAC1(GTP) | 3 | 300 | 700 | 25 | 50 mM HEPES, 150 mM NaCl, 5 mM MgCl2, 0.05% Tween-20, pH 7.4 | 1 mM TCEP, 1 mM GTPyS |
| RHOA(GDP) | 3 | 300 | 700 | 25 | 50 mM HEPES, 150 mM NaCl, 5 mM MgCl2, 0.05% Tween-20, pH 7.4 | 1 mM TCEP, 1 mM GDP |
| RHOA(GTP) | 3 | 300 | 700 | 25 | 50 mM HEPES, 150 mM NaCl, 5 mM MgCl2, 0.05% Tween-20, pH 7.4 | 1 mM TCEP, 1 mM GTPyS |

Each slide was then subjected on-line to the following runs, in consecutive order: 0.5% glycerol, 1.0% glycerol, running buffer, protein query, and $5.34\times10^{-8}$ M anti-TP53 D01 monoclonal antibody. Glycerol in running buffer was injected with 100 sec association and 100 sec dissociation each and used to normalize inter- and intra-slide data where the change in refractive index is equal to 0.000565 response units (RU). Kinase query runs were performed at 5 μL/see at 30° C. Running buffer, purified query protein in running buffer, and antibody in running buffer were injected with 180 sec association and 400 sec dissociation. Non-kinase query runs were performed at 3 μL/see at RT. Running buffer, purified query protein in running buffer, and antibody in running buffer were injected with 300 sec association and 700 sec dissociation. Data were acquired in real-time as an AVI video with the Plexera Instrument Control software.

NAPPA-SPRi Data Analyses

Data analyses were performed in three steps. Regions-of-interest in the AVI video format were first identified and analyzed with the Plexera SPR Data Analysis Module software. The in-house software, SPRite, calibrated the data to standard response units (RU), formatted the data to be compatible with Scrubber2, selected the time frame(s) of interest, referenced the binding curves to non-binders, drift corrected the data, and fit the curves using Langmuir kinetic models (with and without mass transport) (see next section). Finally, the curves were assessed by eye. Notably, proteins isoforms with the same name but different sequences (i.e., AKT2, IKBKB, PIK3R1) were counted as different proteins, which included previously-reported interactions where the specific isoform (e.g., PIK3R1 BC030815 or BC094795) was not indicated.

| Binding kinetics and affinities of the BTK and BLNK queries obtained with NAPPA-SPRi | | | | | | |
| --- | --- | --- | --- | --- | --- | --- |
| | BLNK_NP | | | BLNK_LT | | |
| Protein | KD | ka | kd | KD | ka | kd |
| AKT1 | 7.56E−09 | 6.15E+04 | 4.65E−04 | 1.73E−08 | 6.15E+04 | 1.07E−03 |
| AKT2* | 2.77E−08 | 5.81E+04 | 1.61E−03 | 1.90E−08 | 8.02E+04 | 1.52E−03 |
| AKT2** | 2.90E−08 | 6.64E+04 | 1.92E−03 | 2.68E−08 | 6.89E+04 | 1.84E−03 |
| AKT3 | | | | | | |
| ARHGEF7 | | | | | | |
| BCL10 | 2.97E−08 | 5.77E+04 | 1.71E−03 | 1.71E−08 | 6.03E+04 | 1.03E−03 |
| BCL2 | | | | | | |
| BCL2A1 | 1.85E−08 | 4.13E+04 | 7.64E−04 | 1.56E−08 | 7.91E+04 | 1.23E−03 |
| BCL2L1 | 1.62E−08 | 4.44E+04 | 7.19E−04 | 1.46E−08 | 7.22E+04 | 1.06E−03 |
| BLK | | | | | | |
| BLNK | | | | | | |
| BTK | | | | | | |
| CARD11 | 3.34E−08 | 3.78E+04 | 1.26E−03 | 21.7E−08 | 4.88E+04 | 1.06E−03 |
| CD19 | | | | | | |
| CD22 | 1.25E−08 | 8.18E+04 | 1.02E−03 | 1.21E−08 | 7.46E+04 | 9.06E−04 |
| CD72 | 3.02E−08 | 6.19E+04 | 1.87E−03 | 1.60E−08 | 5.54E+04 | 8.85E−04 |
| CD79A | 1.83E−08 | 6.38E+04 | 1.17E−03 | 2.22E−08 | 7.01E+04 | 1.56E−03 |
| CD79B | | | | 4.26E−08 | 5.59E+04 | 2.38E−03 |
| CD81 | 1.98E−08 | 4.46E+04 | 8.86E−04 | 1.99E−08 | 5.89E+04 | 1.17E−03 |
| CDC42 | | | | | | |
| CDKN2A | 1.89E−08 | 4.21E+04 | 7.96E−04 | 2.37E−08 | 5.33E+04 | 1.26E−03 |
| DAPP1 | 1.76E−08 | 5.10E+04 | 9.00E−04 | 2.34E−08 | 6.61E+04 | 1.55E−03 |
| EGR1 | 2.28E−09 | 6.46E+04 | 1.47E−04 | | | |
| ETS1 | 1.10E−08 | 4.36E+04 | 4.77E−04 | 1.83E−08 | 5.50E+04 | 1.01E−03 |
| EZR | | | | | | |
| FCGR2B | | | | | | |
| Fos | | | | | | |
| GRAP2 | | | | | | |
| GRB2 | 1.93E−08 | 5.35E+04 | 1.03E−03 | 1.37E−08 | 4.84E+04 | 6.64E−04 |
| GSK3B | | | | 2.40E−08 | 5.67E+04 | 1.36E−03 |
| HRAS | 1.90E−08 | 4.83E+04 | 5.17E−04 | 1.71E−08 | 5.43E+04 | 9.29E−04 |
| IFITM1 | | | | | | |
| IKBKA | | | | 2.00E−08 | 5.82E+04 | 1.16E−03 |
| IKBKB# | | | | | | |
| IKBKB## | 4.19E−08 | 4.19E+04 | 1.76E−03 | 2.34E−08 | 6.56E+04 | 1.54E−03 |
| IKBKG | 2.40E−08 | 4.75E+04 | 1.14E−03 | 1.80E−08 | 6.22E+04 | 1.12E−03 |
| INPPSD | | | | | | |
| INPPL1 | 2.48E−08 | 5.85E+04 | 1.45E−03 | 1.83E−08 | 5.50E+04 | 1.01E−03 |
| Jun | 7.86E−09 | 3.49E+04 | 2.74E−04 | 2.42E−08 | 6.56E+04 | 1.59E−03 |
| KRAS | 1.37E−08 | 5.19E+04 | 7.12E−04 | 3.19E−08 | 4.42E+04 | 1.41E−03 |
| LAT2 | 1.34E−08 | 5.15E+04 | 6.90E−04 | 1.59E−08 | 6.91E+04 | 1.10E−03 |
| LILRB3 | | | | | | |
| LIME1 | | | | | | |
| LYN | 1.61E−09 | 3.73E+04 | 6.01E−05 | | | |
| MALT1 | 2.74E−08 | 6.55E+04 | 1.79E−03 | 3.45E−08 | 5.86E+04 | 2.03E−03 |
| MAP2K1 | 7.90E−09 | 1.27E+05 | 1.01E−03 | 2.62E−08 | 6.04E+04 | 1.58E−03 |
| MAP2K2 | | | | | | |
| MAP2K3 | | | | | | |
| MAP3K3 | 1.79E−08 | 3.85E+04 | 6.93E−04 | 1.48E−08 | 6.35E+04 | 9.41E−04 |
| MAPK1 | 2.81E−08 | 5.08E+04 | 1.43E−03 | 1.98E−08 | 5.40E+04 | 1.07E−03 |
| MAPK12 | 2.45E−08 | 5.85E+04 | 1.43E−03 | 2.10E−08 | 6.48E+04 | 1.36E−03 |

-continued

| Binding kinetics and affinities of the BTK and BLNK queries obtained with NAPPA-SPRi | | | | | |
|---|---|---|---|---|---|
| MAPK13 | 2.42E−08 | 5.94E+04 | 1.44E−03 | 1.60E−08 | 6.31E+04 | 1.01E−03 |
| MAPK14 | 1.60E−08 | 9.26E+04 | 1.48E−03 | | | |
| MAPK3 | 1.39E−08 | 5.34E+04 | 7.40E−04 | | | |
| MAPK8 | | | | | | |
| MAPK9 | | | | | | |
| MDM2 | | | | | | |
| MYC | 1.19E−08 | 4.57E+04 | 5.43E−04 | 2.12E−08 | 5.43E+04 | 1.15E−03 |
| NCK1 | | | | | | |
| NCKAP1L | 2.58E−08 | 4.88E+04 | 1.26E−03 | 1.96E−08 | 6.03E+04 | 1.18E−03 |
| NFAT5 | 1.68E−08 | 5.84E+04 | 9.82E−04 | 3.51E−08 | 2.53E+04 | 9.24E−04 |
| NFATC1 | 2.59E−08 | 5.28E+04 | 1.37E−03 | 1.77E−08 | 7.15E+04 | 1.27E−03 |
| NFATC4 | | | | 2.02E−08 | 6.75E+04 | 1.36E−03 |
| NFKB1 | 7.21E−09 | 4.69E+04 | 3.38E−04 | | | |
| NFKBIA | 1.39E−08 | 6.08E+04 | 8.45E−04 | 2.06E−08 | 4.52E+04 | 9.31E−04 |
| NFKBIE | 5.78E−09 | 4.62E+04 | 2.67E−04 | 3.12E−08 | 4.17E+04 | 1.30E−03 |
| NRAS | 4.28E−08 | 1.91E+04 | 8.20E−04 | 3.58E−08 | 3.22E+04 | 1.15E−03 |
| PIK3AP1 | 1.34E−08 | 3.75E+04 | 5.02E−04 | 2.01E−08 | 4.79E+04 | 9.60E−04 |
| PIK3CA | 1.30E−08 | 3.80E+04 | 6.83E−04 | 1.89E−08 | 5.35E+04 | 1.01E−03 |
| PIK3CB | | | | | | |
| PIK3CG | 1.63E−08 | 4.73E+04 | 7.27E−04 | | | |
| PIK3R1⁻ | 2.20E−08 | 4.29E+04 | 9.45E−04 | 1.82E−08 | 4.80E+04 | 8.75E−04 |
| PIK3R1⁻⁻ | | | | | | |
| PIK3R2 | | | | | | |
| PIK3R3 | | | | | | |
| PIK3R5 | | | | | | |
| PLCG2 | | | | | | |
| PPP3CA | | | | | | |
| PPP3CB | | | | | | |
| PPP3R1 | | | | | | |
| PPP3R2 | | | | | | |
| PRKCA | | | | | | |
| PRKCB | | | | | | |
| PTEN | 1.55E−08 | 9.05E+04 | 1.40E−03 | 2.59E−08 | 6.32E+04 | 1.64E−03 |
| PTPN6 | 2.14E−08 | 5.89E+04 | 1.26E−03 | 2.70E−08 | 5.71E+04 | 1.54E−03 |
| RAC1 | 6.85E−09 | 5.14E+04 | 3.52E−04 | | | |
| RAC2 | | | | | | |
| RAC3 | | | | | | |
| Raf1 | | | | | | |
| RAP1B | 1.24E−08 | 7.19E+04 | 8.92E−04 | 3.97E−08 | 5.00E+04 | 1.99E−03 |
| RAP2A | 2.00E−08 | 5.58E+04 | 1.11E−03 | 4.22E−08 | 4.77E+04 | 2.01E−03 |
| RAP2C | 1.40E−08 | 5.66E+04 | 7.93E−04 | 1.97E−08 | 5.33E+04 | 1.05E−03 |
| RasGRP3 | | | | | | |
| RASSF5 | | | | | | |
| RELA | | | | | | |
| RHOA | 2.00E−08 | 4.64E+04 | 9.30E−04 | 1.71E−08 | 6.32E+04 | 1.08E−03 |
| SOS1 | 5.87E−09 | 5.26E+04 | 3.09E−04 | 2.44E−08 | 3.17E+04 | 7.73E−04 |
| SOS2 | | | | | | |
| SYK | | | | 2.84E−08 | 5.86E+04 | 1.66E−03 |
| TEC | | | | | | |
| VAV1 | | | | 5.30E−08 | 3.93E+04 | 2.08E−03 |
| VAV2 | 1.63E−08 | 4.23E+04 | 6.89E−04 | 4.88E−08 | 4.19E+04 | 2.04E−03 |
| VAV3 | 1.92E−08 | 4.83E+04 | 9.28E−04 | 4.46E−08 | 4.87E+04 | 2.17E−03 |

| | BTK_NP | | | BTK_LT | | |
|---|---|---|---|---|---|---|
| Protein | KD | ka | kd | KD | ka | kd |
| AKT1 | 5.11E−08 | 5.35E+04 | 2.73E−03 | 1.19E−07 | 2.65E+04 | 3.21E−03 |
| AKT2* | 3.56E−08 | 7.28E+04 | 2.59E−03 | 1.89E−08 | 1.12E+05 | 2.11E−03 |
| AKT2** | 1.78E−08 | 1.07E+05 | 1.90E−03 | 2.61E−08 | 1.17E+05 | 3.04E−03 |
| AKT3 | 4.07E−08 | 5.85E+04 | 2.38E−03 | 1.99E−07 | 1.31E+04 | 2.60E−03 |
| ARHGEF7 | 1.37E−07 | 1.70E+04 | 2.33E−03 | 6.61E−03 | 2.15E−04 | 1.42E−03 |
| BCL10 | 8.91E−08 | 3.57E+04 | 3.19E−03 | 3.14E−07 | 9.61E+03 | 3.01E−03 |
| BCL2 | 2.09E−08 | 1.33E+05 | 2.77E−03 | 1.75E−09 | 4.60E+03 | 3.06E−06 |
| BCL2A1 | 6.66E−08 | 5.94E+04 | 3.96E−03 | 5.56E−08 | 4.60E+04 | 2.56E−03 |
| BCL2L1 | 3.66E−08 | 7.71E+04 | 2.82E−03 | 2.02E−08 | 7.44E+04 | 1.50E−03 |
| BLK | 5.30E−08 | 6.09E+04 | 3.28E−03 | 4.54E−08 | 6.75E+04 | 3.06E−03 |
| BLNK | 7.51E−08 | 3.23E+04 | 2.42E−03 | 1.10E−07 | 1.88E+04 | 2.07E−03 |
| BTK | 7.94E−08 | 2.36E+04 | 1.88E−03 | 9.24E−08 | 1.02E+04 | 9.41E−04 |
| CARD11 | 1.80E−07 | 1.55E+04 | 2.78E−03 | 2.21E−08 | 1.19E+05 | 2.62E−03 |
| CD19 | 1.48E−07 | 4.92E+04 | 7.28E−03 | 4.41E−08 | 4.01E+04 | 1.77E−03 |
| CD22 | 2.65E−08 | 1.03E+05 | 2.72E−03 | 8.82E−08 | 1.26E+05 | 3.56E−03 |
| CD72 | | | | | | |
| CD79A | 2.42E−08 | 9.11E+04 | 2.21E−03 | 1.28E−07 | 3.00E+04 | 3.83E−03 |
| CD79B | 2.65E−08 | 8.90E+04 | 2.36E−03 | 5.71E−08 | 2.74E+04 | 1.56E−03 |
| CD81 | | | | | | |

-continued

| Binding kinetics and affinities of the BTK and BLNK queries obtained with NAPPA-SPRi | | | | | | |
|---|---|---|---|---|---|---|
| CDC42 | | | | 8.23E−07 | 1.91E+03 | 1.57E−03 |
| CDKN2A | | | | | | |
| DAPP1 | | | | | | |
| EGR1 | | | | | | |
| ETS1 | | | | 1.52E−07 | 1.36E+04 | 2.06E−03 |
| EZR | 3.28E−08 | 8.02E+04 | 2.63E−03 | 5.74E−08 | 4.65E+04 | 2.67E−03 |
| FCGR2B | 2.45E−08 | 8.19E+04 | 2.01E−03 | 4.38E−08 | 4.02E+04 | 1.76E−03 |
| Fos | 8.79E−08 | 3.05E+04 | 2.68E−03 | 8.76E−08 | 3.39E+04 | 2.96E−03 |
| GRAP2 | 3.16E−08 | 6.57E+04 | 2.08E−03 | 9.33E−08 | 2.80E+04 | 2.15E−03 |
| GRB2 | 2.96E−08 | 6.15E+04 | 1.82E−03 | 1.65E−08 | 1.47E+05 | 2.42E−03 |
| GSK3B | 5.21E−08 | 4.72E+04 | 2.46E−03 | 5.08E−08 | 2.40E+04 | 2.18E−03 |
| HRAS | 5.49E−08 | 5.42E+04 | 2.98E−03 | 1.70E−08 | 3.54E+03 | 6.01E−05 |
| IFITM1 | 8.05E−08 | 4.61E+04 | 3.70E−03 | 7.83E−08 | 3.45E+04 | 2.73E−03 |
| IKBKA | 3.96E−08 | 5.95E+04 | 2.37E−03 | 4.39E−08 | 5.30E+04 | 2.33E−03 |
| IKBKB# | 4.70E−08 | 5.85E+04 | 2.75E−03 | 5.13E−08 | 5.16E+04 | 2.64E−03 |
| IKBKB## | 9.75E−08 | 3.96E+04 | 3.86E−03 | 3.83E−08 | 4.41E+04 | 1.69E−03 |
| IKBKG | 4.41E−08 | 6.03E+04 | 2.66E−03 | 2.00E−08 | 6.83E+04 | 1.37E−03 |
| INPP5D | 4.65E−08 | 6.55E+04 | 3.05E−03 | 3.62E−08 | 7.61E+04 | 2.76E−03 |
| INPPL1 | 1.23E−07 | 5.81E+04 | 7.13E−03 | 6.03E−03 | 1.38E+04 | 8.31E−04 |
| Jun | 2.66E−08 | 8.64E+04 | 2.29E−03 | 8.41E−08 | 3.61E+04 | 3.04E−03 |
| KRAS | | | | | | |
| LAT2 | | | | | | |
| LILRB3 | | | | 5.74E−07 | 2.54E+03 | 1.46E−03 |
| LIME1 | 5.33E−08 | 4.63E+04 | 2.47E−03 | 2.66E−07 | 1.11E+04 | 2.54E−03 |
| LYN | | | | | | |
| MALT1 | 8.17E−08 | 2.91E+04 | 2.38E−03 | 1.20E−05 | 1.99E+03 | 2.40E−03 |
| MAP2K1 | | | | | | |
| MAP2K2 | | | | 9.06E−08 | 3.23E+04 | 2.92E−03 |
| MAP2K3 | 3.94E−08 | 8.76E+04 | 3.45E−03 | 3.58E−08 | 6.94E+04 | 2.49E−03 |
| MAP3K3 | | | | | | |
| MAPK1 | 6.36E−08 | 9.00E+04 | 5.73E−03 | 6.94E−08 | 3.76E+04 | 2.61E−03 |
| MAPK12 | 4.24E−08 | 6.18E+04 | 2.62E−03 | 1.62E−07 | 1.65E+04 | 2.66E−03 |
| MAPK13 | 3.90E−08 | 4.64E+04 | 1.81E−03 | 6.83E−08 | 4.39E+04 | 3.00E−03 |
| MAPK14 | 4.62E−08 | 6.65E+04 | 3.08E−03 | 3.06E−08 | 7.43E+04 | 2.28E−03 |
| MAPK3 | 3.68E−08 | 7.11E+04 | 2.62E−03 | 1.26E−07 | 2.42E+04 | 3.04E−03 |
| MAPK8 | 2.93E−08 | 7.46E+04 | 2.19E−03 | 9.48E−08 | 2.48E+04 | 2.35E−03 |
| MAPK9 | 9.09E−08 | 1.85E+04 | 1.68E−03 | 1.09E−08 | 1.73E−04 | 1.89E−04 |
| MDM2 | 4.93E−08 | 4.61E+04 | 2.27E−03 | 4.02E−08 | 5.61E+04 | 2.25E−03 |
| MYC | 9.50E−08 | 4.99E+04 | 4.74E−03 | 4.56E−08 | 6.05E+04 | 2.76E−03 |
| NCK1 | 9.61E−08 | 7.14E+04 | 2.58E−03 | 3.10E−08 | 7.47E+04 | 2.31E−03 |
| NCKAP1L | 3.33E−08 | 7.20E+04 | 2.40E−03 | 2.76E−08 | 7.73E+04 | 2.14E−03 |
| NFAT5 | 4.35E−08 | 7.60E+04 | 3.30E−03 | 1.34E−07 | 1.98E+04 | 2.66E−03 |
| NFATC1 | 2.61E−08 | 1.13E+05 | 2.94E−03 | | | |
| NFATC4 | | | | | | |
| NFKB1 | | | | | | |
| NFKBIA | | | | | | |
| NFKBIE | 2.95E−08 | 7.43E+04 | 2.19E−03 | 6.05E−07 | 6.79E+03 | 4.11E−03 |
| NRAS | | | | | | |
| PIK3AP1 | | | | | | |
| PIK3CA | | | | | | |
| PIK3CB | 3.24E−08 | 5.80E+04 | 1.88E−03 | 4.04E−08 | 4.23E+04 | 1.71E−03 |
| PIK3CG | 2.11E−07 | 1.80E+04 | 3.79E−03 | 6.29E−08 | 2.42E+04 | 1.53E−03 |
| PIK3R1⁻ | 2.90E−08 | 8.57E+04 | 2.49E−03 | 1.97E−08 | 1.26E+05 | 2.49E−03 |
| PIK3R1⁻⁻ | 5.94E−08 | 5.40E+04 | 3.20E−03 | 4.90E−08 | 5.90E+04 | 2.89E−03 |
| PIK3R2 | 1.45E−07 | 2.31E+04 | 3.35E−03 | 1.65E−07 | 1.11E+04 | 1.83E−03 |
| PIK3R3 | 4.54E−08 | 5.07E+04 | 2.30E−03 | 2.43E−09 | 6.99E+04 | 1.70E−04 |
| PIK3R5 | 3.62E−08 | 6.87E+04 | 2.48E−03 | 5.36E−08 | 4.57E+04 | 2.50E−03 |
| PLCG2 | 3.04E−08 | 4.57E+04 | 3.68E−03 | 8.04E−08 | 2.58E+04 | 2.08E−03 |
| PPP3CA | 1.04E−07 | 3.78E+04 | 3.92E−03 | 8.17E−08 | 2.89E+04 | 2.37E−03 |
| PPP3CB | 7.21E−08 | 3.41E+04 | 2.46E−03 | 9.78E−08 | 2.38E+04 | 2.32E−03 |
| PPP3R1 | 3.10E−08 | 5.92E+04 | 2.14E−03 | 3.95E−08 | 3.76E+04 | 1.48E−03 |
| PPP3R2 | 3.73E−08 | 7.54E+04 | 2.81E−03 | 2.86E−08 | 7.67E+04 | 2.20E−03 |
| PRKCA | 3.29E−07 | 7.39E+03 | 2.43E−03 | | | |
| PRKCB | 4.63E−08 | 7.50E+04 | 3.47E−03 | 5.12E−08 | 4.16E+04 | 2.13E−03 |
| PTEN | | | | | | |
| PTPN6 | | | | | | |
| RAC1 | | | | | | |
| RAC2 | 2.94E−06 | 3.75E+00 | 1.10E−05 | 1.42E−06 | 1.86E+03 | 2.65E−03 |
| RAC3 | | | | 1.28E−08 | 2.35E+04 | 3.01E−04 |
| Raf1 | 6.23E−07 | 4.06E+03 | 2.53E−03 | 1.52E−07 | 5.25E+03 | 7.99E−04 |
| RAP1B | 6.26E−08 | 2.74E+04 | 1.71E−03 | 3.20E−08 | 3.47E+04 | 1.11E−03 |
| RAP2A | 1.05E−07 | 2.16E+04 | 2.26E−03 | 1.16E−09 | 7.89E+04 | 9.14E−05 |
| RAP2C | 6.21E−08 | 7.36E+04 | 4.57E−03 | 3.19E−08 | 6.28E+04 | 2.01E−03 |
| RasGRP3 | 7.94E−08 | 4.11E+04 | 3.26E−03 | 7.97E−08 | 4.27E+04 | 3.40E−03 |
| RASSF5 | 9.52E−08 | 3.58E+04 | 3.50E−03 | 3.75E−08 | 3.97E+04 | 1.49E−03 |
| RELA | 4.72E−08 | 7.21E+04 | 3.41E−03 | 4.10E−08 | 3.88E+04 | 1.59E−03 |
| RHOA | 3.31E−08 | 6.40E+04 | 2.11E−03 | 5.09E−08 | 3.56E+04 | 2.02E−03 |

-continued

| Binding kinetics and affinities of the BTK and BLNK queries obtained with NAPPA-SPRi | | | | | |
|---|---|---|---|---|---|
| SOS1 | 5.45E−08 | 5.36E+04 | 2.92E−03 | 1.27E−07 | 1.71E+04 | 2.16E−03 |
| SOS2 | | | | 1.54E−07 | 1.22E+04 | 1.88E−03 |
| SYK | 4.61E−08 | 7.25E+04 | 3.34E−03 | 1.85E−08 | 8.39E+04 | 1.55E−03 |
| TEC | 9.25E−08 | 2.89E+04 | 2.68E−03 | 4.28E−08 | 4.15E+04 | 1.78E−03 |
| VAV1 | 3.80E−09 | 1.41E+04 | 5.35E−05 | 1.48E−08 | 1.57E+04 | 2.47E−04 |
| VAV2 | 3.98E−08 | 7.82E+04 | 3.11E−03 | 2.00E−08 | 8.52E+04 | 1.70E−03 |
| VAV3 | 5.55E−08 | 7.35E+04 | 4.08E−03 | | | |

Reference Sequence ID = *BC063421, **BC120994, #BC006231, ##BC108694, ⁻BC030815, ⁻⁻BC094795
NP = target proteins are Not Phosphorylated.
LT = target proteins are Lysate-Treated.

| Binding kinetics and affinities of the PI3K query obtained with NAPPA-SPRi | | | | | | |
|---|---|---|---|---|---|---|
| | PI3K_NP | | | PI3K_LT | | |
| Protein | KD | ka | kd | KD | ka | kd |
| AKT1 | 6.81E−09 | 5.85E+05 | 3.99E−03 | 1.31E−09 | 1.99E+05 | 2.61E−04 |
| AKT2* | 5.20E−09 | 1.98E+05 | 1.03E−03 | | | |
| AKT2** | 1.24E−08 | 4.54E+05 | 5.63E−03 | 5.69E−10 | 2.99E+05 | 1.70E−04 |
| BCL2A1 | 7.63E−09 | 5.76E−05 | 4.40E−03 | 1.02E−09 | 1.66E+05 | 1.69E−04 |
| BLK | | | | 1.03E−08 | 2.40E+05 | 2.47E−03 |
| CD22 | 7.97E−09 | 5.90E+05 | 4.70E−03 | | | |
| CD79A | 1.89E−09 | 4.04E+05 | 7.65E−04 | | | |
| ETS1 | 1.32E−08 | 7.88E+04 | 1.04E−03 | 2.88E−08 | 7.43E+04 | 2.14E−03 |
| HRAS | 1.38E−08 | 3.32E+05 | 4.57E−03 | | | |
| IKBKA | 4.58E−09 | 1.98E+05 | 9.09E−04 | | | |
| IKBKB## | 1.62E−08 | 3.35E+05 | 5.44E−03 | | | |
| IKBKG | 9.07E−09 | 4.93E+05 | 4.47E−03 | | | |
| INPPL1 | 1.59E−08 | 2.92E+05 | 4.64E−03 | | | |
| KRAS | 3.59E−08 | 5.37E+04 | 1.93E−03 | | | |
| LAT2 | 1.48E−09 | 1.17E+05 | 1.69E−04 | 1.98E−08 | 1.03E+05 | 2.04E−03 |
| MAP3K3 | 1.72E−09 | 8.77E+04 | 1.51E−04 | | | |
| MAPK1 | 6.38E−09 | 5.81E+05 | 3.71E−03 | 5.58E−09 | 4.06E+05 | 2.26E−03 |
| MAPK12 | 9.95E−09 | 4.20E+05 | 4.18E−03 | | | |
| MAPK13 | 1.03E−08 | 6.30E+05 | 6.51E−03 | | | |
| MDM2 | 8.70E−09 | 6.25E+05 | 5.44E−03 | | | |
| MYC | 1.31E−08 | 4.74E+05 | 6.19E+03 | 4.24E−09 | 3.44E+05 | 1.46E−03 |
| NCKAP1L | 1.01E−08 | 5.01E+05 | 5.03E−03 | | | |
| PIK3AP1 | 4.15E−10 | 1.94E+05 | 8.06E−05 | 1.64E−08 | 2.05E+06 | 3.37E−02 |
| PIK3CA | 7.45E−09 | 1.50E+05 | 1.12E−03 | 1.16E−08 | 1.18E+05 | 1.38E−03 |
| PIK3R1⁻⁻ | 2.43E−09 | 3.67E+05 | 8.89E−04 | 8.69E−10 | 1.49E+06 | 1.30E−03 |
| PLCG2 | 1.14E−08 | 6.60E+05 | 7.54E−03 | | | |
| PPP3CB | 1.95E−09 | 2.30E+05 | 4.49E−04 | | | |
| PTEN | 1.35E−08 | 2.63E+05 | 3.55E−03 | 7.13E−10 | 3.93E+05 | 2.80E−04 |
| PTPN6 | 8.85E−09 | 2.98E+05 | 2.64E−03 | 5.44E−10 | 5.88E+05 | 3.20E−04 |
| RAC1 | 4.20E−09 | 8.52E+04 | 3.58E−04 | | | |
| RAP2C | 8.11E−09 | 1.08E+05 | 8.74E−04 | 1.64E−08 | 4.33E+06 | 7.11E−02 |
| RELA | 1.79E−08 | 3.51E+05 | 6.27E−03 | 1.27E−09 | 6.70E+05 | 8.54E−04 |
| RHOA | 7.18E−09 | 3.32E+05 | 2.38E−03 | 6.66E−10 | 3.75E+05 | 2.50E−04 |
| VAV2 | 1.00E−08 | 4.55E+05 | 4.57E−03 | | | |
| VAV3 | 4.12E−09 | 2.32E+05 | 9.55E−04 | | | |

Reference Sequence ID = *BC063421, **BC120994, #BC006231, ##BC108694, ⁻BC030815, ⁻⁻BC094795

NP = target proteins are Not Phosphorylated.

LT = target proteins are Lysate-Treated.

| | Binding kinetics and affinities of the RAC1 query obtained with NAPPA-SPRi | | | | | |
|---|---|---|---|---|---|---|
| | RAC1(GDP)_NP | | | RAC1(GDP)_LT | | |
| Protein | KD | ka | kd | KD | ka | kd |
| AKT1 | | | | | | |
| AKT2* | | | | 5.73E−08 | 4.13E+04 | 1.54E−08 |
| AKT2** | | | | | | |
| AKT3 | 5.99E−09 | 2.17E+04 | 1.30E−03 | 2.44E−08 | 2.32E+04 | 5.67E−04 |
| BCL10 | 5.15E−08 | 2.38E+04 | 1.22E−03 | 6.09E−08 | 3.02E+04 | 1.84E−03 |
| BCL2 | | | | | | |
| BCL2A1 | | | | 5.26E−08 | 1.95E+04 | 1.03E−03 |
| BCL2L1 | 8.34E−08 | 1.89E+04 | 1.58E−03 | 3.01E−08 | 4.19E+04 | 1.26E−03 |
| BLK | | | | | | |
| BLNK | 4.38E−09 | 1.40E+04 | 6.14E−05 | 4.18E−09 | 2.18E+04 | 9.12E−05 |
| CARD11 | 3.50E−09 | 1.75E+04 | 6.17E−04 | 1.06E−08 | 3.18E+04 | 9.36E−04 |
| CD13 | 6.49E−08 | 1.82E+04 | 1.18E−03 | 2.65E−08 | 3.31E+04 | 8.78E−04 |
| CD22 | 4.46E−08 | 2.51E+04 | 1.12E−03 | 2.93E−08 | 3.16E+04 | 9.26E−04 |
| CD72 | | | | | | |
| CD79A | | | | | | |
| CD79B | | | | | | |
| CD81 | 3.49E−08 | 1.63E+04 | 3.69E−04 | 2.85E−08 | 2.59E+04 | 7.36E−04 |
| CDC42 | | | | | | |
| CDXN2A | 7.71E−08 | 1.81E+04 | 1.40E−03 | 7.88E−08 | 2.50E+04 | 1.97E−03 |
| DAPP1 | | | | | | |
| EGR1 | | | | 4.99E−09 | 2.62E+04 | 1.31E−04 |
| ETS1 | 9.49E−08 | 1.65E+04 | 1.76E−03 | 6.15E−08 | 1.99E+04 | 1.22E−03 |
| EZR | 5.79E−08 | 6.70E+04 | 3.88E−03 | 3.42E−08 | 3.08E+04 | 1.67E−03 |
| FCGR2B | | | | | | |
| Fos | | | | 1.02E−08 | 3.33E+04 | 3.41E−04 |
| GRAP2 | | | | | | |
| GRB2 | 4.26E−08 | 1.66E+04 | 7.08E−04 | 1.72E−08 | 2.74E+04 | 4.70E−04 |
| GSK3B | 1.12E−07 | 1.07E+04 | 1.20E−03 | 6.04E−08 | 4.35E+04 | 2.63E−03 |
| HRAS | 5.98E−08 | 2.80E+04 | 1.68E−03 | 4.22E−08 | 4.44E+04 | 1.87E−03 |
| IKBKA | 1.39E−07 | 2.00E+04 | 2.75E−03 | 6.55E−08 | 2.01E+04 | 1.32E−03 |
| IKBKB# | | | | | | |
| IKBKB## | 4.53E−08 | 2.63E+04 | 1.19E−03 | 2.60E−08 | 4.16E+04 | 1.21E−03 |
| IKBKG | 9.38E−08 | 1.53E+04 | 1.43E−03 | 5.70E−08 | 2.73E+04 | 1.56E−03 |
| INPPSD | | | | | | |
| INPPL1 | 6.69E−08 | 1.83E+04 | 1.22E−03 | 3.72E−08 | 3.05E+04 | 1.13E−03 |
| Jun | 4.12e−08 | 1.87E+04 | 7.68E−04 | 4.29E−08 | 2.38E+04 | 1.01E−03 |
| KRAS | 6.42E−08 | 2.28E+04 | 1.40E−03 | 4.53E−08 | 2.79E+04 | 1.26E−03 |
| LAT2 | 1.40E−07 | 1.74E+04 | 2.43E−03 | 6.14E−08 | 2.30E+04 | 1.41E−03 |
| LILRB3 | | | | | | |
| LYN | 1.34E−08 | 1.80E+04 | 2.41E−04 | 8.84E−08 | 9.33E+03 | 8.24E−04 |
| MALT1 | | | | | | |
| MAP2K1 | | | | | | |
| MAP2K2 | 3.40E−08 | 1.28E+04 | 4.36E−04 | 2.03E−08 | 2.24E+04 | 4.56E−04 |
| MAP2K3 | 1.15E−07 | 1.76E+04 | 2.03E−03 | 3.96E−08 | 2.25E+04 | 8.90E−04 |
| MAP3K3 | 1.89E−07 | 1.40E+04 | 2.53E−03 | 8.91E−08 | 2.08E+04 | 1.85E−03 |
| MAPK1 | 4.01E−08 | 2.70E+04 | 1.08E−03 | 1.83E−08 | 3.74E+04 | 6.85E−04 |
| MAPK12 | 1.10E−07 | 1.63E+04 | 1.78E−03 | 5.73E−08 | 2.76E+04 | 1.58E−03 |
| MAPK13 | 5.21E−08 | 2.45E+04 | 1.28E−03 | 8.77E−08 | 3.96E+04 | 1.49E−03 |
| MAPK14 | 7.07E−08 | 1.51E+04 | 1.07E−03 | 5.09E−08 | 3.66E+04 | 1.06E−03 |
| MAPK3 | 8.99E−08 | 8.95E+03 | 8.04E−04 | 4.63E−08 | 2.08E+04 | 9.64E−04 |
| MAPK8 | | | | | | |
| MAPK9 | | | | 3.74E−08 | 3.02E+04 | 1.13E−03 |
| MDM2 | 3.04E−07 | 5.06E+03 | 1.55E−03 | 4.90E−08 | 2.30E+04 | 1.12E−03 |
| MYC | 4.54E−08 | 2.20E+04 | 3.96E−04 | 3.78E−08 | 2.79E+04 | 1.05E−03 |
| NCK1 | 8.74E−09 | 1.24E+04 | 1.09E−03 | 3.05E−08 | 3.96E+04 | 1.21E−09 |
| NCKAP1L | 4.37E−08 | 2.13E+04 | 9.31E−04 | 3.02E−08 | 3.40E+04 | 1.03E−03 |
| NFAT5 | 4.76E−08 | 8.11E+03 | 3.86E−04 | 3.17E−08 | 1.88E+04 | 3.96E−04 |
| NFATC1 | 9.79E−08 | 1.17E+04 | 1.15E−03 | 5.12E−08 | 3.26E−04 | 1.67E−03 |
| NFATC3 | | | | | | |
| NFATC4 | | | | | | |
| NFKB1 | | | | 4.62E−08 | 1.58E+04 | 7.30E−04 |
| NFKBIA | 5.51E−08 | 5.38E+04 | 2.96E−03 | 3.75E−08 | 1.26E+05 | 4.73E−03 |
| NFKBIB | 1.41E−07 | 8.80E+03 | 1.24E−03 | 1.24E−07 | 1.47E+04 | 1.02E−03 |
| NFKBIE | 2.09E−07 | 8.46E+03 | 1.77E−03 | | | |
| NRAS | 1.89E−08 | 1.98E+04 | 3.73E−04 | 5.36E−12 | 2.50E+08 | 1.34E−03 |
| PIK3AP1 | 4.01E−08 | 1.42E+04 | 5.70E−04 | 5.97E−08 | 2.24E+04 | 1.34E−03 |
| PIK3CA | 3.01E−08 | 2.72E+04 | 8.20E−04 | 3.31E−08 | 2.99E+04 | 9.31E−04 |
| PIK3CB | | | | | | |
| PIK3CG | 1.16E−07 | 9.89E+03 | 1.15E−03 | 4.25E−08 | 2.93E+04 | 1.25E−03 |
| PIK3R1⁻ | 4.23E−08 | 1.97E+04 | 8.34E−04 | 3.16E−08 | 3.58E+04 | 1.07E−03 |
| PIK3R2 | | | | | | |
| PIK3R3 | 2.37E−07 | 1.09E+04 | 2.59E−03 | 4.58E−08 | 6.04E+04 | 2.77E−03 |
| PIK3R5 | 1.66E−08 | 1.55E+04 | 2.58E−04 | 4.40E−09 | 3.02E+04 | 1.33E−04 |
| PPP3CB | | | | 1.12E−08 | 2.26E+04 | 2.54E−04 |
| PPP3R1 | 9.98E−08 | 1.24E+04 | 1.24E−03 | 3.26E−08 | 3.44E+04 | 1.12E−03 |

-continued

| Binding kinetics and affinities of the RAC1 query obtained with NAPPA-SPRi | | | | | | |
|---|---|---|---|---|---|---|
| PRKCB | 5.05E−08 | 1.24E+04 | 6.25E−04 | 1.03E−08 | 3.75E+04 | 3.86E−04 |
| PTEN | | | | | | |
| PTPN6 | 8.27E−08 | 1.85E+04 | 1.53E−03 | 3.78E−08 | 3.30E+04 | 1.25E−03 |
| RAC1 | | | | 6.51E−09 | 1.87E+04 | 1.22E−04 |
| RAC3 | 1.26E−07 | 1.32E+04 | 1.66E−08 | 4.07E−08 | 4.40E+04 | 1.73E−03 |
| RAP1B | 9.49E−08 | 1.98E+04 | 1.88E−03 | 1.40E−08 | 4.73E+04 | 6.60E−04 |
| RAP2A | 5.54E−08 | 1.90E+04 | 1.05E−03 | 3.39E−03 | 3.19E+04 | 1.08E−03 |
| RAP2C | 3.90E−08 | 2.61E+04 | 1.02E−03 | 7.08E−09 | 4.09E+04 | 2.89E−04 |
| RasGRP3 | 2.77E−07 | 1.20E+04 | 2.33E−03 | 4.99E−08 | 1.96E+04 | 9.75E−04 |
| RASSF5 | | | | | | |
| RELA | | | | | | |
| RHOA | 1.65E−07 | 1.15E+04 | 1.90E−03 | 4.55E−08 | 3.29E+04 | 1.50E−03 |
| SOS1 | | | | 6.14E−08 | 2.08E+04 | 1.28E−03 |
| SOS2 | | | | 1.19E−09 | 2.40E+04 | 2.86E−05 |
| SYK | 2.84E−08 | 1.65E+04 | 4.68E−04 | 2.32E−08 | 3.82E+04 | 8.88E−04 |
| TEC | 5.24E−08 | 1.45E+04 | 7.61E−04 | | | |
| TP53 | | | | | | |
| VAV1 | 3.48E−07 | 7.90E+03 | 2.75E−03 | 5.55E−08 | 2.30E+04 | 1.28E−03 |
| VAV2 | 2.57E−08 | 2.48E+04 | 6.38E−04 | 1.89E−08 | 2.47E+04 | 4.68E−04 |
| VAV3 | | | | | | |

| Protein | RAC1(GTP)_NP | | | RAC1(GTP)_LT | | |
|---|---|---|---|---|---|---|
| | KD | ka | kd | KD | ka | kd |
| AKT1 | 1.12E−07 | 7.87E+08 | 8.84E+01 | 7.62E−08 | 5.10E+05 | 3.99E−02 |
| AKT2* | 1.21E−07 | 6.46E+01 | 7.82E+01 | 6.23E−08 | 1.62E+09 | 1.01E+02 |
| AKT2** | 1.12E−07 | 4.16E+07 | 4.68E+00 | | | |
| AKT3 | 1.03E−07 | 5.22E+08 | 5.39E+01 | 8.49E−08 | 2.43E+04 | 2.06E−03 |
| BCL10 | 5.52E−08 | 5.98E+07 | 3.54E+00 | 1.40E−07 | 1.21E+09 | 1.69E+02 |
| BCL2 | 1.13E−07 | 3.13E+04 | 3.55E−03 | | | |
| BCL2A1 | 1.28E−07 | 4.43E+08 | 5.67E+01 | 7.39E−08 | 2.27E+05 | 1.68E−02 |
| BCL2L1 | 1.16E−07 | 3.32E+09 | 3.86E+02 | 4.69E−08 | 5.05E+04 | 2.37E−03 |
| BLK | 4.93E−08 | 2.65E+05 | 1.31E+02 | | | |
| BLNK | 8.55E−08 | 1.65E+08 | 1.44E+01 | 4.41E−08 | 3.53E+04 | 2.44E−03 |
| CARD11 | 6.84E−08 | 1.50E+09 | 1.02E+02 | 1.11E−07 | 1.32E+05 | 1.47E−02 |
| CD13 | 7.06E−09 | 1.09E+09 | 7.68E+01 | 1.02E−07 | 3.87E+04 | 3.94E−03 |
| CD22 | 6.79E−08 | 2.50E+08 | 1.70E+01 | 9.51E−08 | 3.37E+05 | 3.20E+02 |
| CD72 | 1.22E−07 | 3.19E+06 | 3.90E−01 | | | |
| CD79A | 3.63E−07 | 3.57E+08 | 1.30E+02 | | | |
| CD79B | 1.30E−07 | 2.23E+09 | 2.89E+02 | 6.00E−08 | 5.77E+04 | 3.46E−03 |
| CD81 | 6.14E−08 | 7.25E+08 | 4.48E+01 | 6.77E−08 | 1.75E+05 | 1.18E−02 |
| CDC42 | 1.18E−07 | 4.63E+09 | 5.48E+02 | | | |
| CDXN2A | 1.16E−07 | 3.44E+09 | 4.00E+02 | 1.02E−07 | 6.59E+04 | 6.73E−03 |
| DAPP1 | 1.04E−07 | 4.17E+08 | 4.35E+01 | 1.29E−07 | 9.22E+05 | 4.14E−02 |
| EGR1 | 8.05E−08 | 3.99E+06 | 3.21E−01 | 1.27E−07 | 8.17E+06 | 1.03E+00 |
| ETS1 | 7.92E−08 | 2.39E+09 | 1.89E+02 | 3.38E−08 | 3.82E+04 | 1.29E−03 |
| EZR | 7.53E−08 | 4.10E+09 | 3.09E+02 | 6.18E−08 | 9.36E+05 | 5.91E−02 |
| FCGR2B | 7.45E−08 | 6.43E−08 | 4.83E+01 | | | |
| Fos | 1.03E−07 | 3.42E+09 | 3.53E+02 | 7.59E−08 | 3.55E+04 | 2.69E−03 |
| GRAP2 | 7.88E−08 | 3.66E+04 | 2.88E−03 | | | |
| GRB2 | 8.65E−08 | 7.95E+02 | 6.88E+02 | 8.71E−08 | 3.42E+05 | 2.98E−02 |
| GSK3B | 7.56E−08 | 6.16E−06 | 4.65E−01 | 1.06E−07 | 3.92E+04 | 4.16E−03 |
| HRAS | 8.22E−08 | 1.52E+09 | 1.25E+02 | 1.10E−07 | 2.59E+03 | 2.85E+02 |
| IKBKA | 7.24E−08 | 1.78E+07 | 1.29E+00 | 5.16E−08 | 7.05E+05 | 6.45E−02 |
| IKBKB# | 8.18E−08 | 4.56E+09 | 3.73E+02 | 5.65E−08 | 4.42E+04 | 2.50E−03 |
| IKBKB## | 8.30E−08 | 3.37E+07 | 2.80E+00 | 7.07E−08 | 4.03E+04 | 2.85E−03 |
| IKBKG | 7.82E−06 | 1.24E+09 | 9.66E+01 | 7.65E−06 | 2.36E+04 | 1.50E−03 |
| INPPSD | 5.74E−08 | 1.38E+06 | 7.93E−02 | | | |
| INPPL1 | 7.56E−08 | 2.22E+06 | 1.67E−01 | 7.62E−08 | 2.44E+06 | 1.86E−01 |
| Jun | 7.48E−08 | 5.99E+07 | 4.48E+00 | 8.89E−08 | 8.74E+06 | 7.77E−01 |
| KRAS | 6.37E−08 | 4.77E+07 | 3.04E+00 | 6.20E−08 | 4.83E+06 | 3.00E−01 |
| LAT2 | 1.42E−07 | 1.44E+03 | 2.04E+02 | 1.18E−07 | 4.00E+04 | 4.71E−03 |
| LILRB3 | 8.63E−08 | 1.47E+07 | 1.27E+00 | 9.67E−08 | 4.01E+04 | 3.88E−03 |
| LYN | 1.06E−07 | 2.34E+09 | 2.48E+02 | 8.16E−08 | 2.19E+04 | 1.79E−03 |
| MALT1 | 1.29E−07 | 4.58E+08 | 6.41E+01 | | | |
| MAP2K1 | 8.78E−08 | 1.61E+07 | 1.42E+00 | 2.51E−06 | 2.10E+04 | 5.26E−02 |
| MAP2K2 | 7.06E−08 | 2.94E+08 | 2.08E+02 | 1.05E−07 | 5.60E+04 | 5.89E−03 |
| MAP2K3 | 9.62E−06 | 1.32E+07 | 1.27E+00 | 3.66E−08 | 2.21E+05 | 1.25E−02 |
| MAP3K3 | 1.10E−07 | 3.79E+06 | 4.15E−01 | 1.02E−07 | 6.50E+04 | 6.56E−03 |
| MAPK1 | 8.90E−08 | 2.65E+09 | 2.36E+02 | 1.15E−07 | 1.30E+05 | 1.49E−02 |
| MAPK12 | 1.01E−07 | 2.70E+09 | 2.72E+02 | 1.07E−07 | 4.07E+05 | 4.35E−02 |
| MAPK13 | 6.93E−08 | 9.21E+09 | 6.43E+02 | 1.45E−07 | 4.66E+05 | 6.76E−02 |
| MAPK14 | 6.54E−08 | 2.77E+06 | 1.81E−01 | 7.31E−08 | 3.80E+04 | 2.78E−03 |
| MAPK3 | 1.42E−07 | 1.66E+06 | 1.36E−01 | 8.50E−08 | 4.09E+04 | 3.48E−03 |
| MAPK8 | 7.79E−08 | 2.06E+09 | 1.61E+02 | | | |

-continued

| Binding kinetics and affinities of the RAC1 query obtained with NAPPA-SPRi | | | | | | |
|---|---|---|---|---|---|---|
| MAPK9 | 8.21E−08 | 1.64E+09 | 1.35E+02 | 8.33E−08 | 1.68E+05 | 1.40E−02 |
| MDM2 | 9.95E−08 | 4.11E+09 | 4.11E+02 | 1.59E−07 | 7.45E+07 | 1.19E+01 |
| MYC | 7.75E−08 | 2.50E+09 | 1.94E+02 | 8.43E−08 | 1.97E+08 | 1.65E+01 |
| NCK1 | 7.33E−08 | 7.62E+07 | 5.63E+00 | 3.22E+08 | 5.62E+04 | 1.31E−03 |
| NCKAP1L | 6.40E−08 | 1.72E+09 | 1.10E+02 | 1.45E−07 | 9.30E+08 | 1.35E+02 |
| NFAT5 | 6.35E−08 | 4.41E+08 | 1.89E−02 | | | |
| NFATC1 | 1.16E−07 | 4.63E+06 | 5.59E−01 | 2.91E−07 | 5.81E+05 | 1.69E−01 |
| NFATC3 | 1.36E−07 | 2.53E+04 | 3.44E−03 | | | |
| NFATC4 | 9.85E−08 | 5.29E+06 | 5.20E−01 | 1.72E−07 | 3.04E+05 | 5.21E−02 |
| NFKB1 | 1.91E−07 | 3.01E+06 | 1.53E+00 | 1.29E−07 | 3.26E+04 | 1.13E−02 |
| NFKBIA | 9.19E−08 | 1.52E+09 | 1.40E+02 | 8.03E−08 | 4.50E+04 | 3.61E−03 |
| NFKBIB | 6.87E−08 | 5.18E+06 | 3.56E−01 | 1.42E−07 | 1.52E+04 | 2.16E−03 |
| NFKBIE | 3.33E−07 | 7.94E+06 | 2.64E+00 | 1.14E−07 | 8.78E+04 | 1.00E−02 |
| NRAS | 1.04E−07 | 2.65E+07 | 2.75E+00 | 1.23E−07 | 9.22E+05 | 1.13E−01 |
| PIK3AP1 | 1.66E−07 | 2.86E+08 | 4.74E+01 | 1.44E−07 | 2.23E+06 | 3.21E−01 |
| PIK3CA | 6.80E−08 | 1.00E+09 | 6.82E+01 | 5.61E−08 | 3.86E+06 | 2.16E−01 |
| PIK3CB | 1.36E−07 | 1.19E+09 | 1.49E+02 | | | |
| PIK3CG | 9.50E−08 | 6.93E+08 | 6.58E+01 | 7.30E−08 | 4.02E+05 | 2.93E−02 |
| PIK3R1⁻ | 8.37E−08 | 1.03E+07 | 8.60E−01 | 7.17E−08 | 5.87E+04 | 4.21E−03 |
| PIK3R2 | 3.68E−08 | 3.96E+05 | 1.46E−02 | | | |
| PIK3R3 | 1.09E−07 | 7.19E+06 | 7.84E−01 | 1.24E−07 | 3.87E+04 | 4.81E−03 |
| PIK3R5 | 4.85E−08 | 2.40E+06 | 1.02E−01 | | | |
| PPP3CB | 1.34E−07 | 3.60E+04 | 4.83E−03 | 3.83E−08 | 5.44E+04 | 2.08E−03 |
| PPP3R1 | 1.43E−07 | 1.51E+09 | 2.17E+02 | 1.05E−07 | 3.04E+04 | 3.18E−03 |
| PRKCB | 9.62E−08 | 4.08E+06 | 3.93E−01 | 1.01E−07 | 3.62E+04 | 3.56R−03 |
| PTEN | 2.06E−07 | 2.77E+04 | 5.72E−03 | 8.33E−08 | 4.05E+04 | 3.37E−03 |
| PTPN6 | 1.39E−07 | 2.08E+07 | 2.89E+00 | 1.84E−07 | 2.62E+04 | 4.83E−03 |
| RAC1 | 5.16E−08 | 4.34E+06 | 2.24E−01 | 1.29E−07 | 6.39E+04 | 8.23E−03 |
| RAC3 | 1.29E−07 | 2.55E+06 | 3.15E−01 | 1.09E−07 | 3.00E+04 | 3.10E−03 |
| RAP1B | 9.09E−08 | 3.65E+09 | 3.32E+02 | 9.65E−08 | 4.09E+05 | 3.95E−02 |
| RAP2A | 8.46E−08 | 4.04E+09 | 3.42E+02 | 1.71E−07 | 1.26E+09 | 2.15E+02 |
| RAP2C | 9.63E−08 | 3.31E+09 | 3.19E+02 | 6.19E−08 | 6.06E+06 | 3.75E−01 |
| RasGRP3 | 9.42E−08 | 7.23E+07 | 6.81E+00 | 1.09E−07 | 2.91E+09 | 3.18E+02 |
| RASSF5 | 8.59E−08 | 9.65E+07 | 8.29E+00 | | | |
| RELA | 7.54E−08 | 3.07E+09 | 2.32E+02 | 1.38E−07 | 1.65E+04 | 2.27E−03 |
| RHOA | 1.36E−07 | 1.84E+08 | 2.52E+01 | 1.00E−07 | 3.34E+04 | 3.35E−03 |
| SOS1 | 9.53E−08 | 2.44E+08 | 2.82E+02 | 1.09E−07 | 7.32E+04 | 8.57E−03 |
| SOS2 | 8.59E−08 | 9.42E+05 | 8.10E−02 | 1.88E−07 | 8.19E+04 | 1.54E−02 |
| SYK | 8.10E−08 | 4.29E+07 | 3.47E+00 | 1.77E−07 | 1.02E+09 | 1.81E+02 |
| TEC | 7.82E−08 | 7.83E+08 | 6.13E+01 | 6.63E−08 | 1.60E+05 | 1.06E−02 |
| TP53 | 8.01E−08 | 5.95E+08 | 4.80E+01 | 1.22E−07 | 1.76E+06 | 2.14E−01 |
| VAV1 | 6.68E−08 | 2.72E+08 | 1.81E+01 | 9.71E−08 | 6.35E+05 | 6.74E−02 |
| VAV2 | 9.07E−08 | 3.98E+09 | 9.59E+02 | 1.06E−07 | 3.13E+09 | 3.31E+02 |
| VAV3 | 7.50E−08 | 4.00E+06 | 9.00E−01 | 1.27E−07 | 7.11E+09 | 9.06E+02 |

Reference Sequence ID = *BC063421, **BC120994, #BC006231, ##BC108694, ⁻BC030815, ⁻⁻BC094795
NP = target proteins are Not Phosphorylated.
LT = target proteins are Lysate-Treated.

| Binding kinetics of the RHOA query obtsined with NAPPA-SPRi | | | | | | |
|---|---|---|---|---|---|---|
| | RHOA(GDP)_NP | | | RHOA(GDP)_LT | | |
| Protein | KD | ka | kd | KD | ka | kd |
| AKT1 | 1.49E−07 | 5.90E+03 | 1.03E−03 | 9.29E−07 | 1.21E+3 | 1.12E−03 |
| AKT2* | 3.80E−07 | 5.93E+03 | 2.25E−03 | | | |
| AKT2** | 4.61E−07 | 5.11E+03 | 2.36E−03 | | | |
| AKT3 | | | | | | |
| ARHGDF7 | | | | | | |
| BCL10 | | | | | | |
| BCL2 | | | | | | |
| BCL2A1 | 3.77E−07 | 3.84E+03 | 1.45E−03 | 3.97E−07 | 2.35E+03 | 9.35E−04 |
| BCL2L1 | 4.06E−07 | 5.28E+03 | 2.12E−03 | | | |
| BLK | | | | | | |
| BLNK | | | | | | |
| BTK | | | | | | |
| CARD11 | 3.38E−07 | 7.46E+03 | 2.52E−03 | | | |
| CD19 | | | | | | |
| CD22 | | | | | | |
| CD72 | 4.34E−07 | 4.70E+03 | 2.04E−03 | | | |
| CD79B | | | | | | |
| CD81 | | | | | | |
| CDC42 | | | | | | |
| CDKN2A | | | | | | |

-continued

| Binding kinetics of the RHOA query obtsined with NAPPA-SPRi | | | | | |
|---|---|---|---|---|---|
| DAPP1 | | | | | |
| EGR1 | | | | | |
| ETS1 | 6.49E−08 | 1.44E+04 | 9.34E−04 | | |
| EZR | | | | | |
| FCGR2B | | | | | |
| Fos | | | | | |
| GRAP2 | | | | | |
| GRB2 | 3.95E−07 | 8.15E+03 | 3.21E−03 | | |
| GSK3B | | | | | |
| HRAS | | | | | |
| IFITM1 | | | | | |
| IKBKA | | | | | |
| IKBKB# | 4.54E−07 | 7.67E+03 | 3.49E−03 | | |
| IKBKB## | 3.75E−07 | 4.82E+03 | 1.81E−03 | | |
| IKBKG | 4.97E−07 | 6.62E+03 | 3.29E−03 | | |
| INPPSD | 3.82E−07 | 8.28E+03 | 3.15E−03 | | |
| INPPL1 | | | | | |
| Jun | | | | | |
| KRAS | | | | | |
| LAT2 | 1.14E−07 | 7.09E+03 | 8.10E−04 | | |
| LILRB3 | 4.72E−07 | 6.61E+03 | 3.12E−03 | | |
| LYN | | | | | |
| MAP2K2 | 3.69E−07 | 6.99E+03 | 2.58E−03 | | |
| MAP2K3 | 5.29E−07 | 4.79E+03 | 2.54E−03 | | |
| MAP3K3 | 7.13E−07 | 4.77E+03 | 3.40E−03 | | |
| MAPK1 | 1.42E−07 | 6.35E+03 | 9.02E−04 | | |
| MAPK12 | | | | | |
| MAPK13 | 9.02E−08 | 1.55E+04 | 1.24E−03 | 5.18E−08 | 2.07E+04 | 1.07E−03 |
| MAPK14 | 1.70E−07 | 1.14E+04 | 1.94E−03 | 2.52E−07 | 4.01E+03 | 1.01E−03 |
| MAPK3 | | | | | |
| MAPK8 | | | | | |
| MAPK9 | | | | | |
| MDM2 | 2.37E−07 | 8.92E+03 | 1.64E−03 | | |
| MYC | 3.39E−07 | 5.72E+03 | 1.94E−03 | | |
| NCK1 | | | | | |
| NCKAP1L | 2.59E−07 | 7.91E+03 | 2.05E−03 | | |
| NFAT5 | | | | | |
| NFATC1 | | | | | |
| NFATC3 | 3.31E−07 | 5.70E+03 | 1.89E−03 | | |
| NFATC4 | 3.20E−07 | 4.71E+03 | 1.51E−03 | | |
| NFKB1 | 3.15E−07 | 6.37E+03 | 2.01E−03 | | |
| NFKBIA | | | | | |
| NFKBIE | | | | | |
| NRAS | | | | | |
| PIK3AP1 | | | | | |
| PIK3CA | 2.36E−07 | 1.17E+04 | 2.77E−03 | | |
| PIK3CB | 3.58E−07 | 7.25E+03 | 2.59E−03 | | |
| PIK3CG | | | | | |
| PIK3R1⁻ | 3.25E−07 | 1.14E+04 | 3.71E−03 | | |
| PIK3R3 | | | | | |
| PIK3R5 | | | | | |
| PLCG2 | | | | | |
| PPP3CA | | | | | |
| PPP3CB | 2.88E−07 | 1.01E+04 | 2.89E−03 | | |
| PPP3R1 | 2.41E−07 | 7.50E+03 | 1.81E−03 | | |
| PPP3R2 | | | | | |
| PRKCA | | | | | |
| PRKCB | | | | | |
| PTEN | | | | | |
| PTPN6 | 3.34E−07 | 5.53E+03 | 1.98E−03 | | |
| RAC1 | | | | | |
| Raf1 | | | | | |
| RAP1B | | | | | |
| RAP2A | | | | | |
| RAP2C | 3.28E−07 | 7.05E+03 | 2.32E−03 | 4.87E−07 | 5.50E−07 | 2.68E−03 |
| RasGRP3 | | | | | |
| RASSF5 | | | | | |
| RELA | | | | | |
| RHOA | 1.63E−07 | 6.31E+03 | 1.35E−03 | | |
| SOS1 | | | | | |
| SOS2 | | | | | |
| SYK | | | | | |
| TEC | | | | | |
| TP53 | | | | | |

-continued

| Binding kinetics of the RHOA query obtsined with NAPPA-SPRi |
| --- |

VAV1
VAV2
VAV3

| | RHOA(GTP)_NP | | | RHOA(GTP)_LT | | |
| --- | --- | --- | --- | --- | --- | --- |
| Protein | KD | ka | kd | KD | ka | kd |
| AKT1 | 7.96E−08 | 1.22E+04 | 9.68E−04 | 1.14E−07 | 4.47E+03 | 5.11E−04 |
| AKT2* | 9.45E−08 | 1.47E+04 | 1.39E−03 | 1.34E−07 | 7.99E+03 | 1.07E−03 |
| AKT2** | 8.85E−08 | 1.12E+04 | 3.95E−04 | 3.43E−07 | 3.96E+03 | 1.36E−03 |
| AKT3 | 4.03E−07 | 6.27E+03 | 2.52E−03 | 2.30E−06 | 8.40E+02 | 2.00E−03 |
| ARHGDF7 | 1.26E−07 | 1.73E+04 | 2.10E−03 | 2.90E−07 | 7.09E+03 | 2.06E−03 |
| BCL10 | 2.73E−07 | 5.31E+03 | 1.45E−03 | | | |
| BCL2 | 1.10E−07 | 1.56E+04 | 1.72E−03 | | | |
| BCL2A1 | 1.25E−07 | 1.37E+04 | 1.72E−03 | 2.94E−07 | 4.36E+03 | 1.28E−03 |
| BCL2L1 | 1.64E−07 | 1.32E+04 | 2.17E−03 | 4.33E−07 | 3.72E+03 | 1.61E−03 |
| BLK | 1.80E−07 | 1.23E+04 | 2.22E−03 | 2.66E−07 | 6.63E+03 | 1.76E−03 |
| BLNK | 2.22E−07 | 1.10E+04 | 2.45E−03 | 7.48E−07 | 1.79E+03 | 1.34E−03 |
| BTK | 2.49E−07 | 1.08E+04 | 2.67E−03 | 8.12E−07 | 1.12E+03 | 9.13E−04 |
| CARD11 | 1.14E−07 | 1.28E+04 | 1.46E−03 | 2.43E−07 | 4.31E+03 | 1.07E−03 |
| CD19 | 2.86E−07 | 7.78E+03 | 2.22E−03 | 3.70E−07 | 4.90E+03 | 1.81E−03 |
| CD22 | 1.90E−07 | 1.51E+04 | 2.88E−03 | 6.28E−07 | 2.64E+03 | 1.66E−03 |
| CD72 | 7.24E−08 | 1.33E+04 | 9.59E−04 | 3.32E−07 | 2.89E+03 | 9.60E−04 |
| CD79B | 1.02E−07 | 1.59E+04 | 1.61E−03 | | | |
| CD81 | 1.45E−07 | 1.27E+04 | 1.84E−03 | | | |
| CDC42 | 9.69E−08 | 1.18E+04 | 1.14E−03 | | | |
| CDKN2A | 4.04E−07 | 3.02E+03 | 1.22E−03 | | | |
| DAPP1 | 1.42E−07 | 1.93E+04 | 2.75E−03 | | | |
| EGR1 | 1.20E−07 | 8.86E+03 | 1.06E−03 | | | |
| ETS1 | 1.48E−07 | 1.11E+04 | 1.65E−03 | 4.96E−07 | 2.26E+03 | 1.12E−03 |
| EZR | 2.09E−07 | 1.03E+04 | 2.15E−03 | 2.17E−06 | 5.03E+02 | 1.09E−03 |
| FCGR2B | 7.78E−08 | 1.50E+04 | 1.16E−03 | 1.62E−06 | 1.28E+03 | 2.08E−03 |
| Fos | 2.01E−07 | 1.01E+04 | 2.02E−03 | 1.22E−06 | 1.49E+03 | 1.81E−03 |
| GRAP2 | | | | 4.54E−07 | 4.68E+03 | 2.12E−03 |
| GRB2 | 1.26E−07 | 1.28E+04 | 1.61E−03 | 5.28E−08 | 1.10E+04 | 5.78E−05 |
| GSK3B | 1.16E−07 | 1.86E+04 | 2.17E−03 | | | |
| HRAS | 3.74E−07 | 6.16E+03 | 2.30E−03 | | | |
| IFITM1 | 2.34E−07 | 1.02E+04 | 2.38E−03 | 4.40E−07 | 1.67E+03 | 7.36E−04 |
| IKBKA | 2.67E−07 | 7.83E+03 | 2.09E−03 | 5.72E−09 | 4.87E+03 | 2.78E−05 |
| IKBKB# | 1.07E−07 | 1.67E+04 | 1.79E−03 | 2.01E−07 | 6.81E+03 | 1.91E−03 |
| IKBKB## | 1.04E−07 | 2.09E+04 | 2.18E−03 | 5.10E−07 | 2.63E+03 | 1.34E−03 |
| IKBKG | 1.29E−07 | 1.26E+04 | 1.63E−03 | 3.50E−07 | 3.11E+03 | 1.12E−03 |
| INPPSD | 2.96E−07 | 8.05E+03 | 2.38E−03 | 4.84E−08 | 4.20E+03 | 2.03E−04 |
| INPPL1 | 2.77E−07 | 1.01E+04 | 2.80E−03 | 4.76E−06 | 4.20E+02 | 2.00E−03 |
| Jun | 1.54E−07 | 1.25E+04 | 1.93E−03 | 1.19E−07 | 2.51E+03 | 2.99E−04 |
| KRAS | 1.44E−07 | 1.56E+04 | 2.24E−03 | | | |
| LAT2 | 6.21E−10 | 6.41E+03 | 3.98E−06 | 8.70E−07 | 1.79E+03 | 1.55E−03 |
| LILRB3 | 1.07E−07 | 1.25E+04 | 1.33E−03 | 9.95E−07 | 3.01E+03 | 3.00E−03 |
| LYN | 2.92E−07 | 8.33E+03 | 2.43E−03 | | | |
| MAP2K2 | 2.57E−07 | 9.27E+03 | 2.38E−03 | 2.85E−07 | 5.65E+03 | 7.62E−04 |
| MAP2K3 | 1.13E−07 | 1.50E+04 | 1.69E−03 | 6.36E−07 | 1.96E+03 | 1.28E−03 |
| MAP3K3 | 4.01E−07 | 3.60E+03 | 1.44E−03 | 3.12E−07 | 4.50E+03 | 1.40E−03 |
| MAPK1 | 1.25E−07 | 1.50E+04 | 1.87E−03 | 9.92E−08 | 4.75E+03 | 4.71E−04 |
| MAPK12 | 3.21E−07 | 7.50E+03 | 2.40E−03 | | | |
| MAPK13 | 1.85E−07 | 7.71E+03 | 1.42E−03 | 2.14E−07 | 5.21E+03 | 1.12E−03 |
| MAPK14 | 1.04E−07 | 1.55E+04 | 1.65E−03 | 2.85E−07 | 3.87E+03 | 1.11E−03 |
| MAPK3 | 1.27E−07 | 1.23E+04 | 1.56E−03 | 4.47E−07 | 3.83E+03 | 1.71E−03 |
| MAPK8 | 8.91E−07 | 1.65E+03 | 1.47E−03 | 1.32E−08 | 6.10E+03 | 8.07E−05 |
| MAPK9 | 3.13E−07 | 5.30E+03 | 1.66E−03 | 2.84E−08 | 5.31E+03 | 1.51E−04 |
| MDM2 | 1.08E−07 | 1.35E+04 | 1.43E−03 | 2.38E−07 | 6.51E+03 | 1.55E−03 |
| MYC | 1.70E−07 | 1.20E+04 | 2.04E−03 | 2.28E−07 | 3.37E+03 | 7.68E−04 |
| NCK1 | 1.63E−07 | 9.76E+03 | 1.59E−03 | 1.69E−07 | 5.72E+03 | 9.67E−04 |
| NCKAP1L | 1.00E−07 | 1.34E+04 | 1.34E−03 | 1.68E−07 | 5.41E+03 | 9.11E−04 |
| NFAT5 | | | | 4.07E−07 | 2.54E+03 | 1.04E−03 |
| NFATC1 | 1.99E−07 | 1.19E+04 | 1.66E−03 | 1.68E−06 | 1.05E+03 | 1.77E−03 |
| NFATC3 | | | | | | |
| NFATC4 | 1.55E−09 | 6.04E+03 | 9.39E−06 | | | |
| NFKB1 | | | | | | |
| NFKBIA | 2.20E−07 | 8.23E+03 | 1.81E−03 | | | |
| NFKBIE | 6.69E−08 | 1.63E+04 | 1.09E−03 | 2.62E−07 | 3.64E+03 | 9.56E−04 |
| NRAS | 2.03E−07 | 7.59E+03 | 1.54E−03 | | | |
| PIK3AP1 | 8.88E−07 | 1.36E+03 | 1.20E−03 | | | |
| PIK3CA | 1.14E−07 | 8.92E+03 | 1.01E−03 | 2.93E−08 | 2.79E+03 | 8.17E−05 |
| PIK3CB | 1.16E−07 | 1.28E+04 | 1.48E−03 | 5.59E−09 | 6.13E+03 | 3.39E−05 |
| PIK3CG | 3.50E−07 | 7.67 E+03 | 2.69E−03 | 1.45E−07 | 1.17E+04 | 1.70E−03 |
| PIK3R1⁻ | 9.55E−08 | 1.61E+04 | 1.53E−03 | 3.77E−07 | 3.32E+03 | 1.25E−03 |

-continued

| Binding kinetics of the RHOA query obtsined with NAPPA-SPRi | | | | | |
|---|---|---|---|---|---|
| PIK3R3 | | | | 8.18E−08 | 3.74E+03 | 3.05E−04 |
| PIK3R5 | 1.51E−07 | 1.32E+04 | 1.99E−03 | 9.99E−07 | 2.26E+03 | 2.26E−03 |
| PLCG2 | 2.22E−07 | 3.43E+03 | 7.60E−04 | 4.42E−06 | 3.88E+02 | 1.72E−03 |
| PPP3CA | 1.37E−07 | 2.02E+04 | 2.78E−03 | 4.87E−09 | 7.34E+03 | 3.58E−05 |
| PPP3CB | 1.24E−07 | 1.16E+04 | 1.44E−03 | 8.07E−06 | 2.08E+02 | 1.68E−03 |
| PPP3R1 | 2.28E−07 | 7.53E+03 | 1.71E−03 | 1.72E−07 | 3.36E+03 | 5.80E−04 |
| PPP3R2 | 1.65E−07 | 1.08E+04 | 1.77E−03 | 8.22E−08 | 4.83E+03 | 3.97E−04 |
| PRKCA | 1.47E−06 | 1.98E+03 | 2.90E−03 | 9.62E−08 | 3.73E+03 | 3.64E−04 |
| PRKCB | 1.56E−07 | 8.49E+03 | 1.33E−03 | 3.80E−07 | 3.04E+03 | 1.16E−03 |
| PTEN | 8.05E−07 | 3.26E+03 | 2.63E−03 | | | |
| PTPN6 | 3.98E−07 | 3.16E+03 | 1.26E−03 | | | |
| RAC1 | | | | 5.08E−07 | 3.59E+03 | 1.82E−03 |
| Raf1 | 2.32E−07 | 6.83E+03 | 1.59E−03 | | | |
| RAP1B | 5.56E−07 | 3.57E+03 | 1.98E−03 | 6.57E−06 | 2.81E+02 | 1.52E−03 |
| RAP2A | 1.56E−07 | 8.60E+03 | 1.42E−03 | 2.45E−07 | 3.40E+03 | 8.34E−04 |
| RAP2C | 1.12E−07 | 1.43E+04 | 1.63E−03 | 2.25E−06 | 1.07E+03 | 2.41E−03 |
| RasGRP3 | 1.94E−07 | 1.09E+04 | 1.47E−03 | | | |
| RASSF5 | 6.26E−07 | 2.40E+03 | 1.50E−03 | 2.01E−07 | 5.44E+03 | 1.10E−03 |
| RELA | 1.85E−07 | 1.23E+04 | 2.09E−03 | 2.70E−07 | 2.97E+03 | 8.00E−04 |
| RHOA | 5.17E−08 | 2.13E+04 | 1.10E−03 | 4.11E−07 | 3.37E+03 | 1.39E−03 |
| SOS1 | 1.77E−07 | 1.12E+04 | 1.99E−03 | | | |
| SOS2 | 1.03E−07 | 1.21E+04 | 1.26E−03 | 2.69E−07 | 3.15E+03 | 8.47E−04 |
| SYK | 1.03E−07 | 1.39E+04 | 1.42E−03 | 3.09E−07 | 4.67E+03 | 1.44E−03 |
| TEC | 1.85E−07 | 1.05E+04 | 1.95E−03 | 8.00E−07 | 3.76E+03 | 3.01E−03 |
| TP53 | 9.92E−07 | 2.30E+03 | 2.28E−03 | 1.14E−06 | 1.61E+03 | 1.84E−03 |
| VAV1 | 2.65E−07 | 7.91E+03 | 2.10E−03 | 4.93E−06 | 4.80E+02 | 2.37E−03 |
| VAV2 | 2.20E−07 | 6.96E+03 | 1.59E−03 | 3.67E−07 | 2.86E+03 | 1.05E−03 |
| VAV3 | 6.95E−08 | 3.20E+04 | 2.23E−04 | | | |

Reference Sequence ID = *BC063421, **BC120994, #BC006231, ##BC108694, ‾BC030815, ‾‾BC094795
NP = target proteins are Not Phosphorylated.
LT = target proteins are Lysate-Treated.

Sprite Software

NAPPA-SPRi data were analyzed using "SPRite" software, which was written in-house to analyze high throughput data using the Langmuir 1:1 binding model (Oshannessy, Brighamburke, Soneson, Hensley, & Brooks, 1993). The binding curves were first referenced to a non-binding interaction, zeroed at the injection start time, and baseline-corrected. The open-source SPRite script is available at mallicklab.stanford.edu.

Western Blot Analyses

Recombinant human BTK protein with an N-terminal His tag was obtained from Sino Biological (Wayne, PA). Recombinant human ETS1, JUN, and BCL2 proteins with an N-terminal His tag were obtained from RayBiotech (Norcross, GA), respectively. Recombinant human protein PI3K, constituting PIK3CA with an N-terminal His tag and untagged PIK3R1, was obtained from Thermo Fisher Scientific (Waltham, MA). Recombinant human MYC protein with an eleven-arginine tag at the C-terminus was obtained from Abcam (Cambridge, MA). MYC was first de-phosphorylated with 1200 units of lambda phosphatase for 2 hr at 30° C., and then 2 mM sodium orthovanadate was added to inhibit any further phosphatase activity. Kinase and substrate were mixed together at a 3:4 ratio (w/w) in 50 mM HEPES, pH 7.5, 100 mM NaCl, 10 mM MgCl2, 0.01% Brij-35, 1 mM ATP, and incubated at 30° C. for 1 hr. BTK samples with substrate and ATP were de-phosphorylated with 800 units of lambda protein phosphatase (New England BioLabs; Ipswich, MA) for 2 hrs at 30° C. 1× Laemmli loading dye (Bio-Rad; Hercules, CA) and 10 mM Bond-Breaker TCEP Solution, Neutral pH were added to the samples before heating at 65° C. for 10 min. Samples were added to SuperSep Phos-Tag™ (50 μmol/L), 12.5% SDS-PAGE gels (Wako Pure Chemical Industries; Richmond, VA) using tris-tricine running buffer containing 50 mM Tris, 50 mM N-[2-hydroxy-1,1-bis(hydroxymethyl)ethyl] glycine (Tricine), 0.10% (w/v) SDS, 5 mM sodium bisulfite. Gels were run at 100 V for 1 hr, and then transferred overnight to a PVDF membrane at 4° C. and 150 mA using the Bio-Rad Mini Trans-blot cell and 1× NuPAGE transfer buffer supplemented with 5 mM sodium bisulfite. Membranes were blocked with 3% BSA in PBST ("blocking buffer") for 1 hr at room temperature, and then probed with rabbit anti-human anti-c-Jun monoclonal antibody (clone 60A8; Cell Signaling Technology; Danvers, MA), anti-ETS1 monoclonal antibody (clone D808A; Cell Signaling Technology; Danvers, MA), anti-c-MYC monoclonal antibody (Abcam; Cambridge, MA), anti-c-MYC phospho S62 monoclonal antibody (Cell Signaling Technology; Danvers, MA), anti-c-MYC phospho T58 polyclonal antibody (Abcam; Cambridge, MA), or mouse anti-human BCL2 monoclonal antibody (Cell Signaling Technology; Danvers, MA) at a 1:1000 dilution in blocking buffer for 1 hr at room temperature. The membrane was washed three times in PBST, incubated for 1 hr at room temperature with HRP-conjugated anti-rabbit IgG (Cell Signaling Technology; Danvers, MA) or anti-mouse IgG (Jackson ImmunoResearch; West Grove, PA) at a 1:15, 000 dilution in blocking buffer, and then washed again three times in PBST. Signal was visualized using SuperSignal West Femto chemiluminescent substrate using the ImageQuant LAS 4000 system (GE Healthcare Life Science; Pittsburgh, PA).

Query Proteins Selected for Analyses

BLNK. BLNK is an adaptor that binds to many proteins, thereby bringing them into close proximity to each other to interact. BLNK is essential for B cell development and in BCR signaling. Mutations in BLNK have been demonstrated to cause immunodeficiences, and downregulation of BLNK occurs in mediastinal large B cell lymphomas and Hodgkin lymphomas. Thus, BLNK appears to act as a tumor suppressor.

BTK. BTK is a non-receptor tyrosine kinase that mediates different pathways in the B cell and, as such, acts as a bottleneck. It is essential for B cell development and differentiation. BTK mutations are the cause of a severe immunodefiency disease called X-linked agammaglobulinemia (XLA). Increased BTK activity is observed in several B cell cancers, including diffuse large B cell lymphoma, mantle cell lymphoma (MCL), and chronic lymphocytic leukemia (CLL). Since 2013, the FDA has approved small molecule inhibitors of BTK to treat MCL, CLL, and graft-versus-host disease.

PI3K. PI3K is most well-known for its lipid kinase activity, in which it phosphorylates the small signaling molecule, PIP2, to PIP3. It can also phosphorylate serine and threonine residues, most notably on itself and AKT1. It is critical for B cell metabolism, cell growth, development, and survival. Activating mutations are observed in 30% of cancers and some immunodeficiency disorders. PI3K is a heterodimer consisting of a catalytic and regulatory subunit, both of which have various isoforms. In these studies, the alpha isoforms of both the catalytic and regulatory subunits were used (i.e., PIK3CA and PIK3R1, respectively). These isoforms were chosen because, unlike the other isoforms, both PIK3CA and PIK3R1 are ubiquitously expressed. Moreover, PIK3CA is the only catalytic isoform that is frequently mutated in cancer, while PIK3R1 is the most frequently mutated regulatory subunit in cancer (i.e., 20%) (Herrero-Gonzalez & Di Cristofano, 2011; J. J. Zhao et al., 2006).

GTPases. RAC1 and RHOA are both Rho GTPases with roles in regulating the cytoskeleton during cell growth, adhesion, and migration. They are involved in B cell development, proliferation, endocytosis, and antigen presentation. They also regulate apoptosis and survival. Increased RAC1 expression or activity are implicated in the initiation and progression of several types of cancers, including those of the lung, breast, prostate, skin, colon, but their roles in B cell-related cancers are unknown. Mutations in RHOA are associated with Burkitt's lymphoma and diffuse large B cell lymphoma, Both the inactive and active forms of RAC1 and RHOA were analyzed with GDP and GTPYS, respectively. GTPYS was used for these experiments because it is non-hydrolyzable; a hydrolyzable GTP would result in interactions representing a mixture of active and inactive states. Thus, seven queries were employed for both NanoBRET and NAPPA-SPRi analyses.

AKT1 is a serine/threonine kinase that is activated downstream of PI3K in stimulated B cells. It promotes B cell growth, proliferation, survival, maturation, and survival. Increased activity of AKT1 is associated with a poorer prognosis in patients with diffuse large B cell lymphoma. DAPPI is an adaptor protein that, via its signalosome, stimulates the RAC1/JNK pathway involved in B cell adhesion and spreading (Al-Alwan, Hou, Zhang, Makondo, & Marshall, 2010b; Ulivieri & Baldari, 2005). It is also involved in MAPK/ERK signaling, which regulates cell proliferation and survival. LYN is a tyrosine kinase proximal to the membrane that quickly becomes activated upon BCR aggregation. It then activates SYK, another tyrosine kinase, via phosphorylation. LYN is important in B cell differentiation and B cell tolerance, while SYK is essential in calcium mobilization and B cell development. Finally, MAPK14 is a serine/threonine kinase that promotes B cell proliferation and survival. NAPPA-SPRi data analyses Guidelines Used for Determining Protein Interactions with NAPPA-SPRi 1.) Affinity had to be within the detection limits of the instrument: $1\text{E}^{-05}$ to $1\text{E}^{-14}$
2.) The curve had to look real by eye, while taking into account what the raw curve looked like.
3.) Had to be represented by at least two interactions across the four replicates (two duplicates for two concentrations).

Rule exceptions: 1) Interactions that were seen at least twice (by eye), but there was something wrong with all but one curve. For example, the kinetics were outside the range of the instrument or something weird happened during the dissociation phase that screwed up the numbers—like a bubble. 2) PI3K had very few interactions. Therefore, some interactors identified with PI3K were only identified by one binding curve. 3) Some interactions that were observed in the RHOA dataset once were also selected if the response was high (>100 RU after referencing).

Additional Information on NAPPA-SPRi Analyses

The kinetic data (ka, kd) was averaged within duplicates, then the $K_D$ was determined from these data. If the query interacted with the target protein with the fusion tag at the N- and C-terminus, then the interaction with the strongest affinity was selected to represent the interaction.

BLNK, PI3K, RAC1, and RHOA data were referenced to LIME1. Array proteins with an N-terminal HaloTag were referenced to N-terminally tagged LIME1, and array proteins with a C-terminal HaloTag were referenced to C-terminally tagged LIME1. BTK data were similarly referenced to N- or C-terminally tagged LUC2 (i.e., luciferase). Spot numbers refer to the spot location used from the Plexera Data Module software files.

All data was analyzed with SPRite "MGLLD" parameters except for the following: 1) RAC1 curves that had mass transport were processed with SPRite, but the kinetics were determined with Scrubber.

All data was analyzed with the lower-bound and upper-bound limits for drift correction as −/+ 20% except for the following: BTK and RHOA datasets. In these datasets, the lower-bound limit for drift correction was changed to 0% to + 20%. In the curveFittingKineticModels.py script (Appendix G), the line "11d_global_assoc_dissoc_param_bounds=((0, 0, 0,-assoc_slope_limit,-np.inf), (np.inf, np.inf. np.inf, assoc_slope_limit,np.inf))" under the "def assoc-dissocEqLLD_global" sub routine was changed to "11d_global_assoc_dissoc_param_bounds=((0, 0, 0, 0,-np.inf), (np.inf, np.inf. np.inf, assoc_slope_limit,np. inf))". The original bounds resulted in binding curves with strange-looking dissociation curves (e.g., curves that were 0 or negative kd).

Plasmid cDNA Deposition on SPR Slide

The quality of the printing onto the SPR slide was assessed using a fluorescent nucleic stain, PicoGreen® (Thermo Fisher Scientific; Waltham, MA). First, the slides were blocked with Tris-based SuperBlock (Thermo Fisher Scientific; Waltham, MA) to minimize non-specific binding overnight at 4° C. Then, PicoGreen® diluted in SuperBlock at 1:500 was applied to the slide, incubated in the dark for 10 min, washed three times in 1×PBS, rinsed in water, and dried under compressed air. Fluorescence was determined using the PowerScanner Micorarray™ from Tecan Group Ltd. (Switzerland).

Protein Expression on SPR Slide

The expression and subsequent capture of target proteins onto the SPR slides were assessed fluorescently. First, the slides were blocked with Tris-based SuperBlock (Thermo Fisher Scientific; Waltham, MA) to minimize non-specific binding overnight at 4° C. They were then washed in 1×PBS three times for 2 min each, rocking. The slides were rinsed in water and dried with compressed air. SPRi flow chambers (Plexera; Woodinville, WA) with 30 μL volume were applied onto the slides followed by 1-step human coupled in vitro protein expression mixture according to the manufacturer's instructions (Thermo Fisher Scientific; Waltham, MA). Expression was performed for 1.5 hours at 30° C. and then 30 min at 15° C. To remove the flow cells, the slides were placed at −80° C. for 30 sec. Slides were rinsed in 200 μL 1×PBS and blocked for 1 hour at RT with 5% milk in 1×PBST ("blocking buffer"). The slides were incubated in rabbit anti-HaloTag polyclonal antibody (Promega; Madison, WI) diluted 1:250 in blocking buffer for 1 hour at RT, rocking. After washing the slides three times in blocking buffer, the slides were incubated in Alexa Fluor 555 goat anti-rabbit IgG (Thermo Fisher Scientific; Waltham, MA) diluted 1:500 in blocking buffer for 1 hour at RT, rocking. The slides were then washed three times in 1×PBS, rinsed in water, and dried under compressed air. Fluorescence was determined using the PowerScanner Micorarray™ from Tecan Group Ltd. (Switzerland).

REFERENCES

Aldridge, B. B., Burke, J. M., Lauffenburger, D. A., & Sorger, P. K. (2006). Physicochemical modelling of cell signalling pathways. *Nature Cell Biology*, 8 (11), 1195-1203. doi: 10.1038/ncb1497

Davids, M. S. (2017). Targeting BCL-2 in B-cell lymphomas. *Blood*, 130 (9), 1081-1088. doi: 10.1182/blood-2017-04-737338

Davis, M. J., Ha, B. H., Holman, E. C., Halaban, R., Schlessinger, J., & Boggon, T. J. (2013). RAC1 (P29S) is a spontaneously activating cancer-associated GTPase. *Proceedings of the National Academy of Sciences of the United States of America*, 110 (3), 912-917. doi: 10.1073/pnas.1220895110 de Gorter, D. J. J., Vos, J. C. M., Pals, S. T., & Spaargaren, M. (2007). The B cell antigen receptor controls AP-1 and NFAT activity through Ras-mediated activation of Ral. *Journal of Immunology*, 178 (3), 1405-1414. doi: DOI 10.4049/jimmunol.178.3.1405

Deng, J., Isik, E., Fernandes, S. M., Brown, J. R., Letai, A., & Davids, M. S. (2015). Ibrutinib Therapy Increases BCL-2 Dependence and Enhances Sensitivity to Venetoclax in CLL. *Blood*, 126 (23).

England, C. G., Luo, H. M., & Cai, W. B. (2015). HaloTag Technology: A Versatile Platform for Biomedical Applications. *Bioconjugate Chemistry*, 26 (6), 975-986. doi: 10.1021/acs.bioconjchem.5b00191

Festa, F., Steel, J., Bian, X. F., & Labaer, J. (2013). High-throughput cloning and expression library creation for functional proteomics. *Proteomics*, 13 (9), 1381-1399. doi: 10.1002/pmic.201200456

Fumia, H. F., & Martins, M. L. (2013). Boolean Network Model for Cancer Pathways: Predicting Carcinogenesis and Targeted Therapy Outcomes. *Plos One*, 8 (7). doi: ARTN e69008 10.1371/journal.pone.0069008

Gonzalez, M. W., & Kann, M. G. (2012). *Chapter* 4: Protein Interactions and Disease. *Plos Computational Biology*, 8 (12). doi: ARTN e1002819 10.1371/journal.pcbi.1002819

Hall, M. P., Unch, J., Binkowski, B. F., Valley, M. P., Butler, B. L., Wood, M. G., . . . . Wood, K. V. (2012). Engineered Luciferase Reporter from a Deep Sea Shrimp Utilizing a Novel Imidazopyrazinone Substrate. *Acs Chemical Biology*, 7 (11), 1848-1857. doi: 10.1021/cb3002478

Herrero-Gonzalez, S., & Di Cristofano, A. (2011). New Routes to Old Places: PIK3R1 and PIK3R2 Join PIK3CA and PTEN as Endometrial Cancer Genes. *Cancer Discovery*, 1 (2), 106-107. doi: 10.1158/2159-8290.Cd-11-0116

Heydari, T., Heidari, M., Mashinchian, O., Wojcik, M., Xu, K., Dalby, M. J., . . . . Ejtehadi, M. R. (2017). Development of a Virtual Cell Model to Predict Cell Response to Substrate Topography. *Acs Nano*, 11 (9), 9084-9092. doi: 10.1021/acsnano.7b03732

Hiratsuka, T., Takei, Y., Ohmori, R., Imai, Y., Ozeki, M., Tamaki, K., . . . . Tsuruyama, T. (2016). ZFP521 contributes to pre-B-cell lymphomagenesis through modulation of the pre-B-cell receptor signaling pathway. *Oncogene*, 35 (25), 3227-3238. doi: 10.1038/one.2015.385

Ito, T., Chiba, T., Ozawa, R., Yoshida, M., Hattori, M., & Sakaki, Y. (2001). A comprehensive two-hybrid analysis to explore the yeast protein interactome. *Proceedings of the National Academy of Sciences of the United States of America*, 98 (8), 4569-4574. doi: DOI 10.1073/pnas.061034498

Janes, K. A., & Yaffe, M. B. (2006). Data-driven modelling of signal-transduction networks. *Nature Reviews Molecular Cell Biology*, 7 (11), 820-828. doi: 10.1038/nrm2041

Ji, S. (2012). *Molecular theory of the living cell: concepts, molecular mechanisms, and biomedical applications*. New York: Springer.

Karlsson, M., Ekeroth, J., Elwing, H., & Carlsson, U. (2005). Reduction of irreversible protein adsorption on solid surfaces by protein engineering for increased stability. *Journal of Biological Chemistry*, 280 (27), 25558-25564. doi: DOI 10.1074/jbc.M503665200

Karp, G., & Patton, J. G. (2013). *Cell and molecular biology: concepts and experiments* (7th ed.). Hoboken, NJ: John Wiley.

Karthikeyan, K., Barker, K., Tang, Y. Y., Kahn, P., Wiktor, P., Brunner, A., . . . . Qiu, J. (2016). A Contra Capture Protein Array Platform for Studying Post-translationally Modified (PTM) Auto-antigenomes. *Molecular & Cellular Proteomics*, 15 (7), 2324-2337. doi: 10.1074/mcp.M115.057661

Kirouac, D. C., Saez-Rodriguez, J., Swantek, J., Burke, J. M., Lauffenburger, D. A., & Sorger, P. K. (2012). Creating and analyzing pathway and protein interaction compendia for modelling signal transduction networks. Bmc Systems Biology, 6. doi: Artn 29 10.1186/1752-0509-6-29

Kitchen, J., Saunders, R. E., & Warwicker, J. (2008). Charge environments around phosphorylation sites in proteins. Bmc Structural Biology, 8. doi: Artn 19 10.1186/1472-6807-8-19

Kumawat, A., Chakrabarty, S., & Kulkarni, K. (2017). Nucleotide Dependent Switching in Rho GTPase: Conformational Heterogeneity and Competing Molecular Interactions. *Scientific Reports*, 7. doi: ARTN 45829 10.1038/srep45829

Logue, J. S., & Morrison, D. K. (2012). Complexity in the signaling network: insights from the use of targeted inhibitors in cancer therapy. *Genes & Development*, 26 (7), 641-650. doi: 10.1101/gad.186965.112

Machleidt, T., Woodroofe, C. C., Schwinn, M. K., Mendez, J., Robers, M. B., Zirnmerman, K., . . . . Wood, K. V. (2015). NanoBRET-A Novel BRET Platform for the Analysis of Protein-Protein Interactions. *Acs Chemical Biology,* 10 (8), 1797-1804. doi: 10.1021/acschembio.5b00143

Mathas, S., Hinz, M., Anagnostopoulos, I., Krappmann, D., Lietz, A., Jundt, F., . . . . Scheidereit, C. (2002). Aberrantly expressed c-Jun and JunB are a hallmark of Hodgkin lymphoma calls, stimulate proliferation and synergize with NF-kappa B. *Blood,* 100 (11), 742a-742a.

Mayeux, J., Skaug, B., Luo, W., Russell, L. M., John, S., Saelee, P., . . . . Satterthwaite, A. B. (2015). Genetic Interaction between Lyn, Ets1, and Btk in the Control of Antibody Levels. *Journal of Immunology,* 195 (5), 1955-1963. doi: 10.4049/jimmunol.1500165

Middendorp, S., Dingjan, G. M., Maas, A., Dahlenborg, K., & Hendriks, R. W. (2003). Function of Bruton's tyrosine kinase during B cell development is partially independent of its catalytic activity. *Journal of Immunology,* 171 (11), 5988-5996.

Murray, D., Matsumoto, L. H., Buser, C. A., Tsang, J., Sigal, C. T., Ben-Tal, N., . . . . McLaughlin, S. (1998). Electrostatics and the membrane association of Src: Theory and experiment. *Biochemistry,* 37 (8), 2145-2159. doi: DOI 10.1021/bi972012b Nishi, H., Hashimoto, K., & Panchenko, A. R. (2011). Phosphorylation in Protein-Protein Binding: Effect on Stability and Function. *Structure,* 19 (12), 1807-1815. doi: 10.1016/j.str.2011.09.021

Nishi, H., Shaytan, A., & Panchenko, A. R. (2014). Physicochemical mechanisms of protein regulation by phosphorylation. Frontiers in Genetics, 5. doi: ARTN 270 10.3389/fgene.2014.00270

Okada, T., Maeda, A., Iwamatsu, A., Gotoh, K., & Kurosaki, T. (2000). BCAP: The tyrosine kinase substrate that connects B cell receptor to phosphoinositide 3-kinase activation. *Immunity,* 13 (6), 817-827. doi: Doi 10.1016/S1074-7613 (00) 00079-0

Oshannessy, D. J., Brighamburke, M., Soneson, K. K., Hensley, P., & Brooks, I. (1993). Determination of Rate and Equilibrium Binding Constants for Macromolecular Interactions Using Surface-Plasmon Resonance-Use of Nonlinear Least-Squares Analysis-Methods. *Analytical Biochemistry,* 212 (2), 457-468. doi: DOI 10.1006/abio.1993.1355

Pollard, T. D. (2010). A guide to simple and informative binding assays. *Molecular Biology of the Cell,* 21 (23), 4061-4067. doi: 10.1091/mbc.E10-08-0683

Porter, A. P., Papaioannou, A., & Malliri, A. (2016). Deregulation of Rho GTPases in cancer. *Small GTPases,* 7 (3), 123-138. doi: 10.1080/21541248.2016.1173767

Prasad, T. S. K., Goel, R., Kandasamy, K., Keerthikumar, S., Kumar, S., Mathivanan, S., . . . . Pandey, A. (2009). Human Protein Reference Database-2009 update. *Nucleic Acids Research,* 37, D767-D772. doi: 10.1093/nar/gkn892

Ramachandran, N., Hainsworth, E., Bhullar, B., Eisenstein, S., Rosen, B., Lau, A. Y., . . . . LaBaer, J. (2004). Self-assembling protein microarrays. *Science,* 305 (5680), 86-90. doi: DOI 10.1126/science. 1097639

Ramachandran, N., Raphael, J. V., Hainsworth, E., Demirkan, G., Fuentes, M. G., Rolfs, A., . . . . LaBaer, J. (2008). Next-generation high-density self-assembling functional protein arrays. *Nature Methods,* 5 (6), 535-538. doi: 10.1038/Nmeth.1210

Rauf, F., Festa, F., Park, J. G., Magee, M., Eaton, S., Rinaldi, C., . . . . LaBaer, J. (2018). Ibrutinib inhibition of ERBB4 reduces cell growth in a WNT5A-dependent manner. *Oncogene.* doi: 10.1038/s41388-017-0079-x Russell, L., John, S., Cullen, J., Luo, W., Shlomchik, M. J., & Garrett-Sinha, L. A. (2015). Requirement for Transcription Factor Ets1 in B Cell Tolerance to Self-Antigens. *Journal of Immunology,* 195 (8), 3574-3583. doi: 10.4049/jimmunol.1500776

Sachs, K., Perez, O., Pe'er, D., Lauffenburger, D. A., & Nolan, G. P. (2005). Causal protein-signaling networks derived from multiparameter single-cell data. *Science,* 308 (5721), 523-529. doi: 10.1126/science.1105809

Saito, K., Tolias, K. F., Saci, A., Koon, H. B., Humphries, L. A., Scharenberg, A., . . . . Carpenter, C. L. (2003). BTK regulates PtdIns-4,5-P-2 synthesis: Importance for calcium signaling and PI3K activity. Immunity, 19 (5), 669-678. doi: Doi 10.1016/S1074-7613 (03) 00297-8

Saul, J., Petritis, B., Sau, S., Rauf, F., Gaskin, M., Ober-Reynolds, B., . . . . LaBaer, J. (2014). Development of a full-length human protein production pipeline. *Protein Science,* 23 (8), 1123-1135. doi: 10.1002/pro.2484

Schinzel, A., Kaufmann, T., & Borner, C. (2004). Bcl-2 family members: intracellular targeting, membrane-insertion, and changes in subcellular localization. *Biochimica Et Biophysica Acta-Molecular Cell Research,* 1644 (2-3), 95-105. doi: 10.1016/j.bbamcr.2003.09.006

Schreiber, G., Haran, G., & Zhou, H. X. (2009). Fundamental Aspects of Protein-Protein Association Kinetics. *Chemical Reviews,* 109 (3), 839-860. doi: 10.1021/cr800373w Serber, Z., & Ferrell, J. E. (2007). Tuning bulk electrostatics to regulate protein function. *Cell,* 128 (3), 441-444. doi: 10.1016/j.cell.2007.01.018

Stark, C., Breitkreutz, B. J., Reguly, T., Boucher, L., Breitkreutz, A., & Tyers, M. (2006). BioGRID: a general repository for interaction datasets. *Nucleic Acids Research,* 34, D535-D539. doi: 10.1093/nar/gkj109

Stumpf, M. P. H., Thorne, T., de Silva, E., Stewart, R., An, H. J., Lappe, M., & Wiuf, C. (2008). Estimating the size of the human interactome. *Proceedings of the National Academy of Sciences of the United States of America,* 105 (19), 6959-6964. doi: 10.1073/pnas.0708078105

Tarrant, M. K., & Cole, P. A. (2009). The Chemical Biology of Protein Phosphorylation. *Annual Review of Biochemistry,* 78, 797-825. doi: 10.1146/annurev.biochem.78.070907.103047

Testoni, M., Chung, E. Y. L., Priebe, V., & Bertoni, F. (2015). *The transcription factor ETS1 in lymphomas: friend or foe? Leukemia & Lymphoma,* 56 (7), 1975-1980. doi: 10.3109/10428194.2014.981670

Troen, G., Nygaard, V., Jenssen, T. K., Ikonomou, I. M., Tierens, A., Matutes, E., . . . . Delabie, J. (2004). Constitutive expression of the AP-1 transcription factors c-jun, junD, junB, and c-fos and the marginal zone B-cell transcription factor notch2 in splenic marginal zone lymphoma. Journal of Molecular Diagnostics, 6 (4), 297-307. doi: Doi 10.1016/S1525-1578 (10) 60525-9

Tsuchiya, A., Kanno, T., & Nishizaki, T. (2014). PI3 kinase directly phosphorylates Akt1/2 at Ser473/474 in the insulin signal transduction pathway. Journal of Endocrinology, 220 (1), 49-59. doi: 10.1530/Joe-13-0172

Vetter, I. R., & Wittinghofer, A. (2001). Signal transduction—The guanine nucleotide-binding switch in three dimensions. *Science,* 294 (5545), 1299-1304. doi: DOI 10.1126/science.1062023

Wang, J., Barker, K., Steel, J., Park, J., Saul, J., Festa, F., . . . . Qiu, J. (2013). A versatile protein microarray platform enabling antibody profiling against denatured proteins. *Proteomics Clinical Applications,* 7 (5-6), 378-383. doi: 10.1002/prca.201200062

Woolery, A. R., Yu, X. B., LaBaer, J., & Orth, K. (2014). AMPylation of Rho GTPases Subverts Multiple Host Signaling Processes. *Journal of Biological Chemistry*, 289 (47). doi: 10.1074/jbc.M114.601310

Yarbrough, M. L., Li, Y., Kinch, L. N., Grishin, N. V., Ball, H. L., & Orth, K. (2009). AMPylation of Rho GTPases by *Vibrio* VopS Disrupts Effector Binding and Downstream Signaling. *Science,* 323 (5911), 269-272. doi: 10.1126/science.1166382

Yu, X., Petritis, B., Duan, H., Xu, D., & LaBaer, J. (2018). Advances in cell-free protein array methods. *Expert Rev Proteomics,* 15 (1), 1-11. doi: 10.1080/14789450.2018.1415146

Yu, X. B., & LaBaer, J. (2015). High-throughput identification of proteins with AMPylation using self-assembled human protein (NAPPA) microarrays. *Nature Protocols,* 10 (5), 756-767. doi: 10.1038/nprot.2015.044

Zhao, J. J., Cheng, H. L., Jia, S. D., Wang, L., Gjoerup, O. V., Mikami, A., & Roberts, T. M. (2006). The p110 *alpha isoform of PI*3K is essential for proper growth factor signaling and oncogenic transformation. *Proceedings of the National Academy of Sciences of the United States of America,* 103 (44), 16296-16300. doi: 10.1073/pnas.0607899103

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of detecting interactions between a targeting agent and one or more proteins of interest using surface plasmon resonance imaging (SPRi), comprising:

providing a set of proteins of interest on a protein microarray, wherein:

each spot in the protein microarray comprises a protein of interest;

the protein of interest is covalently linked to the solid or semisolid surface by attaching the set of proteins of interest to a solid or semisolid surface using a capture moiety that specifically binds a targeting moiety on each protein of interest; and the set of proteins of interest is produced and printed on an array using a cell-free protein expression system consisting of a printing mix that consists of:

plasmid DNA encoding a protein from the set of proteins of interest, wherein each protein in the set of proteins of interest is fusion tagged with the targeting moiety; and a poly(L-lysine) polymer, wherein the poly(L-lysine) polymer is a DNA capturing reagent that captures the plasmid DNA;

contacting the protein microarray with a targeting agent that binds to one or more of the set of proteins of interest; and detecting the binding of the targeting agent to the set of proteins of interest using SPRi, thereby detecting the targeting agent and one or more proteins of interest in the microarray.

2. The method of claim 1, further comprising modifying the set of proteins by post-translational modification (PTM).

3. The method of claim 2, wherein the post-translational modification comprises one or more of phosphorylation, AMPylation, citrullination or glycosylation.

4. The method of claim 1, wherein the capture moiety comprises an antibody, streptavidin, biotin, or avidin.

5. The method of claim 4, wherein the solid or semisolid surface comprises an amine-terminated polyethylene glycol [HS—C$_{11}$ (C$_2$H$_4$O)$_6$—NH$_2$], alkanes and glycols of varying lengths, or a mixture of amine-terminated and non-amine-terminated spacers.

6. The method of claim 5, wherein the amine-terminated polyethylene glycol monolayer covalently links the poly-L-lysine polymer and capture moiety to the solid or semisolid surface using a reactive sulfo-NHS ester amine-to-amine crosslinker (BS3), which is activated at time of printing.

7. The method of claim 6, wherein the capture moiety comprises a chloroalkane ligand and the proteins comprise a Halo-Tag.

8. The method of claim 1, wherein the solid or semisolid surface is a slide.

9. The method of claim 1, wherein producing a set of proteins of interest using a cell-free protein expression system, comprises "cover capture" in which plasmid cDNA is printed within microwells on the solid or semisolid surface which is one slide, and wherein at the time of protein expression, the plasmid cDNA slide is sandwiched to a second slide pre-coated with capturing ligand, resulting in a separation of plasmid cDNA and expressed protein.

10. The method of claim 7, wherein the plasmid cDNA and expressed protein are within the same spot.

11. The method of claim 1, wherein the method allows greater than 400 different protein interactions to be detected in less than one hour.

12. The method of claim 1, further comprising: determining the affinity and/or binding kinetics of the targeting agent to one or more of the set of proteins of interest.

13. The method of claim 1, wherein the targeting agent comprises a protein, a nucleic acid, or a combination thereof.

14. A method of detecting greater than 400 different protein interactions between a targeting agent and one or more proteins of interest in less than an hour, comprising:

providing a set of proteins of interest on a protein microarray, wherein:

each spot in the protein microarray comprises a protein of interest;

the protein of interest is covalently linked to the solid or semisolid surface by attaching the set of proteins of interest to a solid or semisolid surface using a capture moiety that specifically binds a targeting moiety on each protein of interest; and the set of proteins of interest is produced and printed on an array using a cell-free protein expression system consisting of a printing mix that consists of:

plasmid DNA encoding a protein from the set of proteins of interest, wherein each protein in the set of proteins of interest is fusion tagged with the targeting moiety; and a poly(L-lysine) polymer, wherein the poly(L-lysine) polymer is a DNA capturing reagent that captures the plasmid DNA;

contacting the protein microarray with a targeting agent that binds to one or more of the set of proteins of interest, wherein the targeting agent comprises a protein, a nucleic acid, or a combination thereof;

detecting the binding of the targeting agent to the set of proteins of interest using surface plasmon resonance imaging (SPRi), thereby detecting the targeting agent and one or more proteins of interest in the microarray; and determining the affinity and/or binding kinetics of the targeting agent to one or more of the set of proteins of interest.

* * * * *